(12) United States Patent
Nag et al.

(10) Patent No.: US 11,987,551 B2
(45) Date of Patent: May 21, 2024

(54) STYRYL CARBOXYLATE DERIVATIVES

(71) Applicant: Renovel Innovations, Inc, Fremont, CA (US)

(72) Inventors: Bishwajit Nag, Union City, CA (US); Ananda Sen, Castro Valley, CA (US); Nitish Nag, Union City, CA (US); Arjun Sanyal, Castro Valley, CA (US); Srinivasan Narasimhan, Chennai (IN)

( * ) Notice: Subject to any disclaimer, the term of this patent is extended or adjusted under 35 U.S.C. 154(b) by 0 days.

(21) Appl. No.: 17/372,383

(22) Filed: Jul. 9, 2021

(65) Prior Publication Data

US 2022/0234987 A1 Jul. 28, 2022

Related U.S. Application Data

(60) Provisional application No. 63/141,816, filed on Jan. 26, 2021.

(51) Int. Cl.
*C07C 69/618* (2006.01)
*C07C 219/28* (2006.01)
*C07C 251/86* (2006.01)
*C07C 257/08* (2006.01)
*C07C 291/00* (2006.01)

(52) U.S. Cl.
CPC .......... *C07C 69/618* (2013.01); *C07C 219/28* (2013.01); *C07C 251/86* (2013.01); *C07C 257/08* (2013.01); *C07C 291/00* (2013.01)

(58) Field of Classification Search
None
See application file for complete search history.

(56) References Cited

PUBLICATIONS

Dyrager et al. (Bioorganic & Medicinal Chem., 2011, 19(8), 2659) teaches (Year: 2011).*

* cited by examiner

*Primary Examiner* — Sudhakar Katakam
*Assistant Examiner* — Jennifer C Sawyer
(74) *Attorney, Agent, or Firm* — GSS Law Group; Gregory S. Smith; Adam Bell

(57) ABSTRACT

Novel Styryl Carboxylate derivatives are provided which exhibit activity for the treatment of immunological diseases, inflammation, obesity, hyperlipidemia, hypertension, neurological diseases, and diabetes.

16 Claims, 31 Drawing Sheets

Statistical significance was observed with Compound 1 (*p<0.0001) when compared with the high fat diet group.

*p<0.002 when compared with the high fat diet group.

**p<0.009 when compared with the high fat diet group.

Effect of Compounds 2, 3, 4, and 5
on Fasting Blood Glucose at 60 days in C57BL/6 mice Effect of Compounds 2, 3, 4, and 5
on OGTT at 60 days in C57BL/6 mice Effect of Compounds 2, 3, 4, and 5
on OGTT at 60 days in 30 mins in C57BL/6 mice Statistical Significance of $P<0.03$ Statistical significance was observed with Compound 8 (#p<0.0001) when compared with the high fat diet group.

STYRYL CARBOXYLATE DERIVATIVES

RELATIONSHIP TO OTHER APPLICATIONS

This application claims the benefit of and priority to U.S. Provisional Application No. 63/141,816 filed 26 Jan. 2021, which is incorporated herein by reference.

FIELD OF THE INVENTION

The present invention relates to novel styryl carboxylates for the treatment of immunological diseases, inflammation, obesity, hyperlipidaemia, hypertension, neurological diseases, and diabetes.

BACKGROUND OF THE INVENTION

Metabolic syndrome, Insulin resistance syndrome or Syndrome X is a name for a group of risk factors that occur together and increase the risk for coronary artery disease, stroke, and type 2 diabetes. Metabolic syndrome is becoming more and more common globally specially in the United States. Researchers are not sure whether the syndrome is due to one single cause, but all the risks for the syndrome are related to obesity. The two most important risk factors for metabolic syndrome are: Extra weight around the middle and upper parts of the body (central obesity) and insulin resistance. The body uses insulin less effectively than normal. Insulin is needed to help control the amount of sugar in the body. As a result, blood sugar and fat levels rise. Other risk factors include Aging, Genes, Hormone changes, Lack of exercise. People who have metabolic syndrome often have two other problems that can either cause the condition or make it worse. Excess blood clotting, and increased levels of blood substances that are a sign of inflammation throughout the body.

Metabolic syndrome is affiliated with three or more of the following signs: Blood pressure equal to or higher than 130/85 mmHg, Fasting blood sugar (glucose) equal to or higher than 100 mg/dL, large waist circumference (length around the waist Men—40 inches or more and Women—35 inches or more, Low HDL cholesterol (Men—under 40 mg/dL Women—under 50 mg/dL) and Triglycerides equal to or higher than 150 mg/dL. In general, metabolic syndrome is a combination of Type 2 diabetes, obesity, hyperlipidemia and hypertension.

People with metabolic syndrome have an increased long-term risk for developing heart disease, type 2 diabetes, stroke, kidney disease, and poor blood supply to the legs. There is no one single treatment option available to treat metabolic syndrome. Current drugs that control blood glucose are usually not effective in lowering body weight, hypertension and cholesterol. Similarly, drugs that manage lipid levels may or may not have impact on other metabolic parameters. The present invention was aimed to develop new class of therapeutics derived, modified, and chemically synthesized from natural product which can combat multiple arms of metabolic syndrome. The invention also describes one such core group of molecules with synthesis scheme and biological data for diabetes, obesity, inflammation, hypertension and hyperlipidemia.

The compounds and compositions of the present invention are used to treat diseases associated with Inflammation, which include (but are not limited to) the following: Chron's Disease, Appendicitis, Bursitis, Colitis, Cystitis, Dermatitis, Epididymitis, Gingivitis, Meningitis, Myelitis, Nephritis, Neuritis, Pancreatitis, Periodontitis, Pharyngitis, Phlebitis, Prostatitis, Sinusitis, Tendonitis, Tonsillitis, Urethritis, Vasculitis, Vaginitis, Rheumatoid Arthritis, Osteoarthritis, Psoriatic Arthritis, Septic Arthritis, Chronic Inflammation, Asthma, Hepatitis, Laryngitis, Thyroiditis, Lymphangitis, Gout, Arteritis, Bronchitis, Acne Vulgaris, Pneumonia, Sarcoidosis, Endocarditis, Myocarditis, Pericarditis, Duodenitis, Esophagitis, Folliculitis, Anemia, Hypersensitivity, Chronic Obstructive Pulmonary Disease, Complex Regional Pain Syndrome, Rhinitis and Celiac Disease.

The compounds and compositions of the present invention are used to treat diseases associated with Metabolic Syndrome, which include (but are not limited to) the following: Obesity, Dyslipidemia, Hyperglycemia, Non Alcoholic Fatty Liver Disease, Polycystic Ovary Syndrome, Sleep Apnea, Hyperinsulinemia, Insulin Resistance, Glucose Intolerance, Hypertension, Acanthosis *Nigricans*, Psoriasis, Coronary Artery Disease, Cardiac Arrest, Congestive Heart Failure, Arrhythmia, Peripheral Artery Disease, Stroke, Ischemic Heart Disease, Lipodystrophy, Diabetes Mellitus Type 2, Kidney Failure, Low Levels of HDL and Chronic Inflammation.

SUMMARY OF THE INVENTION

The present invention relates to novel Styryl Carboxylate derivatives of the formula (I)

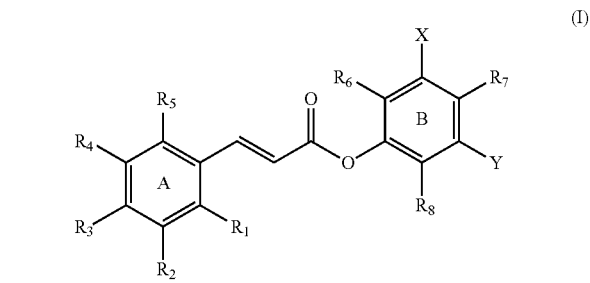

their analogs, their tautomeric forms, their stereoisomers, their polymorphs, their pharmaceutically acceptable salts, their pharmaceutically acceptable solvates, wherein $R_1$, $R_2$, $R_3$, $R_4$ and $R_5$ represent substituents on ring A and $R_6$, $R_7$ and $R_8$ along with X and Y represent substituents on ring B as indicated in formula (I).

The present invention also relates to a process for the preparation of the above said novel compounds, their analogs, their tautomeric forms, their stereoisomers, their polymorphs, their pharmaceutically acceptable salts, their pharmaceutically acceptable solvates, novel intermediates and pharmaceutical compositions containing them. Tautomeric forms are isomeric forms which exists in a state of equilibrium capable of reacting according to either form. Stereoisomers include configurational isomers, such as cis- and trans double bonds, as well as optically active isomers having different spatial arrangements of their atoms. Polymorphs are molecules which can crystallize in two or more forms. Solvates are molecular or ionic complexes of molecules or ions of solvent with those of a solute. Analogs also include atoms of the same family of the Periodic Table, such as F, Cl, Br and I. Derivatives include compounds resulting from routine functionalizing of atoms, such as, derivatives found by protecting by carboxylation or esterification, respectively.

DETAILED DESCRIPTION OF THE INVENTION

Figure 1A:
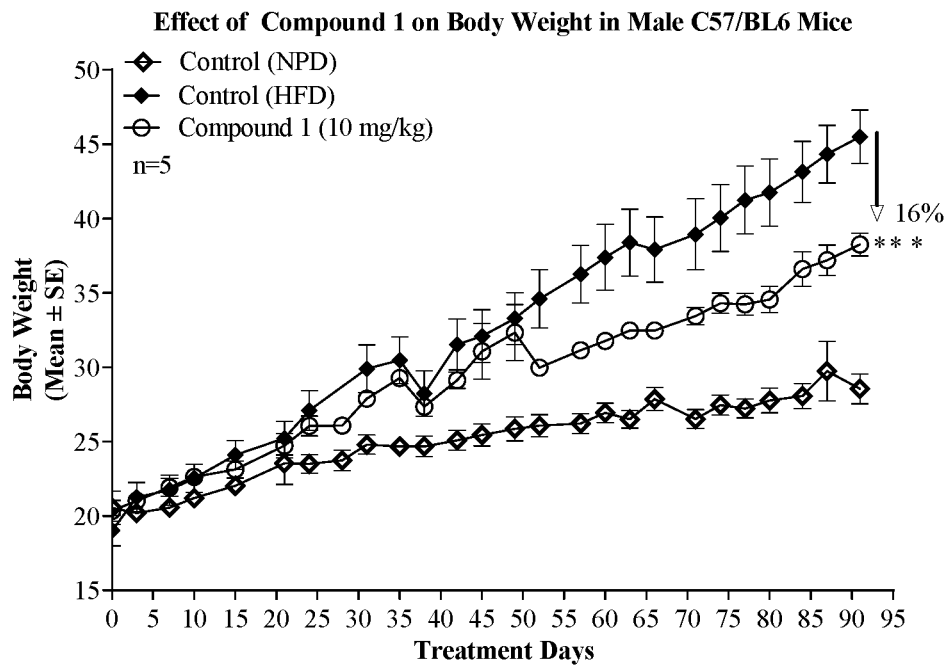
FIG. 1 shows that mice treated with compound 1 showed a significant decrease (P<0.0001) by 16% in body weight compared with the Control high fat diet group.
Figure 1B:
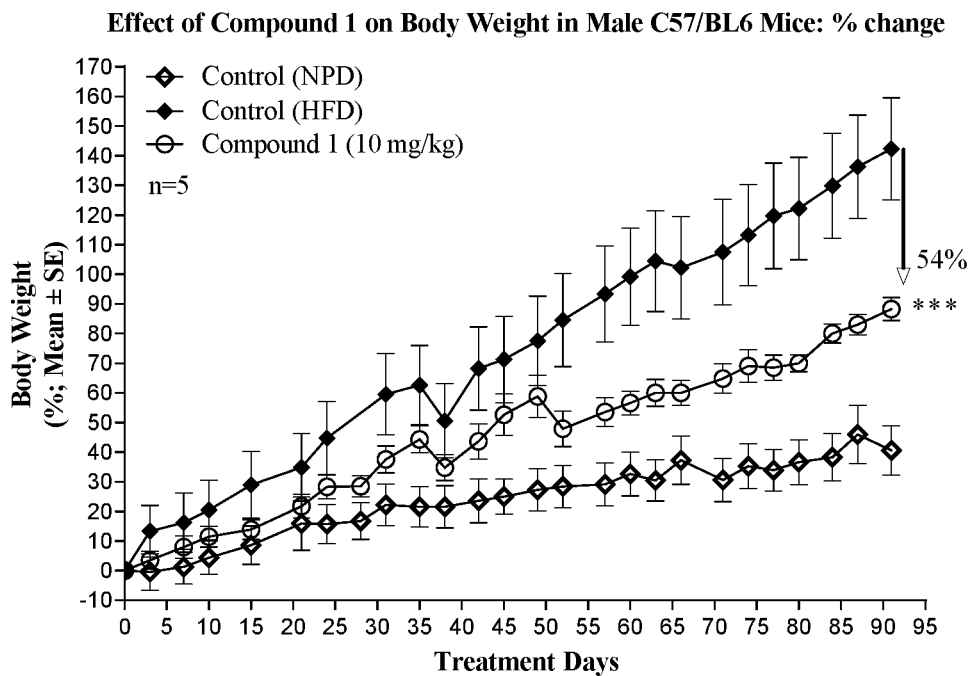
Figure 2:
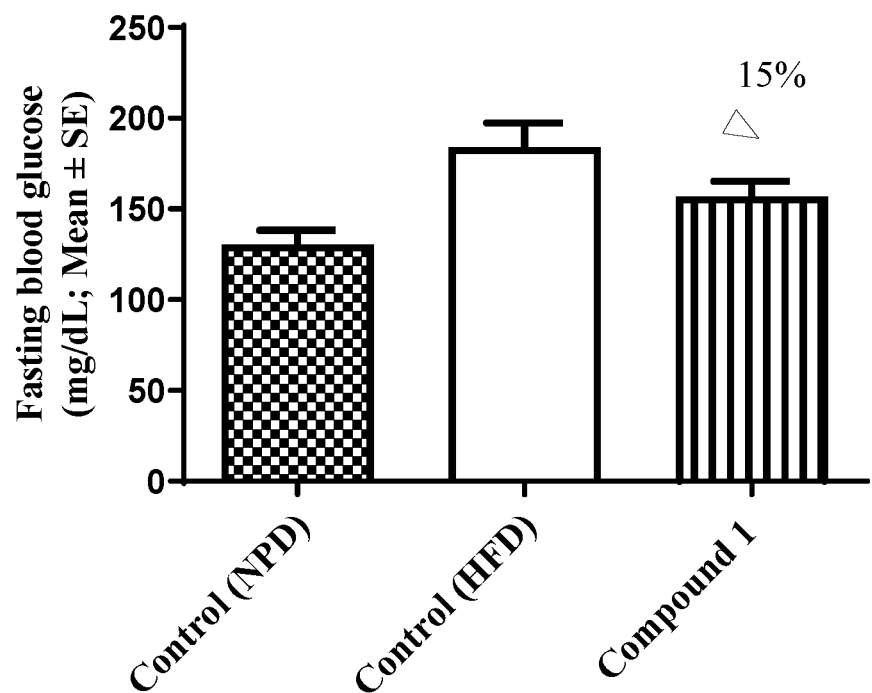
FIG. 2 shows that mice treated with compound 1 showed 15% reduction in fasting blood glucose compared with the control group high fat diet group.
Figure 3A:
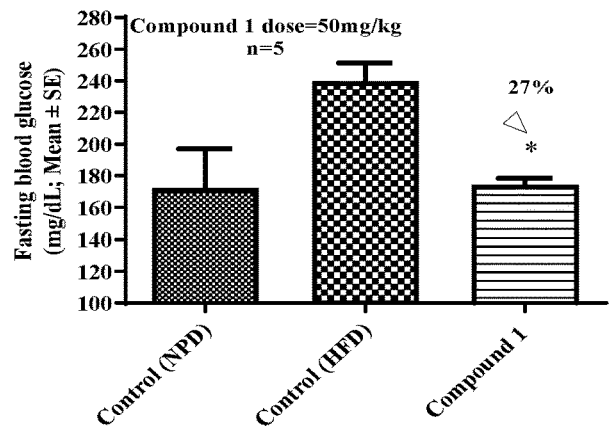
FIG. 3 shows that group of mice treated with compound 1 showed a significant reduction (P<0.002) by 27% in fasting blood glucose compared with the group of mice maintained on high fat diet (FIG. 3B). The group of mice treated with compound 1 showed a significant decrease (P<0.009) by 28% in blood glucose compared at the peak oral glucose tolerance test of 30 minutes compared with the Control high fat diet group (FIG. 3C).
Figure 3B:
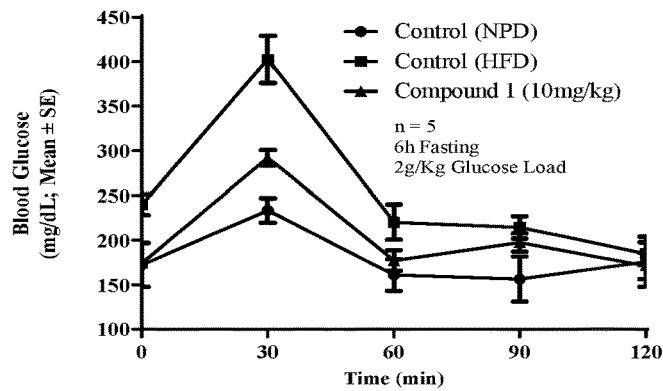
Figure 3C:
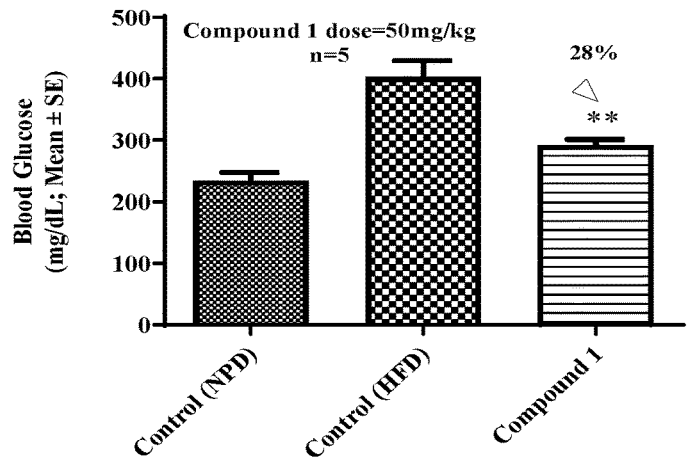
Figure 4:
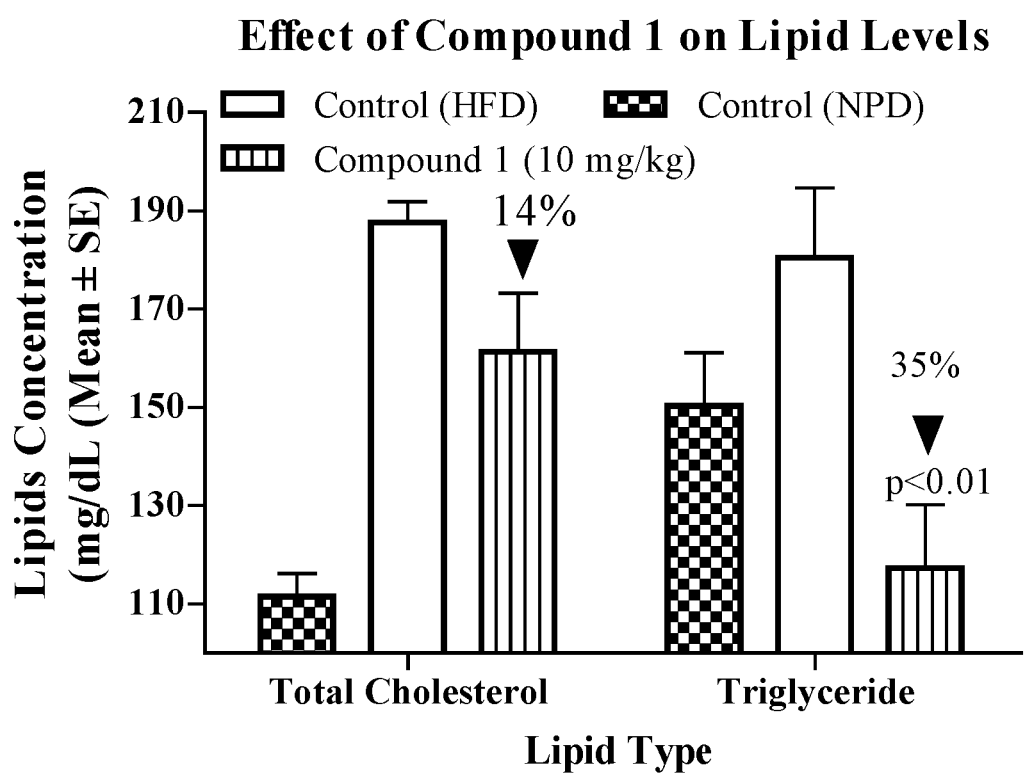
FIG. 4 shows that mice treated with compound 1 showed a 14% decrease in Total Cholesterol and a significant decrease (P<0.01) by 35% in Triglyceride, compared with the Control high fat diet group.
Figure 5A:
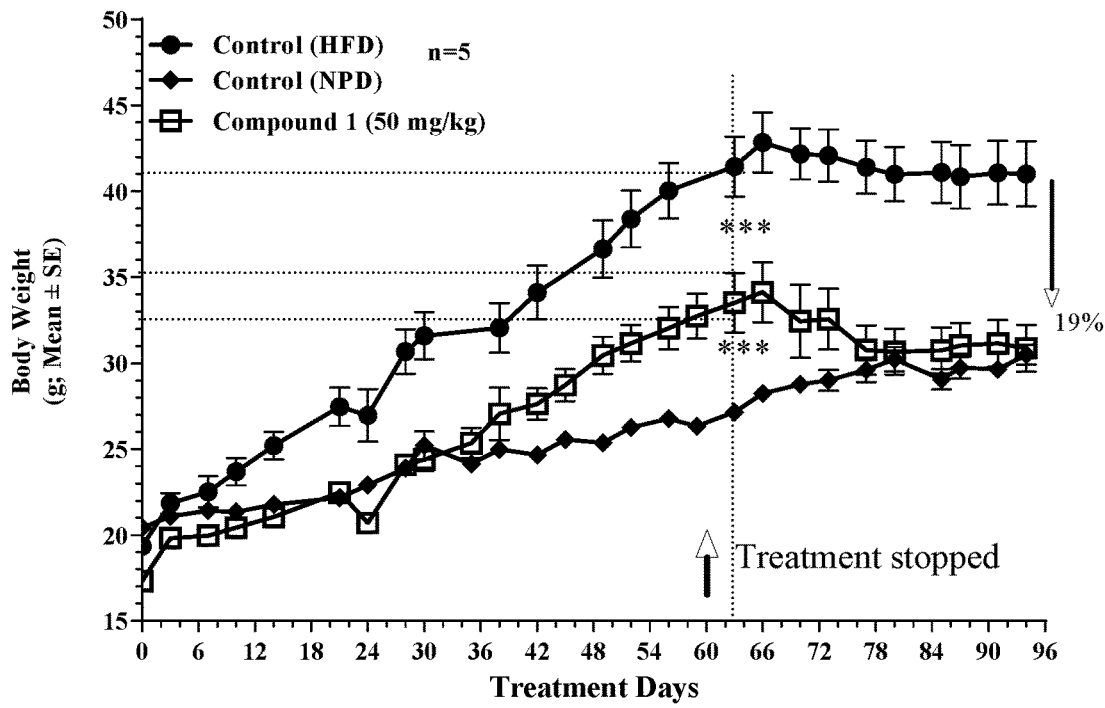
FIG. 5 shows that at the end of the drug treatment period, the group of mice treated with compound 1 showed a significant (P<0.0001) decrease in body weight by 19%, compared with the high fat diet group. At the end of this period, where all mice were put on the normal diet, the group of mice which was treated with compound 1 showed a 17% decrease in body weight, compared with the control high fat diet group.
Figure 5B:
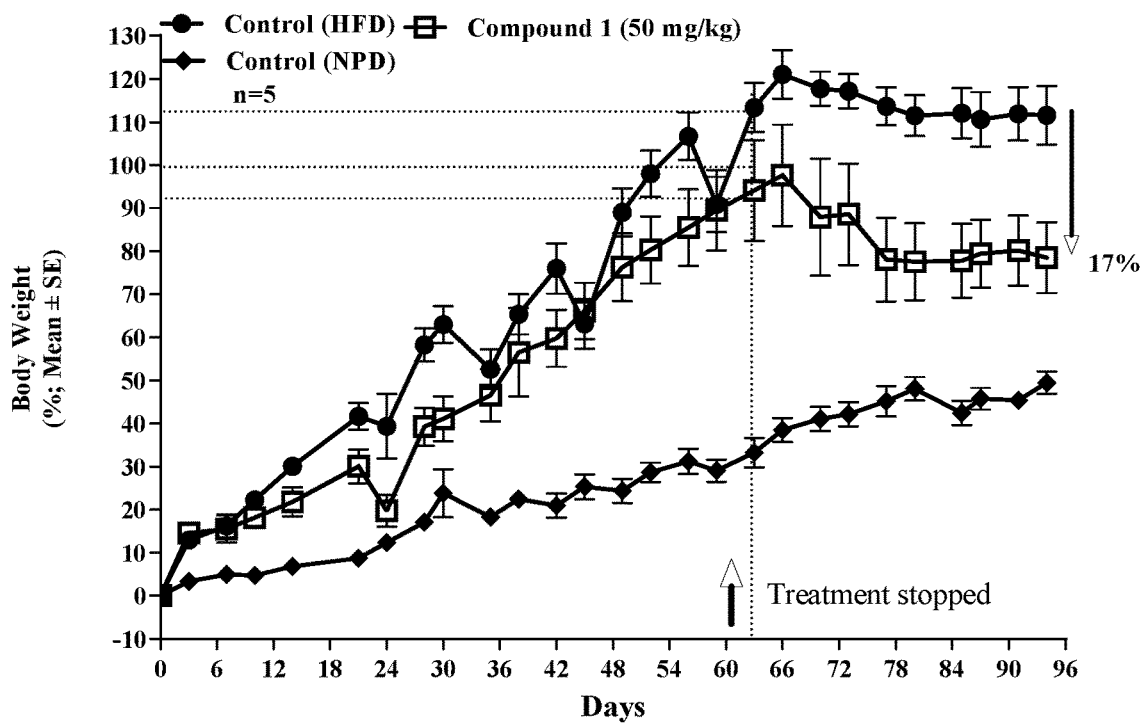
Figure 6A:
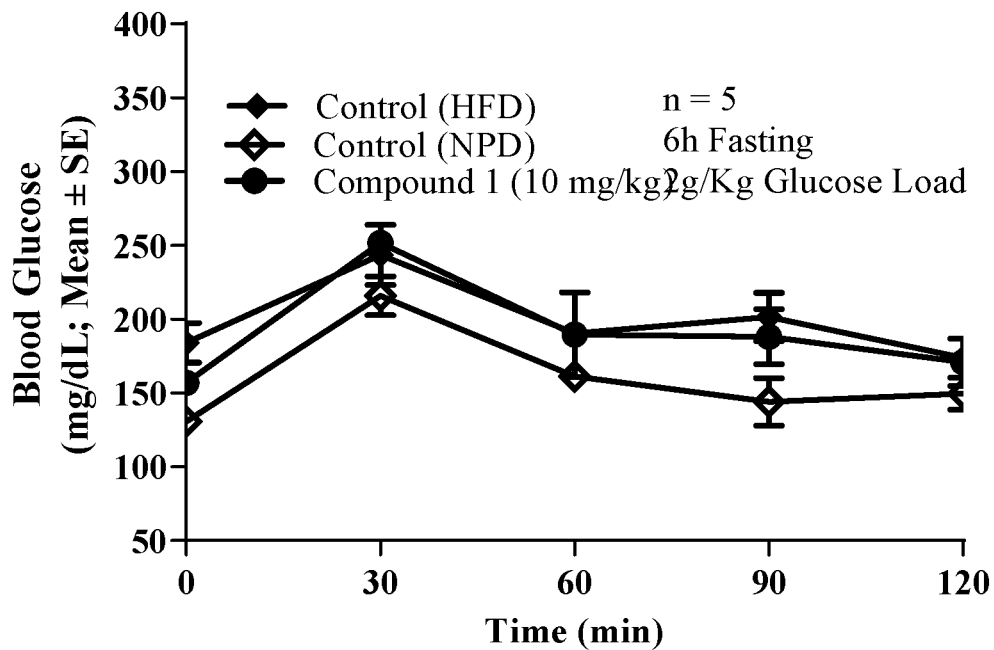
FIG. 6 shows that the group of mice treated with compound 1 showed 7% lower fasting blood glucose compared with the Control high fat diet group of mice (FIG. 6A). At the end of 120 minutes in the oral glucose tolerance test, the group of mice administered with compound 1 showed a 17% decrease in blood glucose compared with the Control high fat diet group (FIG. 6B).
Figure 6B:
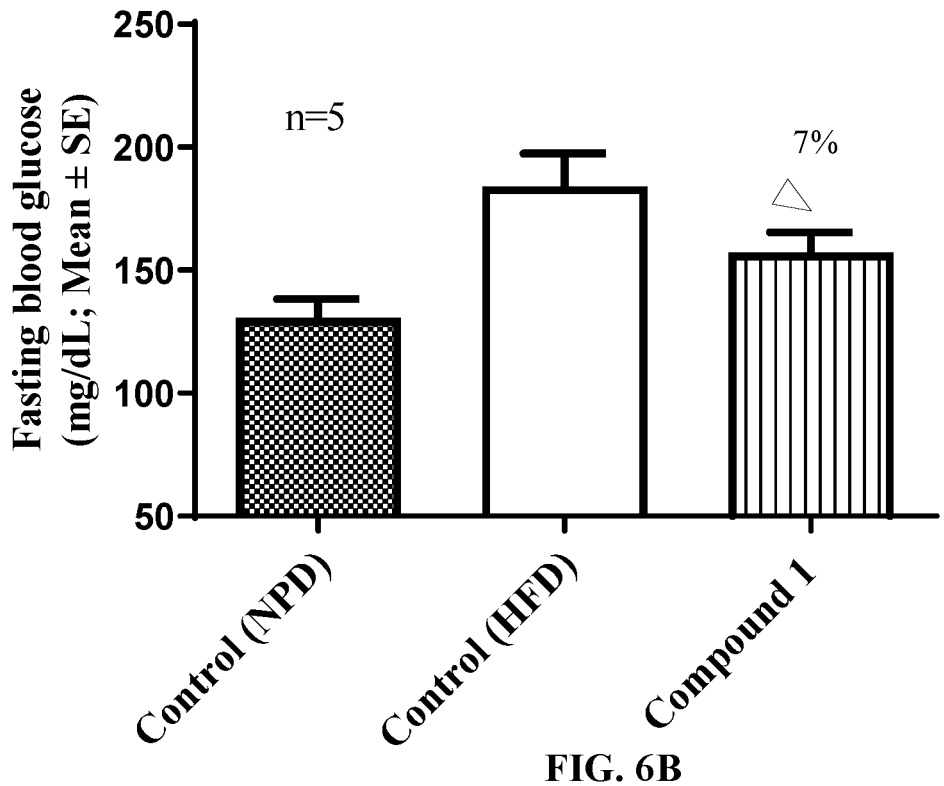
Figure 7:
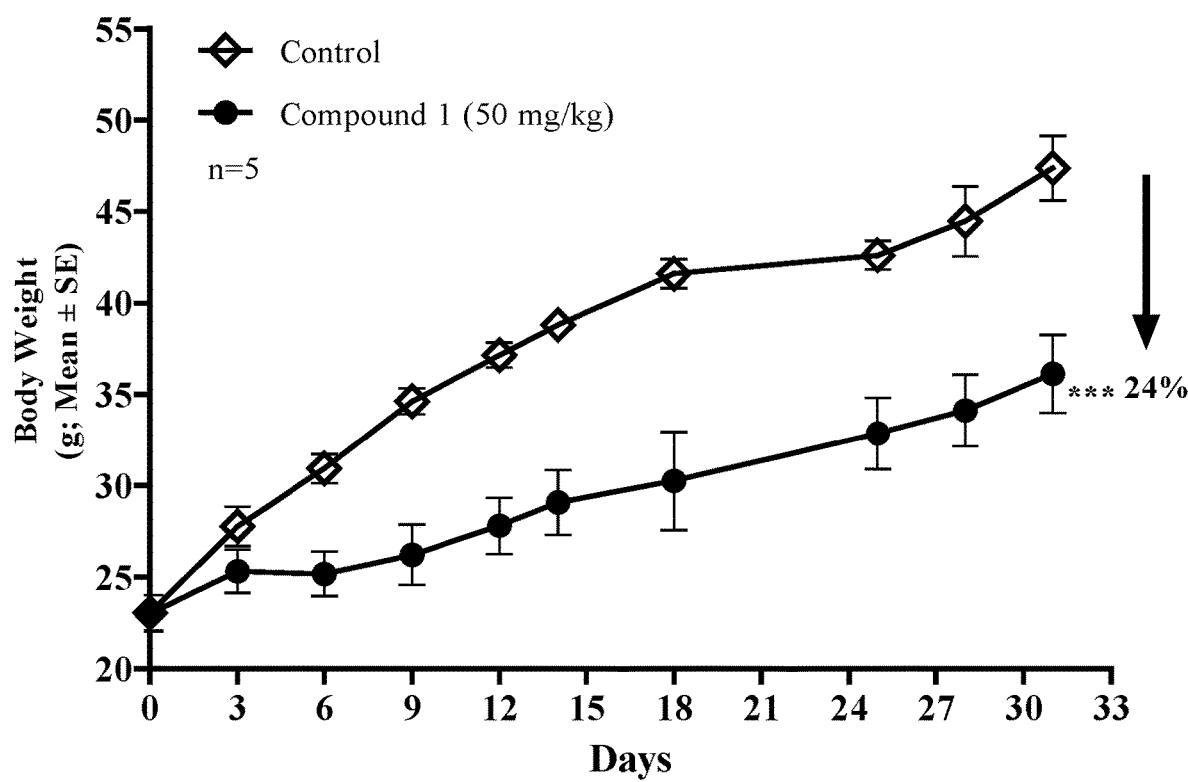
FIG. 7 shows that mice treated with compound 1 showed significant reduction (P<0.0001) by 24% in body weight compared with the untreated group of mice starting from day 6 till the entire duration of the study.
Figure 8:
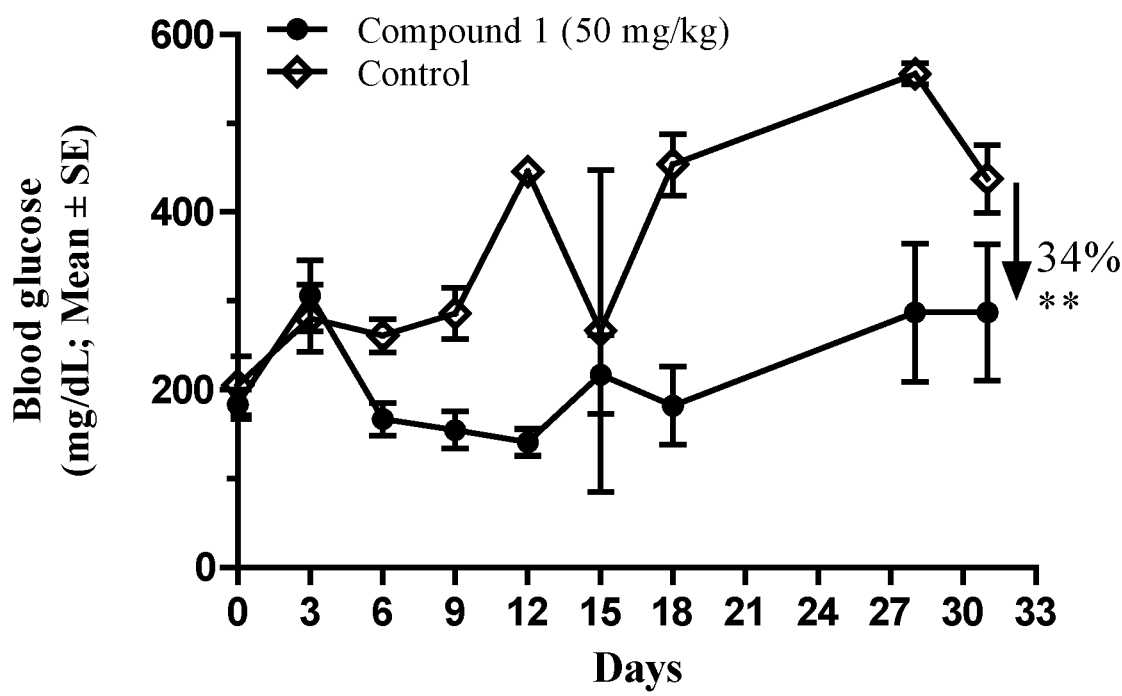
FIG. 8 shows that mice treated with compound 1 showed significant reduction (P<0.003) by 34% in blood glucose compared with the untreated group of mice starting from day 6 till the entire duration of the study.
Figure 9A:
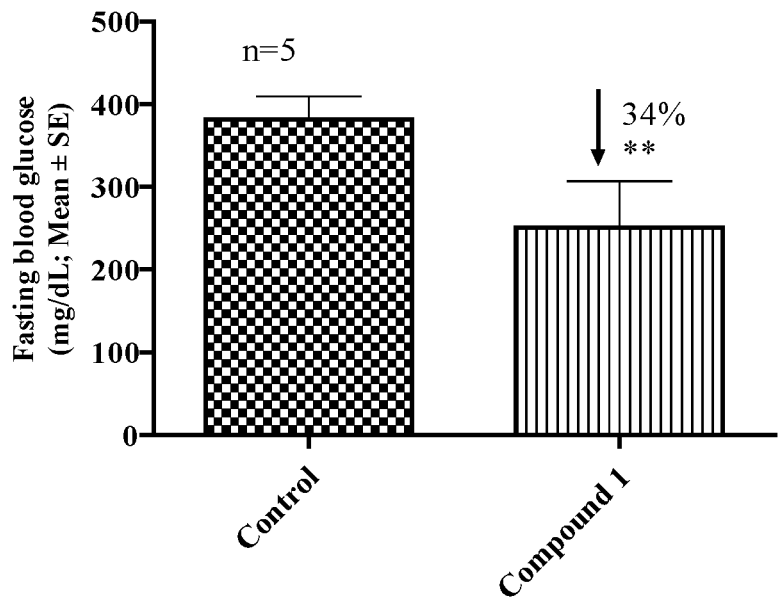
FIG. 9 shows that at the end of the study duration of 30 days, mice treated with compound 1 showed significant reduction (P<0.003) by 34% in blood glucose compared with the untreated group of mice starting from day 6 till the entire duration of the study.
Figure 9B:
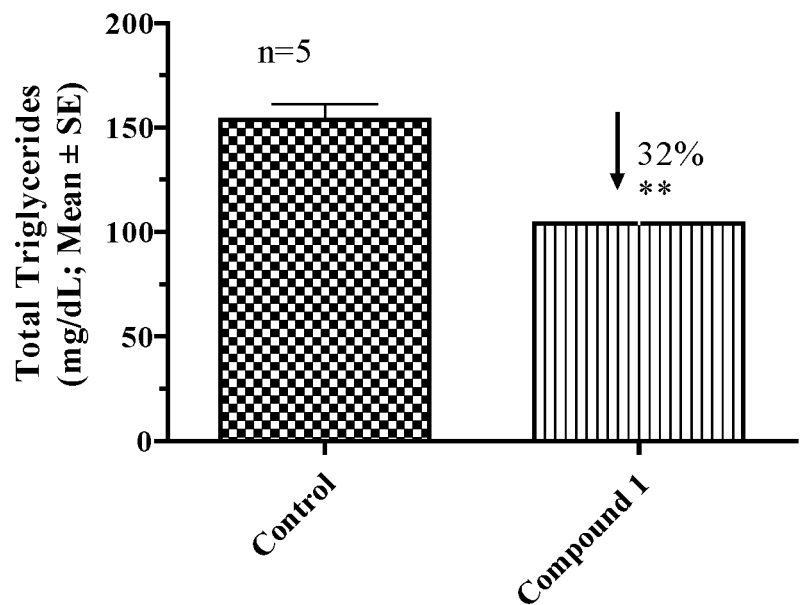
Figure 10A:
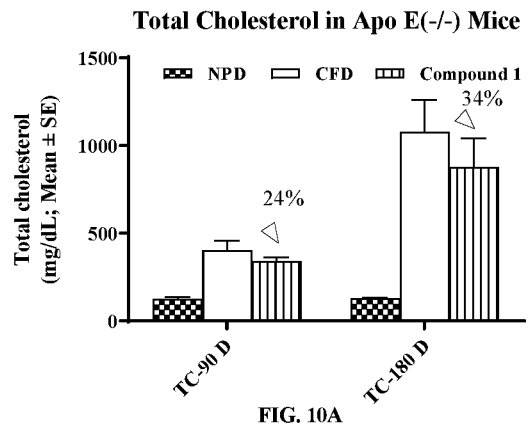
FIG. 10 shows that the group of mice administered with compound 1 showed a 24% decrease in Total Cholesterol on day 90 and 34% decrease in Total Cholesterol on day 180 from the control high fat diet group (FIG. 10A). The group of mice administered with compound 1 showed a 52% increase on day 90 and 62% increase on day 180 in high density lipoprotein (HDL) from the control high fat diet group (FIG. 10B). The group of mice administered with compound 1 showed a 32% decrease in low density lipoprotein (LDL) on day 90 from the control high fat diet group (FIG. 10C). The group of mice administered with compound 1 showed a 7% decrease on day 90 and 26% decrease on day 180 in Triglycerides from the control high fat diet group (FIG. 10D). The group of mice administered with compound 1 showed a 35% decrease on day 90 and 39% decrease on day 180 in blood glucose from the control high fat diet group (FIG. 10E).
Figure 10B:
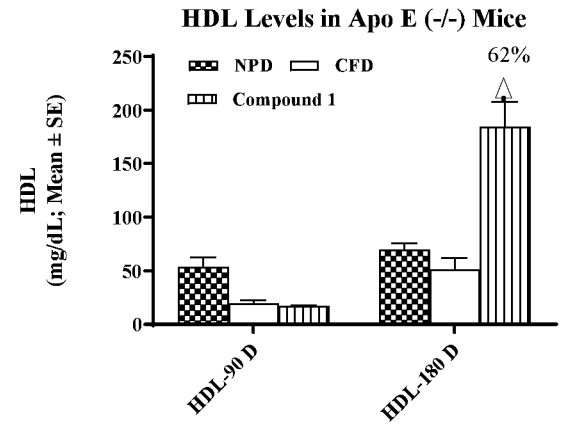
Figure 10C:
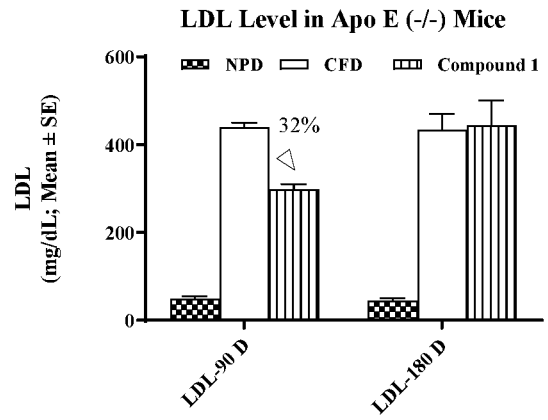
Figure 10D:
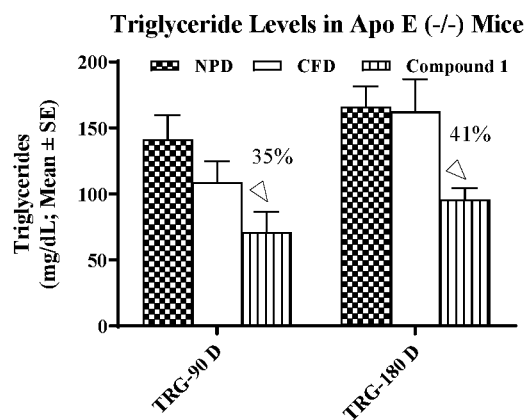
Figure 10E:
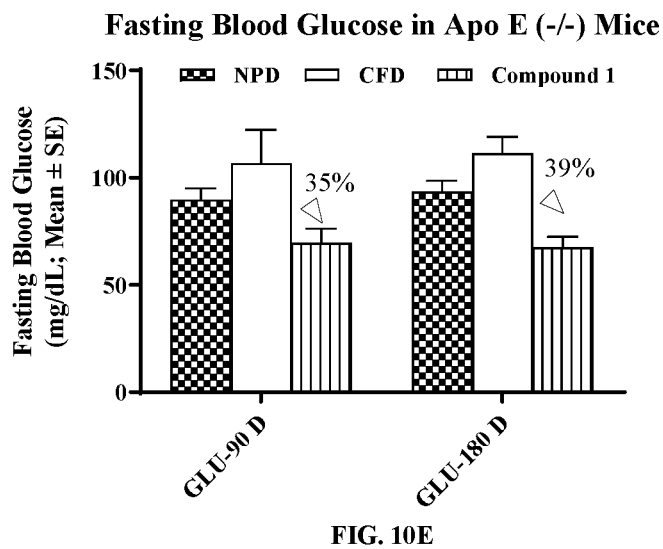
Figure 11A:
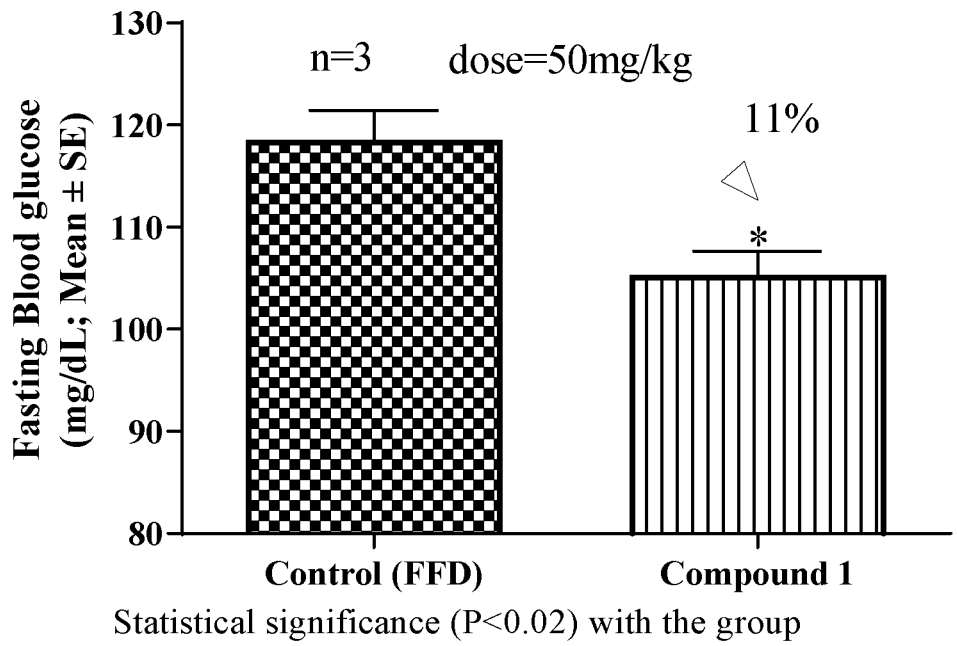
FIG. 11 shows that the group of rats treated with compound 1 showed a significant (P<0.002) decrease by 11% in fasting blood glucose than the vehicle group of rats on day 30 and a decrease by 9% on day 60, compared with the Control group of rats.
Figure 11B:
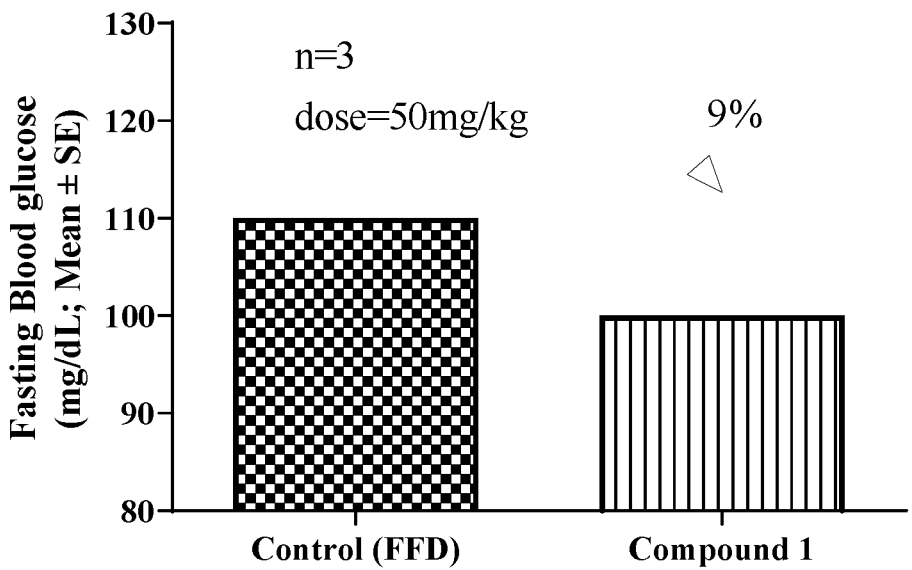
Figure 12:
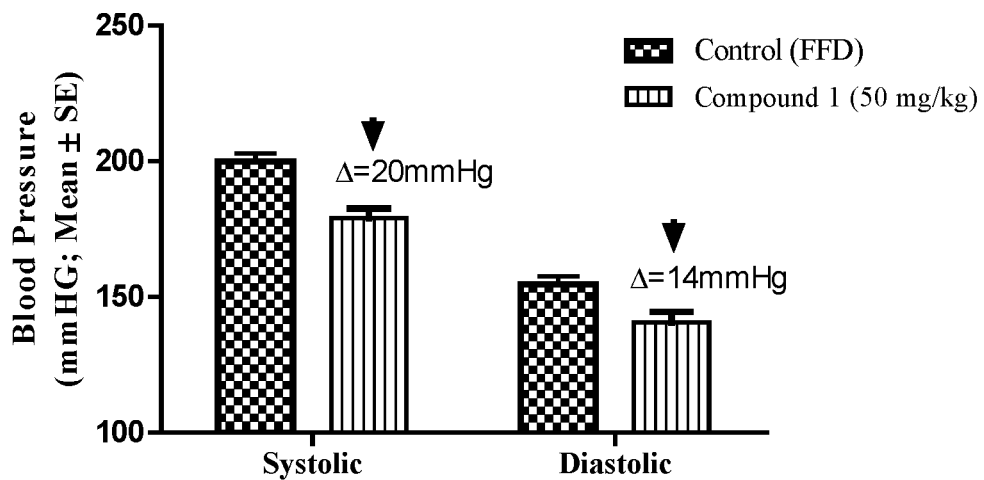
FIG. 12 shows that rats treated with compound 1 showed 10% decrease in systolic blood pressure and a 9% decrease in diastolic blood pressure, compared with the control group of rats.
Figure 13:
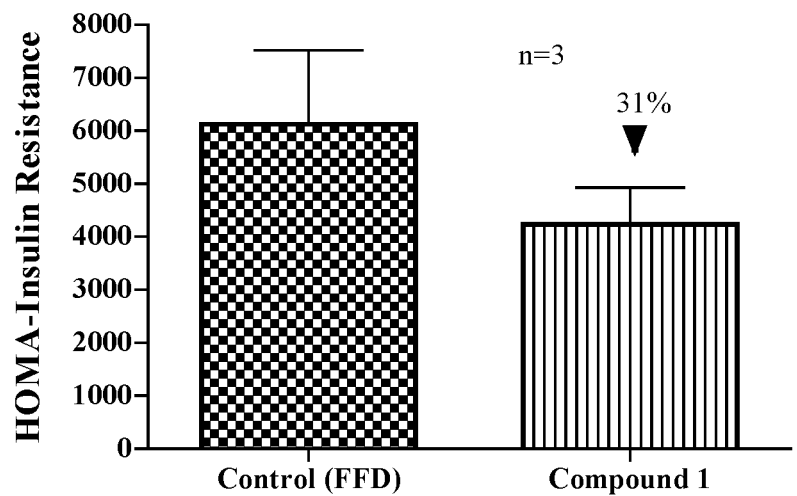
FIG. 13 shows that rats administered with compound 1 showed a 31% decrease in HOMA IR from the group of Control rats (FIG. 13A).
Figure 14A:
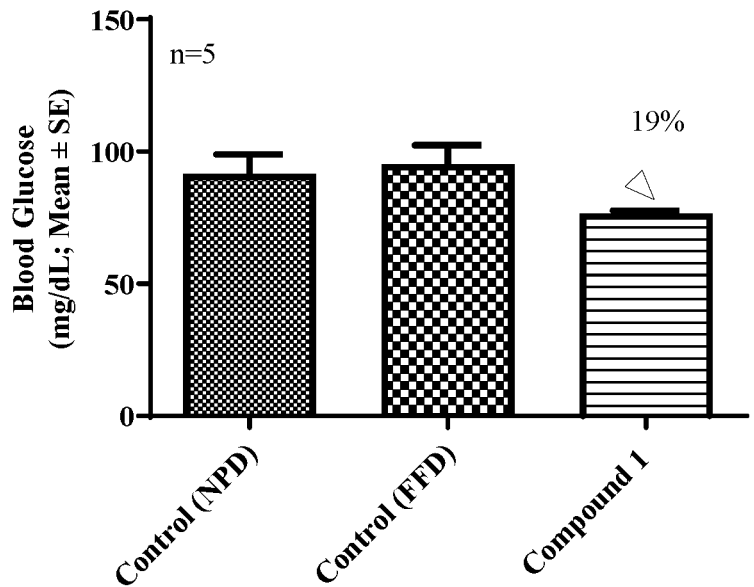
FIG. 14 shows that the group of hamsters administered with compound 1 showed a significant (P<0.03) reduction by 19% blood glucose, compared with the Control group of high fructose fed hamsters (FIG. 14A). Triglycerides were then measured in the plasma of the fasted hamsters. The group of hamsters treated with compound 1 showed a significant (p<0.0002) decrease by 55% in Triglycerides, compared with the Control group of high fructose fed hamsters (FIG. 14B).
Figure 14B:
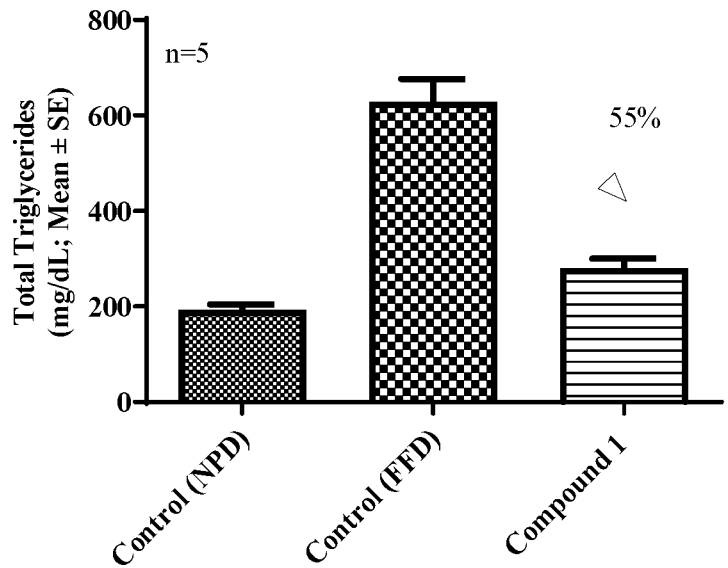
Figure 15A:
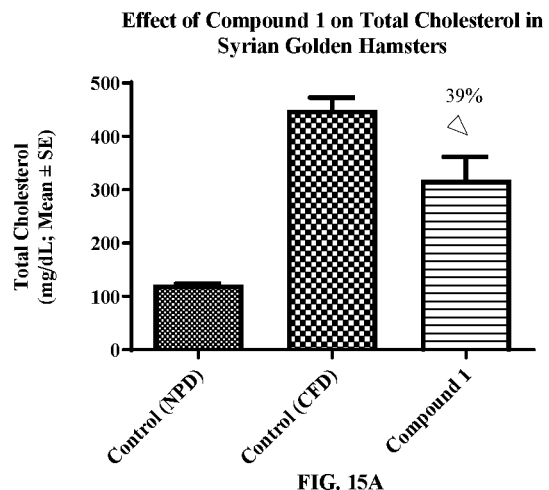
FIG. 15 shows that hamsters administered with compound 1 showed a 39% decrease in Total Cholesterol (FIG. 15A), a 35% increase in high-density lipoproteins (HDL) (FIG. 15B), a 34% decrease in low-density lipoproteins (LDL) (FIG. 15C), a 50% decrease in Triglycerides (FIG. 15D) and a 13% decrease in blood glucose (FIG. 15E) compared with the Control high cholesterol group.
Figure 15B:
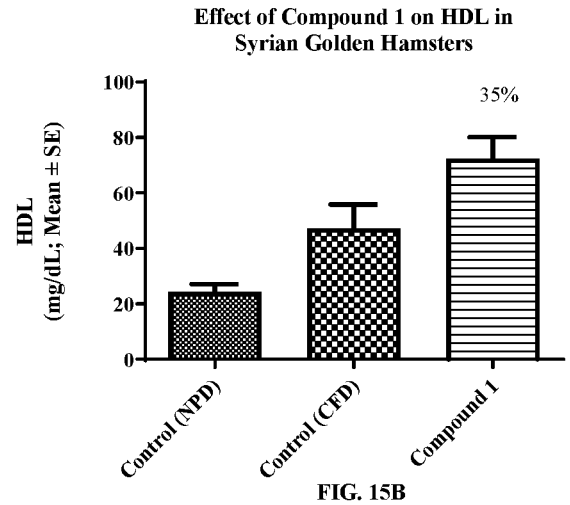
Figure 15C:
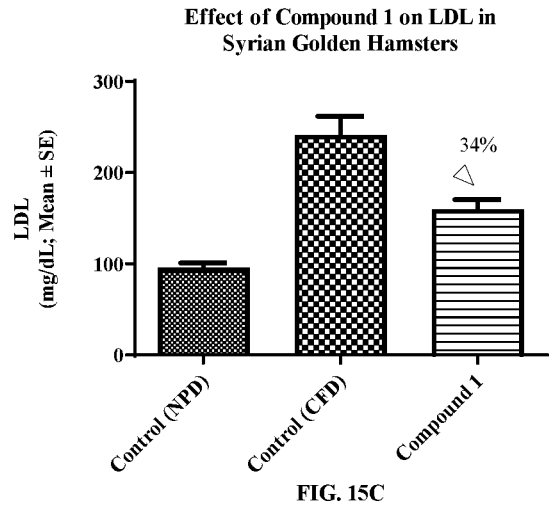
Figure 15D:
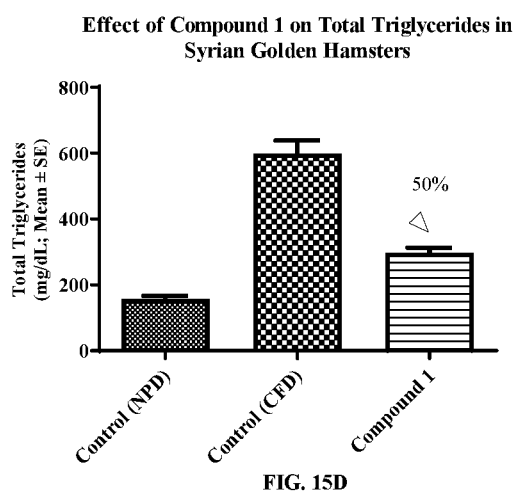
Figure 15E:
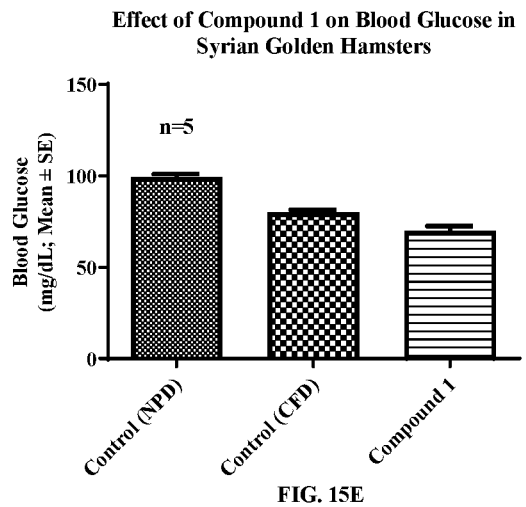
Figure 16:
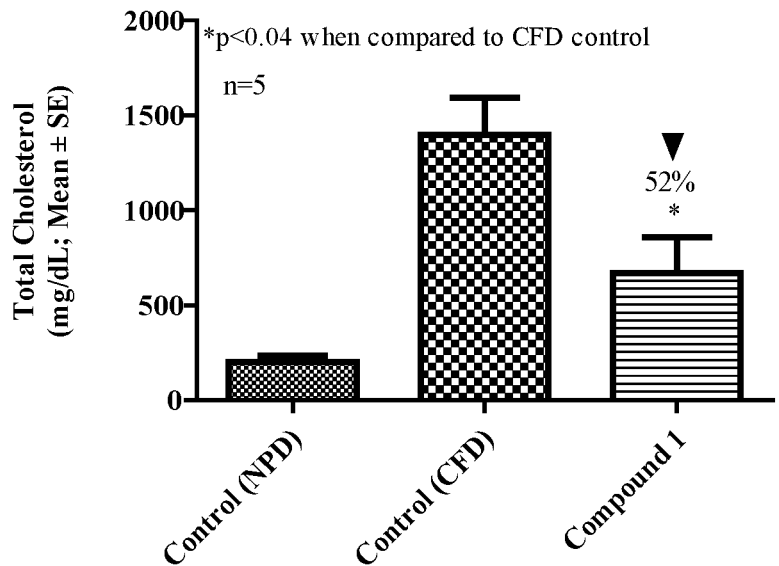
FIG. 16 shows hamsters treated with compound 1 showed a decrease by 20% in Total Cholesterol compared with the high cholesterol fed group.
Figure 17:
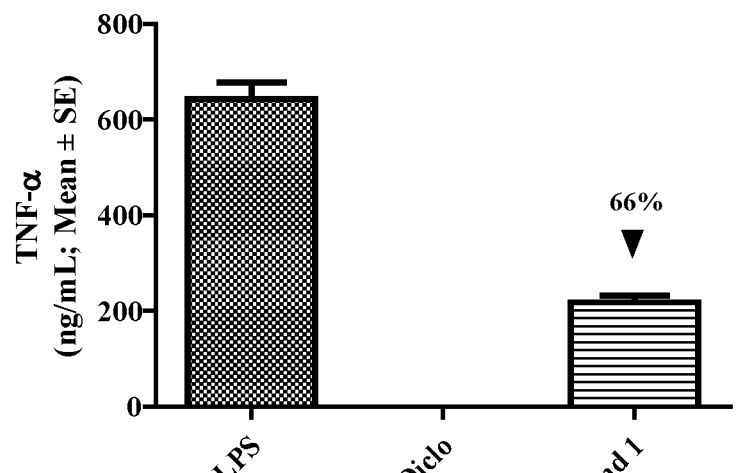
FIG. 17 shows that mice administered with compound 1 showed 66% decreases of TNF-α from the LPS group.
Figure 18A:
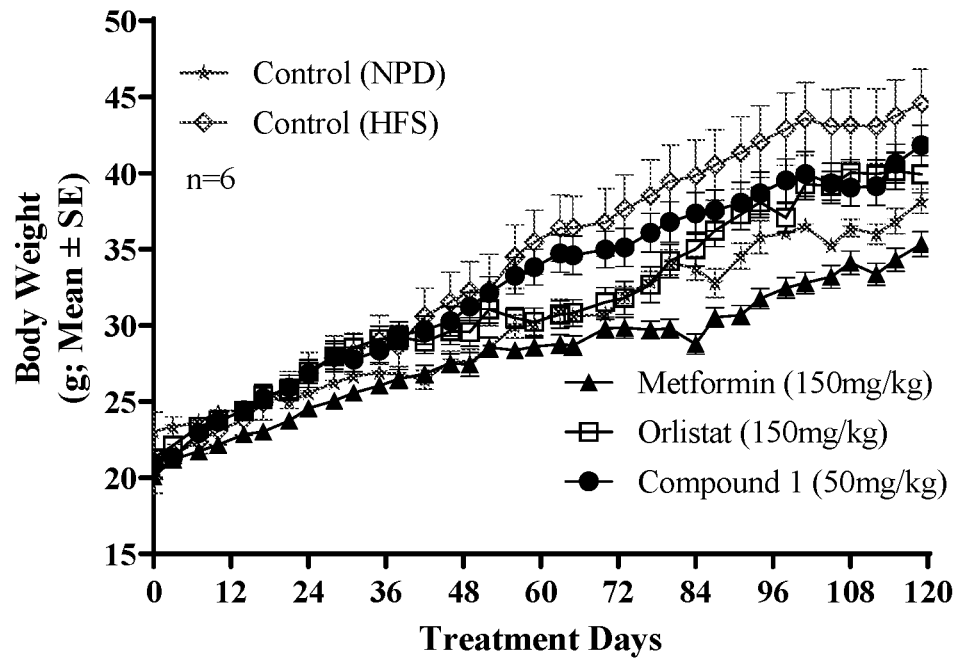
FIG. 18 shows that mice administered with compound 1 showed a significant (P<0.0001) decrease by 20% in body weight from the control high fat with sucrose group (FIG. 18B).
Figure 18B:
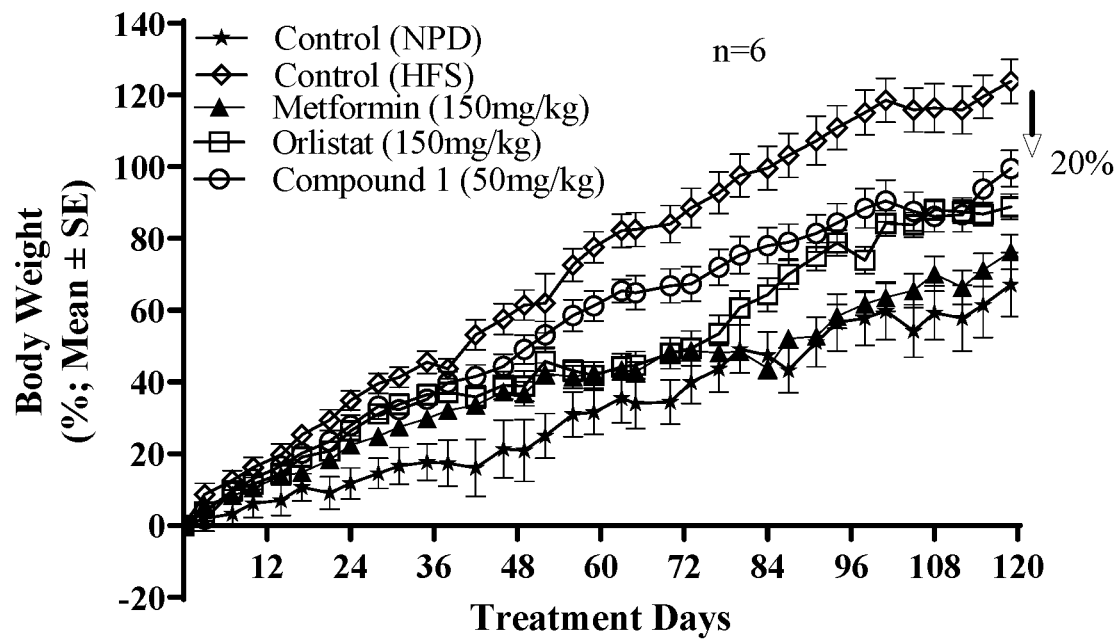
Figure 19:
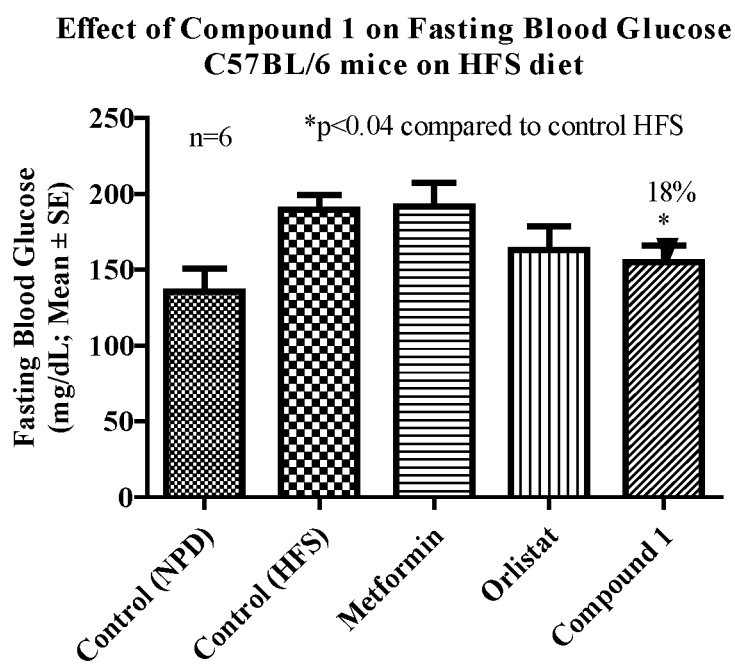
FIG. 19 shows that the group of mice administered with compound 1 showed a significant (P<0.04) decrease by 18% in fasting blood glucose from the control high fat with sucrose group.
Figure 20A:
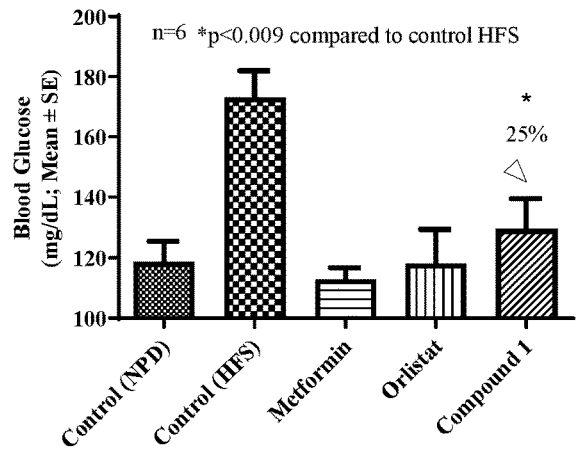
FIG. 20 shows that mice administered with compound 1 showed a significant (P<0.009) decrease by 25% in fasting blood glucose from the control high fat with sucrose group (FIG. 21A). An oral glucose tolerance test was conducted. For this test the mice were administered with glucose orally at 2 g/Kg. Blood glucose was measured at the fasted state (baseline, taken prior to glucose administration), then at 30, 60, 90 and 120 minutes (FIG. 20B). The group of mice treated with compound 1 showed significant (P<0.004) decrease by 28% in blood glucose at the peak time of 30 minutes (FIG. 20C).
Figure 20B:
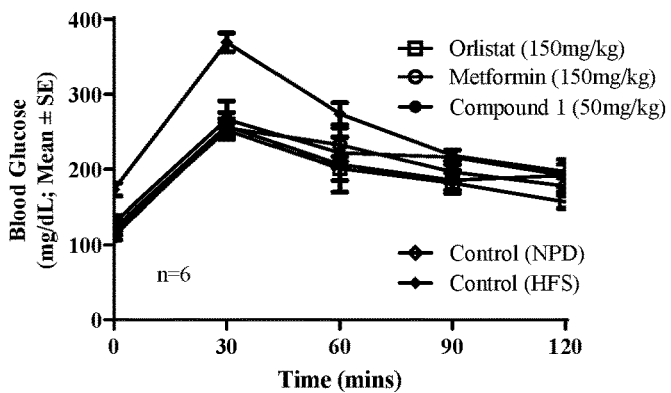
Figure 20C:
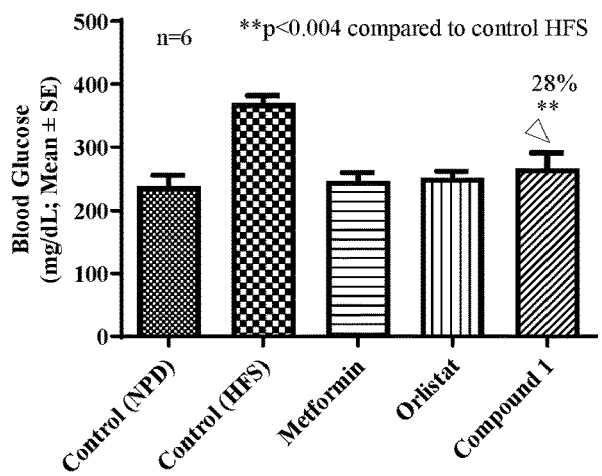
Figure 21:
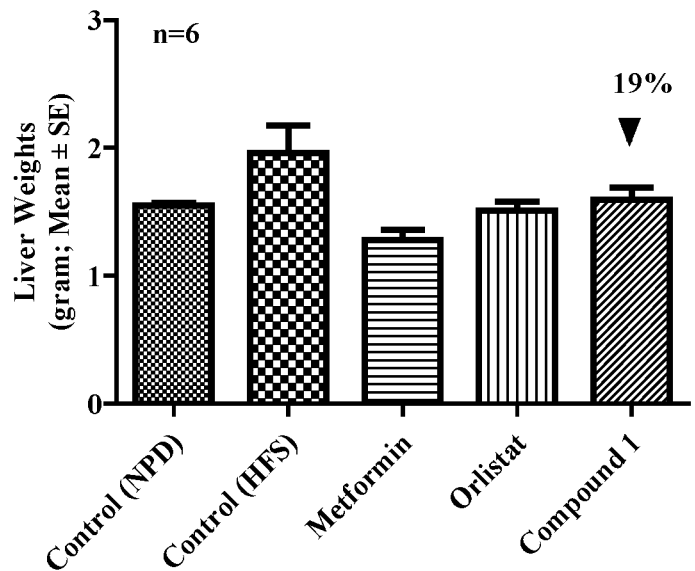
FIG. 21 shows that mice administered with compound 1 showed a 19% decrease in liver weight compared with the high fat with sucrose group.
Figure 22:
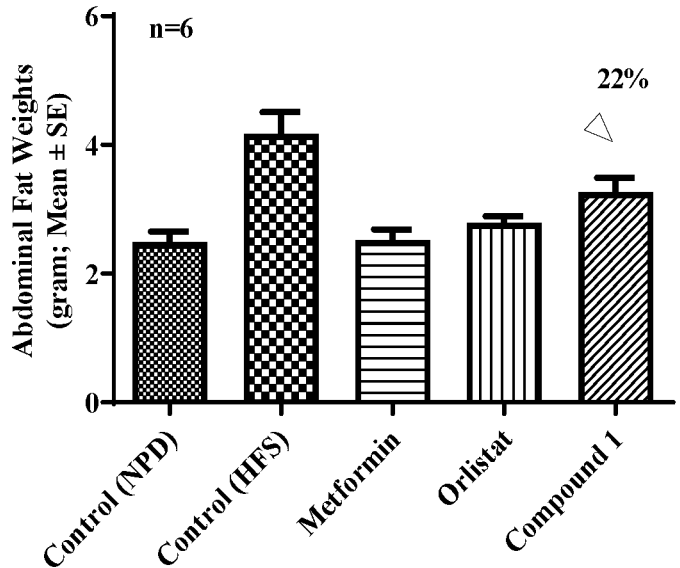
FIG. 22 shows that mice administered with compound 1 showed a 22% decrease in abdominal fat weight compared with the high fat with sucrose group.
Figure 23A:
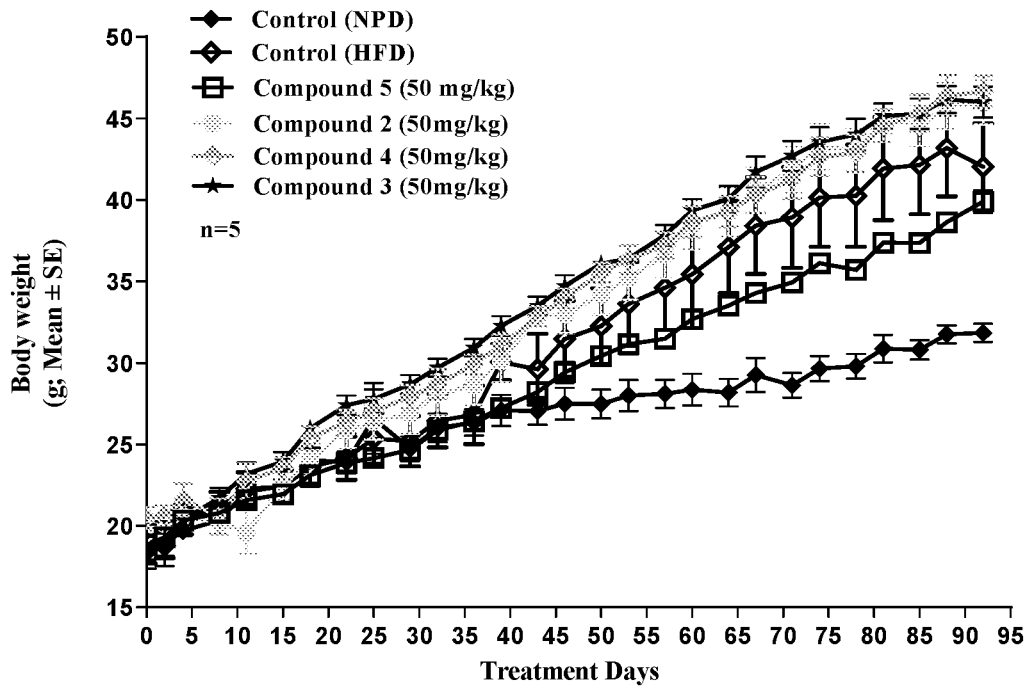
FIG. 23 shows that Mice treated with compound 5 showed an 11% decrease in body weight compared with the Control high fat diet group.
Figure 23B:
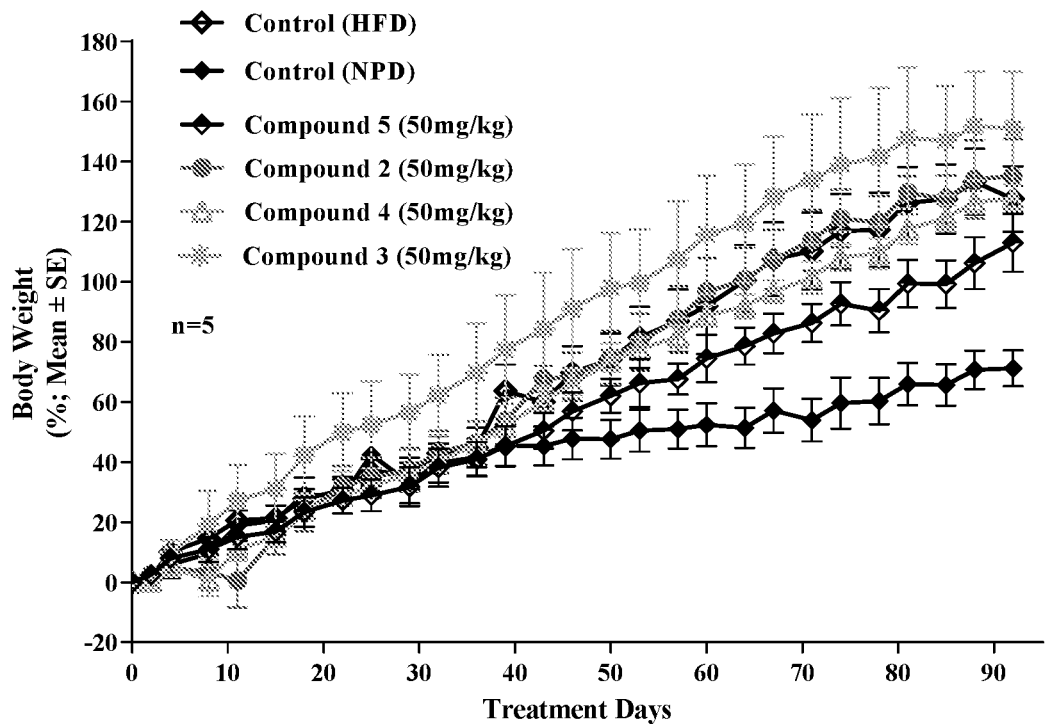
Figure 24A:
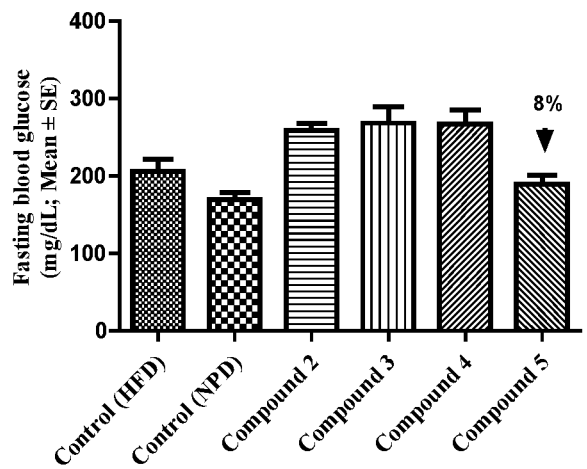
FIG. 24 shows that the group of mice administered with compound 5 showed an 8% decrease in fasting blood glucose, compared with the control high fat diet group. The group of mice treated with compound 5 showed significant (P<0.03) decrease by 32% in blood glucose at the peak time of 30 minutes compared with the control high fat diet group in the oral glucose tolerance test.
Figure 24B:
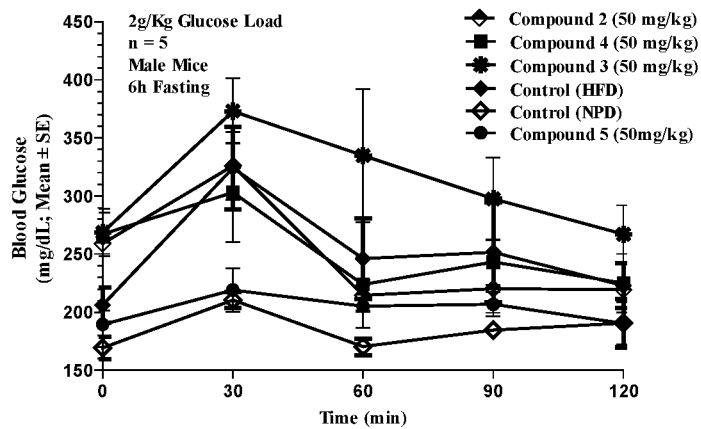
Figure 24C:
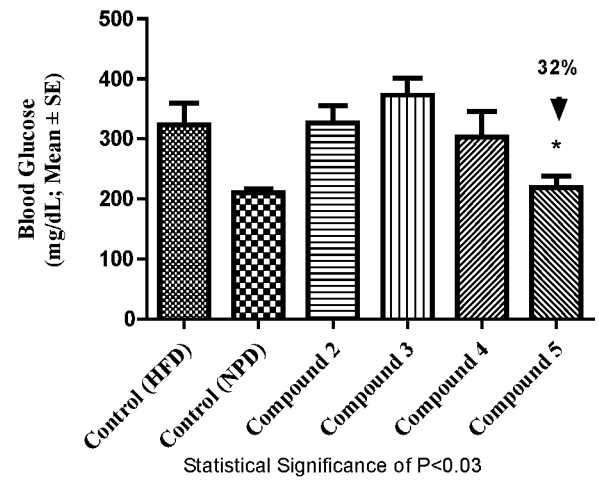
Figure 25A:
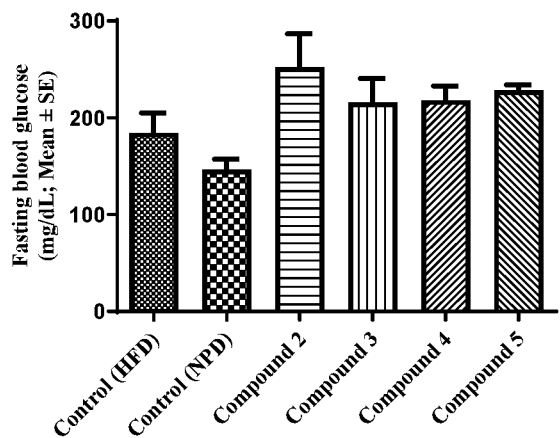
FIG. 25 shows that mice treated with COMPOUND 5 showed a decrease by 19% in blood glucose at the peak time of 30 minutes in the oral glucose tolerance test when compared with the control high fat diet group.
Figure 25B:
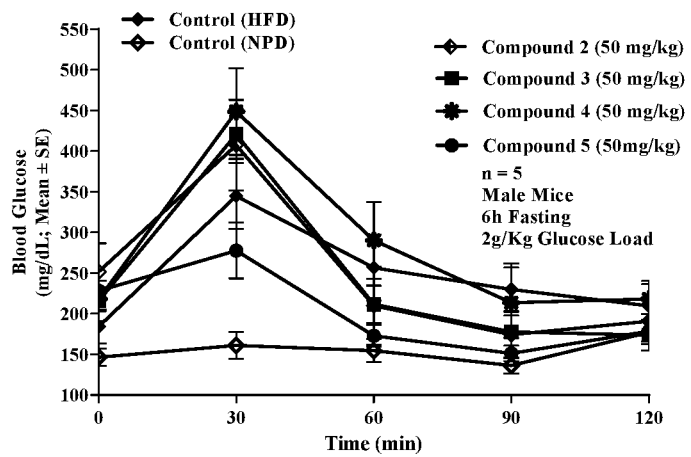
Figure 25C:
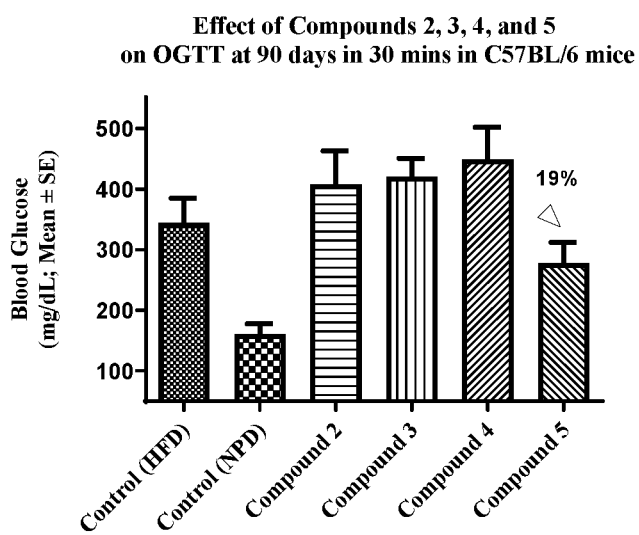
Figure 26:
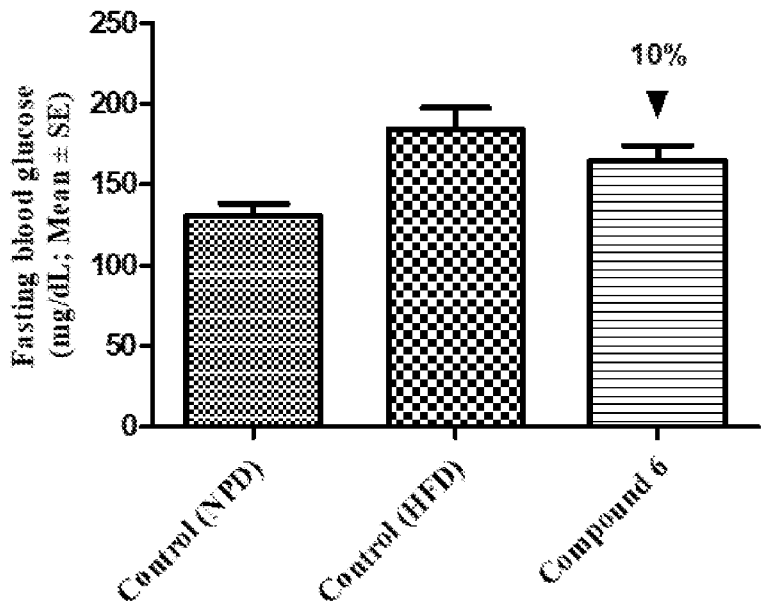
FIG. 26 shows that mice treated with COMPOUND 2 showed 10% reduction in fasting blood glucose on day 60 and an 11% decrease on day 90 compared with the control high fat diet group.
Figure 26:
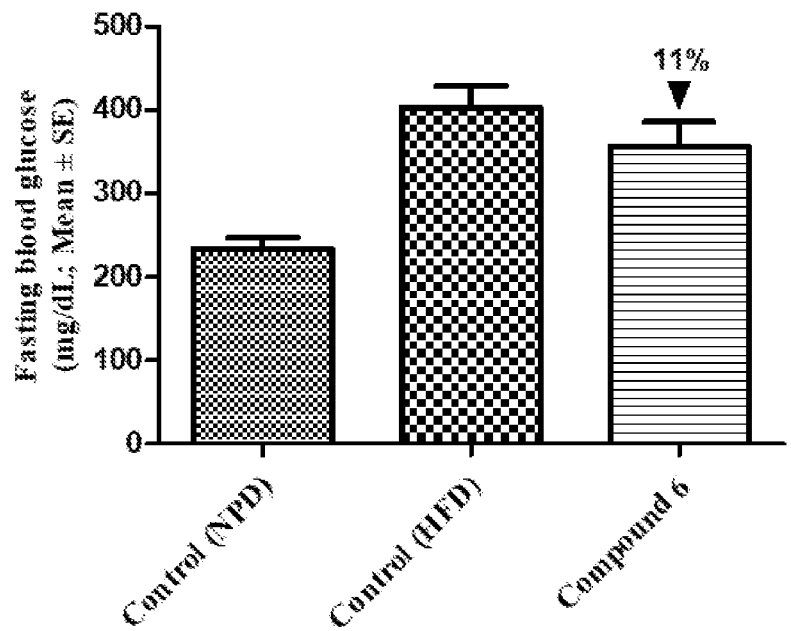
Figure 27:
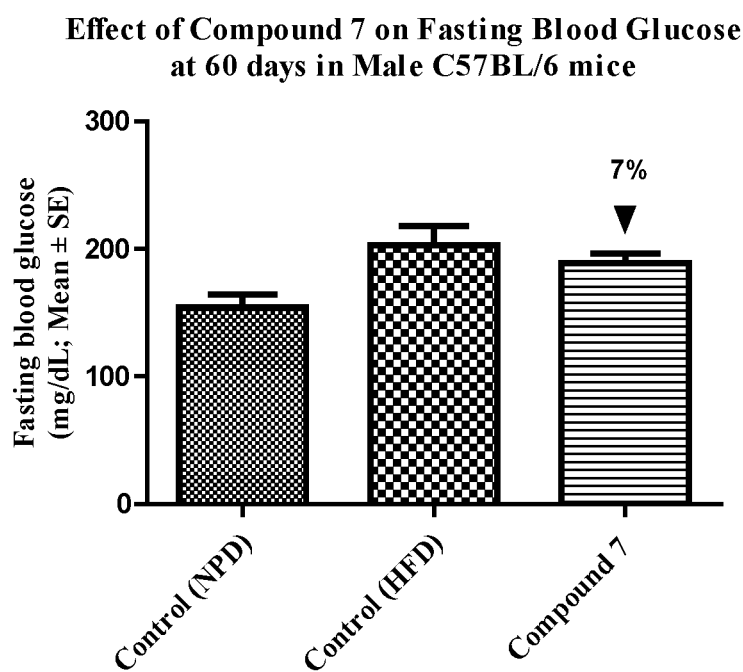
FIG. 27 shows that mice treated with COMPOUND 7 showed 7% reduction in fasting blood glucose on day 60 compared with the control high fat diet group.
Figure 28A:
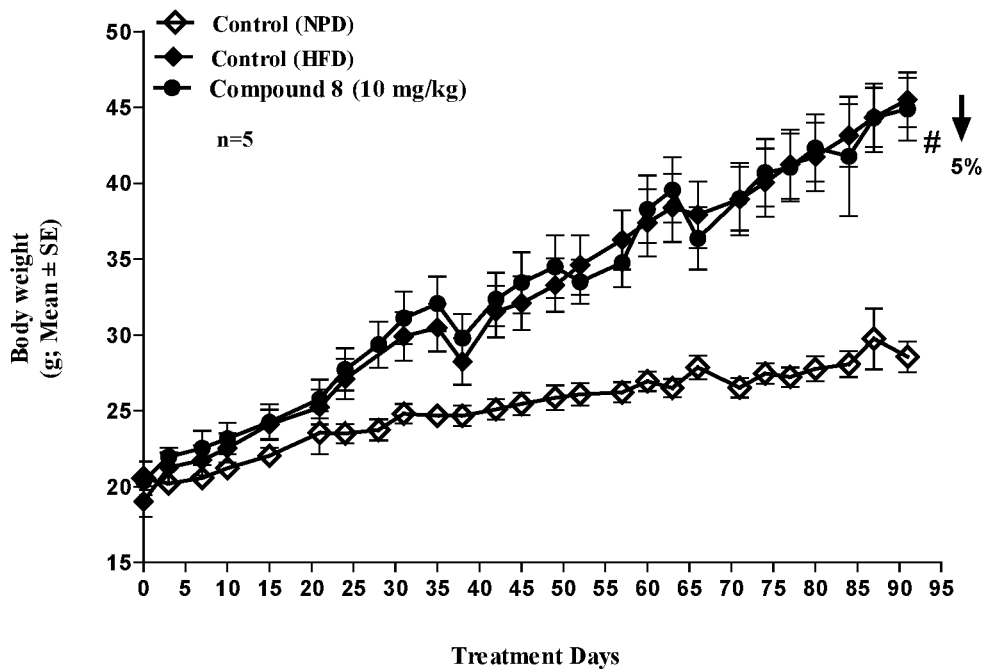
FIG. 28 shows that at the end of 90 days, the group of mice treated with COMPOUND 8 showed a significant (P<0.0001) decrease by 15% in body weight compared with the Control high fat diet group.
Figure 28B:
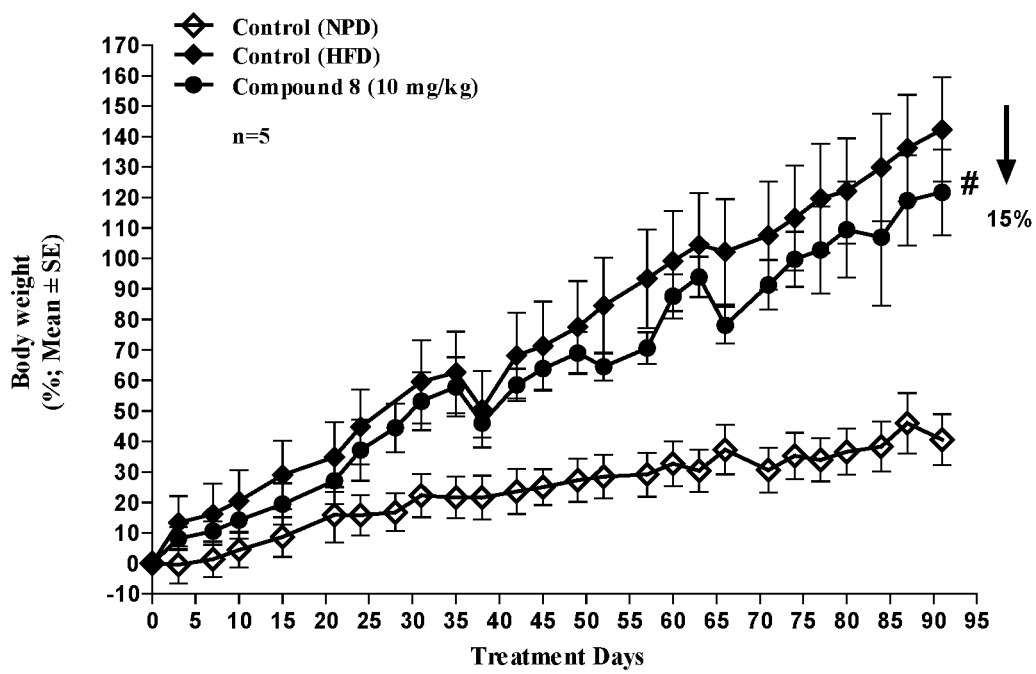
Figure 29A:
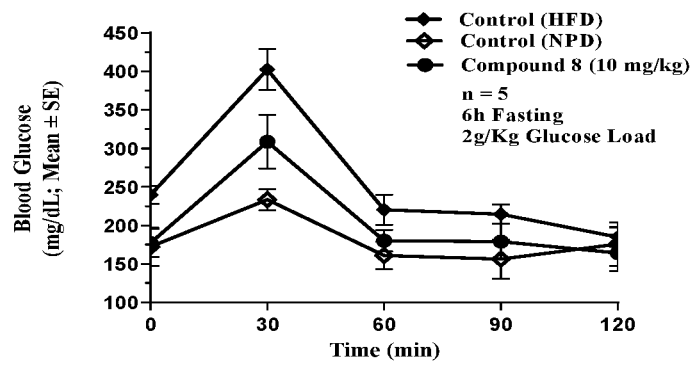
FIG. 29 shows that mice administered with COMPOUND 8 showed a significant (P<0.02) decrease by 26% in fasting blood glucose compared with the control high fat diet group (FIG. 29A). In the oral glucose tolerance test these mice also showed 23% reduction in blood glucose compared at the peak oral glucose tolerance test of 30 minutes compared with the control high fat diet group (FIG. 29C).
Figure 29B:
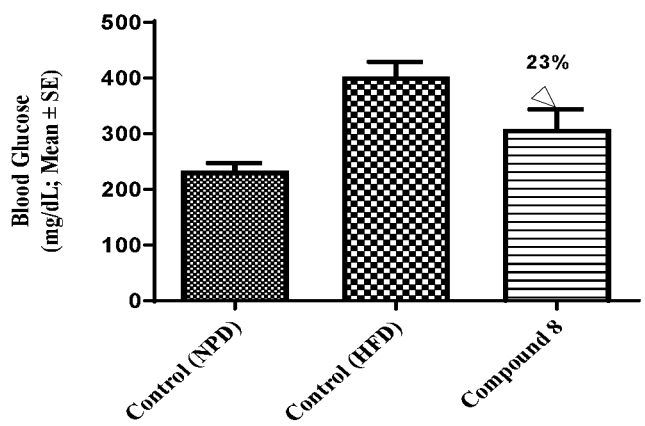
Figure 29C:
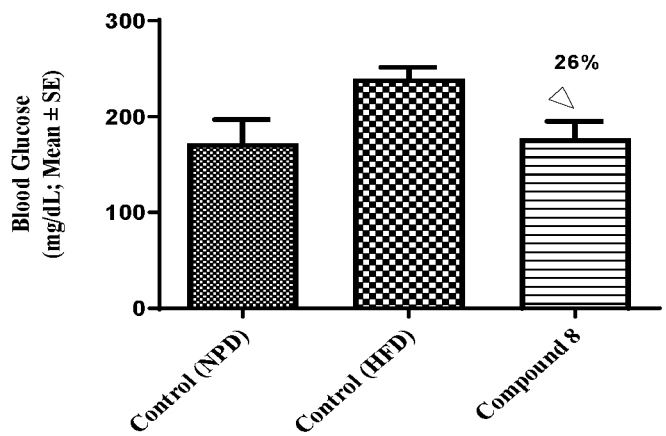
Figure 30:
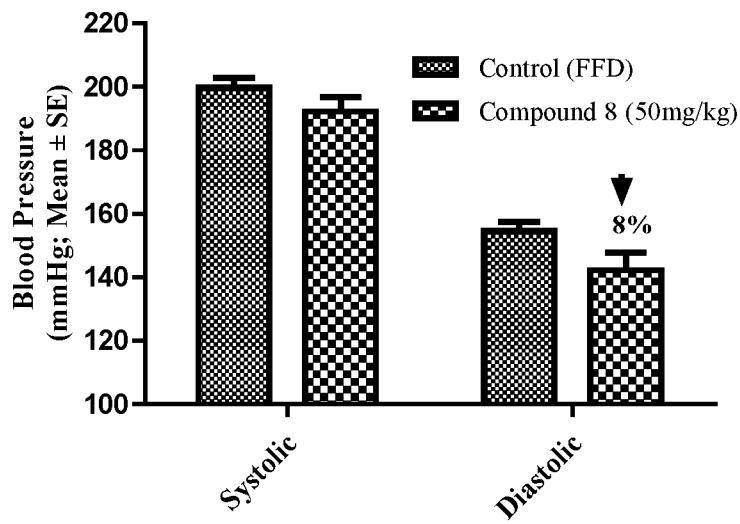
FIG. 30 shows that rats treated with COMPOUND 8 showed 4% decrease in systolic blood pressure and 8% decrease in diastolic blood pressure, then the vehicle group.
Figure 31:
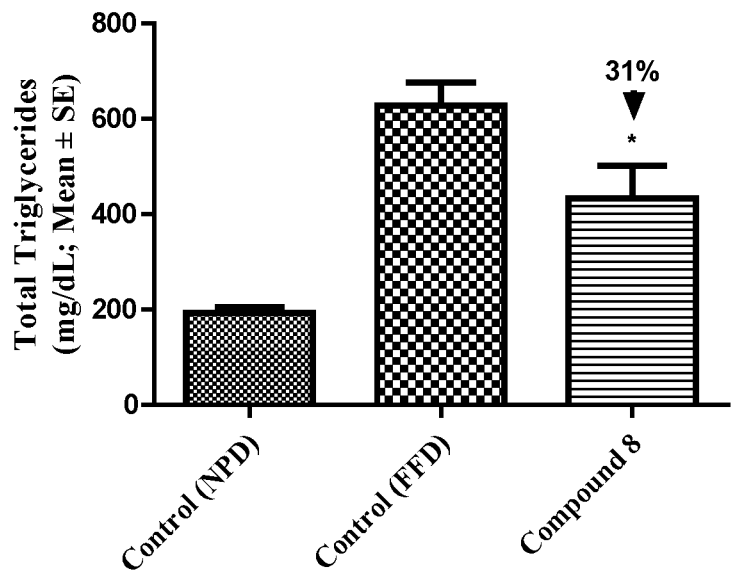
FIG. 31 shows that hamsters treated with COMPOUND 8 showed a significant decrease (P<0.05) by 31% in triglycerides compared with the high fructose fed group.
Figure 32:
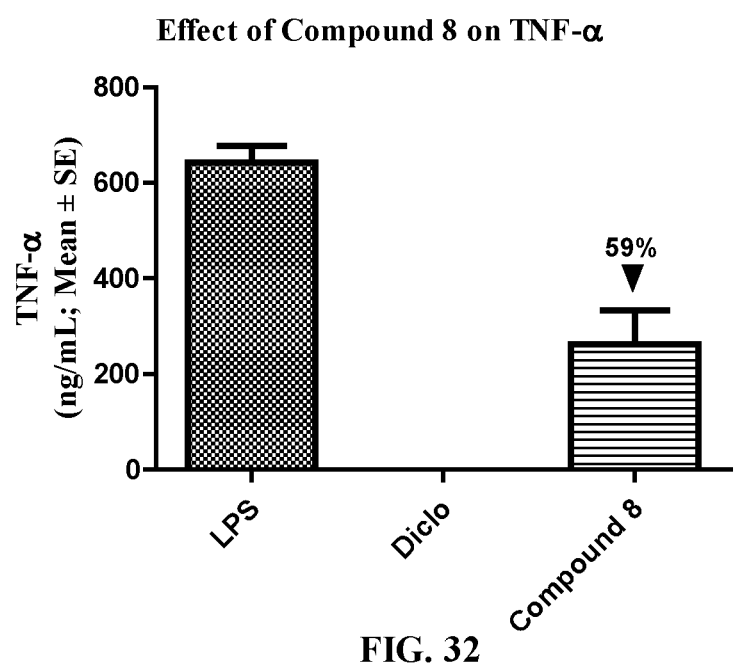
FIG. 32 shows that mice administered with COMPOUND 8 showed a 59% decrease of TNF-α from the LPS group.
Figure 33A:
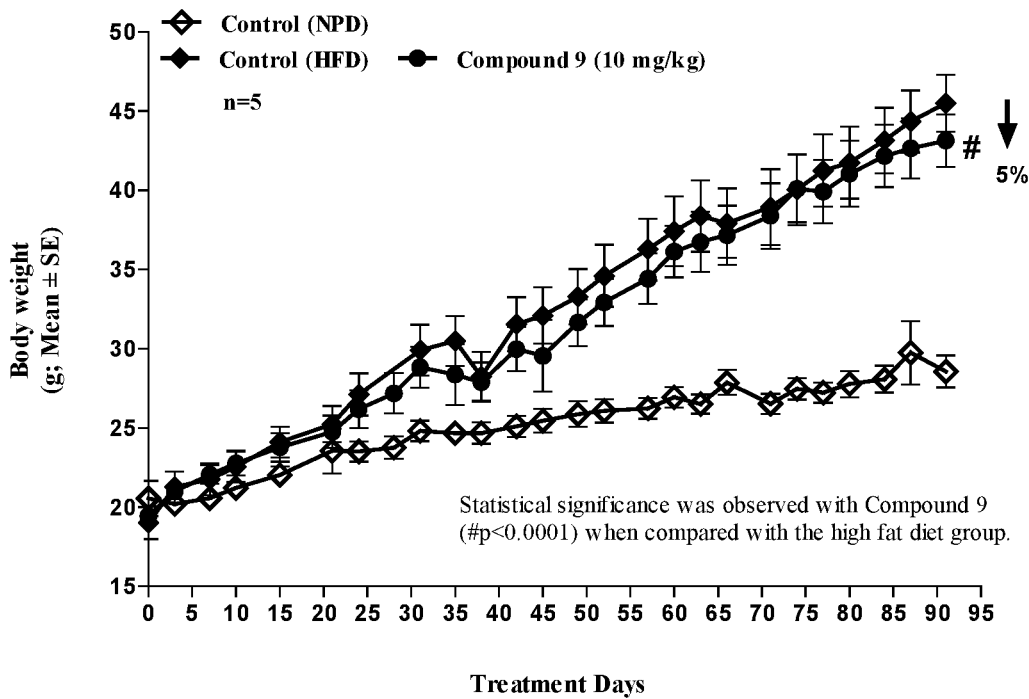
FIG. 33 shows mice treated with COMPOUND 9 showed a significant (P<0.0001) decrease by 15% in body weight when compared to the high fat diet control group.
Figure 33B:
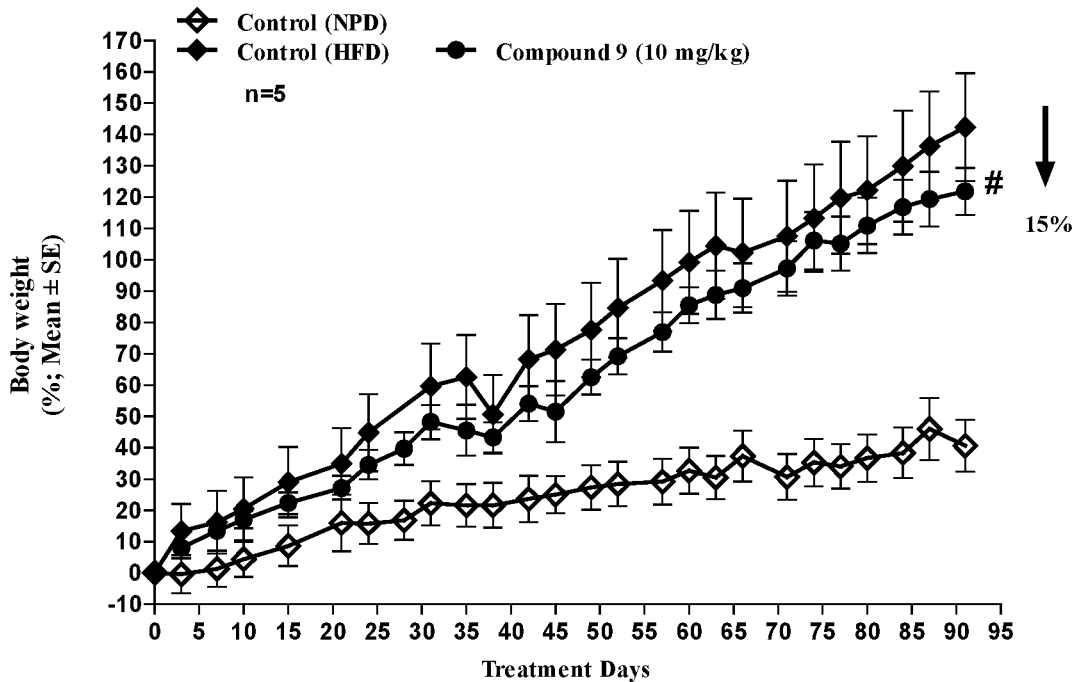
Figure 34A:
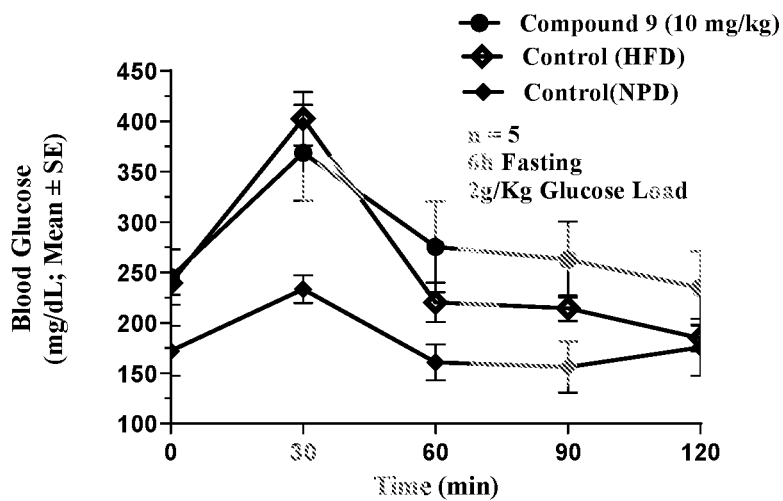
FIG. 34 shows that mice treated with COMPOUND 9 showed 8% reduction in blood glucose compared at the peak oral glucose tolerance test of 30 minutes compared with the control high fat diet group (FIG. 34B).
Figure 34B:
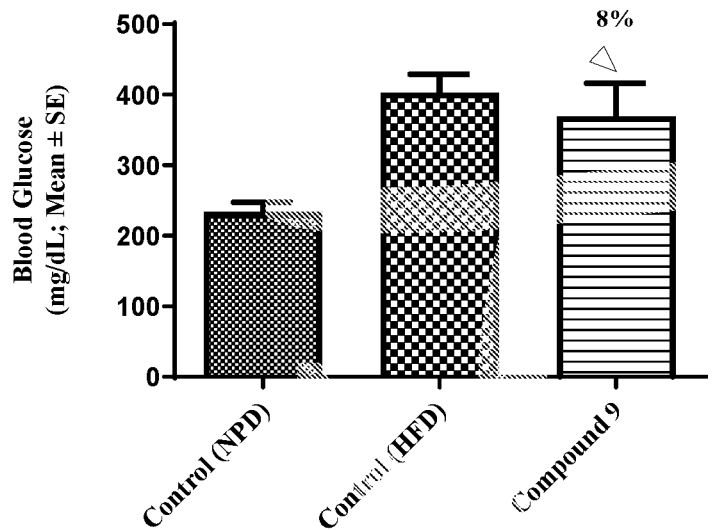

In an embodiment of the present invention, the groups represented as $R_1$, $R_2$, $R_3$, $R_4$ and $R_5$ on ring A are predominantly hydrogen.

In an embodiment of the present invention, the group represented by $R_7$ is a carbonyl group through which free amino group containing molecules can form condensates. $R_7$ can also be selected from groups such as ethanedithiol and propanedithiol.

In an embodiment of the present invention, the styryl ring represented as ring A can contain one or multiple side chain substituents ranging from hydrogen, phenoxy, amino, sulphonyl, substituted, unsubstituted, straight chain or branched alkyls derivatives, halogens, and the like. This also defines the range of substituents accommodated by $R_1$, $R_2$, $R_3$, $R_4$ and $R_8$.

In an embodiment of the present invention, the groups represented by $R_6$ and $R_8$ on ring B can be selected from hydrogen, Hydroxy, alkoxy and branched or unbranched alkyl derivatives.

In an embodiment of the present invention, the groups represented by X and Y on ring B can be selected from hydrogen or Halogens like fluorine, chlorine, bromine, and iodine.

Pharmaceutically acceptable salts forming part of this invention include base addition salts such as alkali metal salts like Li, Na, and K salts, alkaline earth metal salts like Ca and Mg salts, salts of organic bases such as lysine, arginine, guanidine, diethanolamine, chlorine and the like, ammonium or substituted ammonium salts. Salts may include acid addition salts which are sulphates, nitrates, phosphates, perchlorates, borates, hydrohalides, acetates, tartarates, maleates, citrates, succinates, palmoates, methanesulphonates, benzoates, ascorbates, glycerophosphates, ketoglutarates and the like. Pharmaceutically acceptable solvates may be hydrates or comprising other solvents of crystallization such as alcohols.

More preferably, the present innovation relates to novel Styryl Carboxylate compounds of formula (I),

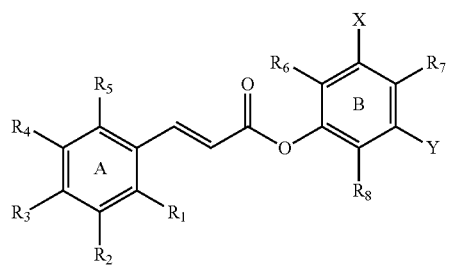

their derivatives, their analogs, their tautomeric forms, their stereoisomers, their polymorphs, their pharmaceutically acceptable salts, their pharmaceutically acceptable solvates, novel intermediates and pharmaceutical compositions containing them, wherein, the groups represented as $R_6$ and $R_8$, in the ring B are selected from hydrogen and alkoxy derivatives. The group represented by $R_7$ on ring B will be a carbonyl group which forms Schiff bases with compounds having a free amino group and forms thioketalization with compounds like ethanedithiol and propandithiol. The benzene ring represented as Ring A can contain substituents represented by $R_1$, $R_2$, $R_3$, $R_4$ and $R_5$ that are selected from linear or branched, substituted or unsubstituted ($C_1$ to $C_{12}$) alkyl groups such as methyl, ethyl, propyl, isopropyl, n-butyl, isobutyl, t-butyl, pentyl, hexyl, octyl, nonyl and the like; substituted or unsubstituted ($C_1$-$C_{12}$) alkoxy group such as methoxy, ethoxy, propoxy, butoxy and the like; hydroxyl group or extended chain through an alkyloxy ester or un-substituted or substituted aryloxy ester groups; amines, sulphonyl, halogens and the like. The groups represented by X and Y on ring B are preferentially selected from hydrogen and Halogens like fluorine, chlorine, bromine and iodine.

The formula of the useful compounds synthesized in this present are listed below.

3-Phenyl-acrylic acid 4-(hydroxyimino-methyl)-phenyl ester (C1). 4-((E)-ureidomethyl)phenyl cinnamate (C2)

4-(1,3-dithian-2-yl)phenyl cinnamate (C3) 3-Phenyl-acrylic acid 4-benzylidineamino-3'-hydroxyaniline-2-methoxyphenyl ester (C4)

4-((E)-(hydroxyimino)methyl)-2-methoxyphenyl cinnamate (C5)

(E)-ethyl 4-(4-(cinnamoyloxy)-3-methoxyphenyl)-6-methyl-2-oxo-1,2,3,4-tetrahydropyrimidine-5-carboxylate (C6)

(E)-ethyl 4-(4-(cinnamoyloxy)phenyl)-6-methyl-2-oxo-1,2,3,4-tetrahydropyrimidine-5-carboxylate (C7)

3-Phenyl-acrylic acid 4-(hydroxyimino-methyl)-2-methoxyphenyl ester (C8).

2-methoxy-4-((E)-ureidomethyl)phenyl cinnamate (C9)

4-[3-Methoxy-4-(3-phenyl-acryloyloxy)-phenyl]-6-Methyl-2-oxo-1,2,3,4-tetrahydro-pyrimidine-5-carboxylic acid ethyl ester (C10)
3-phenyl-acrylicacid4-[(2, 4-dinitro-phenyl)-hydrazonomethyl]-phenyl ester (C11)
4-formyl-2-methoxyphenyl cinnamate
2-chloro-4-formyl-6-methoxyphenyl cinnamate
2-bromo-4-formyl-6-methoxyphenyl cinnamate
4-formylphenyl cinnamate
(E)-4-formyl-2-methoxyphenyl 3-(3-chlorophenyl)acrylate
(E)-2-chloro-4-formyl-6-methoxyphenyl 3-(3-chlorophenyl)acrylate
(E)-2-bromo-4-formyl-6-methoxyphenyl 3-(3-chlorophenyl)acrylate
(E)-4-formylphenyl 3-(3-chlorophenyl)acrylate
(E)-4-formyl-2-methoxyphenyl 3-(3-bromophenyl)acrylate
(E)-2-chloro-4-formyl-6-methoxyphenyl 3-(3-bromophenyl)acrylate
(E)-2-bromo-4-formyl-6-methoxyphenyl 3-(3-bromophenyl)acrylate
(E)-4-formylphenyl 3-(3-bromophenyl)acrylate
(E)-4-formyl-2-methoxyphenyl 3-(3-methoxyphenyl)acrylate
(E)-2-chloro-4-formyl-6-methoxyphenyl 3-(3-methoxyphenyl)acrylate
(E)-2-bromo-4-formyl-6-methoxyphenyl 3-(3-methoxyphenyl)acrylate
(E)-4-formylphenyl 3-(3-methoxyphenyl)acrylate
(E)-4-formyl-2-methoxyphenyl 3-(4-chlorophenyl)acrylate
(E)-2-chloro-4-formyl-6-methoxyphenyl 3-(4-chlorophenyl)acrylate
(E)-2-bromo-4-formyl-6-methoxyphenyl 3-(4-chlorophenyl)acrylate
(E)-4-formylphenyl 3-(4-chlorophenyl)acrylate
(E)-4-formyl-2-methoxyphenyl 3-(4-bromophenyl)acrylate
(E)-2-chloro-4-formyl-6-methoxyphenyl 3-(4-bromophenyl)acrylate
(E)-2-bromo-4-formyl-6-methoxyphenyl 3-(4-bromophenyl)acrylate
(E)-4-formylphenyl 3-(4-bromophenyl)acrylate
(E)-4-formyl-2-methoxyphenyl 3-(4-methoxyphenyl)acrylate
(E)-2-chloro-4-formyl-6-methoxyphenyl 3-(4-methoxyphenyl)acrylate
(E)-2-bromo-4-formyl-6-methoxyphenyl 3-(4-methoxyphenyl)acrylate
(E)-4-formylphenyl 3-(4-methoxyphenyl)acrylate
4-((E)-((E)-4-(cinnamoyloxy)-3-methoxybenzylidene)amino)benzoic acid
4-((E)-((E)-3-chloro-4-(cinnamoyloxy)-5-methoxybenzylidene)amino)benzoic acid
4-((E)-((E)-3-bromo-4-(cinnamoyloxy)-5-methoxybenzylidene)amino)benzoic acid
4-((E)-((E)-4-(cinnamoyloxy)benzylidene)amino)benzoic acid
4-((E)-((E)-4-((E)-3-(3-chlorophenyl)acryloyloxy)-3-methoxybenzylidene)amino)benzoic acid
4-((E)-((E)-3-chloro-4-((E)-3-(3-chlorophenyl)acryloyloxy)-5-methoxybenzylidene)amino)benzoic acid
4-((E)-((E)-3-bromo-4-((E)-3-(3-chlorophenyl)acryloyloxy)-5-methoxybenzylidene)amino)benzoic acid
4-((E)-((E)-4-((E)-3-(3-chlorophenyl)acryloyloxy)benzylidene)amino)benzoic acid
4-((E)-((E)-4-((E)-3-(3-bromophenyl)acryloyloxy)-3-methoxybenzylidene)amino)benzoic acid
4-((E)-((E)-3-bromophenyl)acryloyloxy)-3-chloro-5-methoxybenzylidene)amino)benzoic acid
4-((E)-((E)-3-bromo-4-((E)-3-(3-bromophenyl)acryloyloxy)-5-methoxybenzylidene)amino)benzoic acid
4-((E)-((E)-4-((E)-3-(3-bromophenyl)acryloyloxy)benzylidene)amino)benzoic acid
4-((E)-((E)-3-methoxy-4-((E)-3-(3-methoxyphenyl)acryloyloxy)benzylidene)amino)benzoic acid
4-((E)-((E)-3-chloro-5-methoxy-4-((E)-3-(3-methoxyphenyl)acryloyloxy)benzylidene)amino)benzoic acid
4-((E)-((E)-3-bromo-5-methoxy-4-((E)-3-(3-methoxyphenyl)acryloyloxy)benzylidene)amino)benzoic acid
4-((E)-((E)-4-((E)-3-(3-methoxyphenyl)acryloyloxy)benzylidene)amino)benzoic acid
4-((E)-((E)-4-((E)-3-(4-chlorophenyl)acryloyloxy)-3-methoxybenzylidene)amino)benzoic acid
4-((E)-((E)-3-chloro-4-((E)-3-(4-chlorophenyl)acryloyloxy)-5-methoxybenzylidene)amino)benzoic acid
4-((E)-((E)-3-bromo-4-((E)-3-(4-chlorophenyl)acryloyloxy)-5-methoxybenzylidene)amino)benzoic acid
4-((E)-((E)-4-((E)-3-(4-chlorophenyl)acryloyloxy)benzylidene)amino)benzoic acid
4-((E)-((E)-4-((E)-3-(4-bromophenyl)acryloyloxy)-3-methoxybenzylidene)amino)benzoic acid
4-((E)-((E)-4-((E)-3-(4-bromophenyl)acryloyloxy)-3-chloro-5-methoxybenzylidene)amino)benzoic acid
4-((E)-((E)-3-bromo-4-((E)-3-(4-bromophenyl)acryloyloxy)-5-methoxybenzylidene)amino)benzoic acid
4-((E)-((E)-4-((E)-3-(4-bromophenyl)acryloyloxy)benzylidene)amino)benzoic acid
4-((E)-((E)-3-methoxy-4-((E)-3-(4-methoxyphenyl)acryloyloxy)benzylidene)amino)benzoic acid
4-((E)-((E)-3-chloro-5-methoxy-4-((E)-3-(4-methoxyphenyl)acryloyloxy)benzylidene)amino)benzoic acid
4-((E)-((E)-3-bromo-5-methoxy-4-((E)-3-(4-methoxyphenyl)acryloyloxy)benzylidene)amino)benzoic acid
4-((E)-((E)-4-((E)-3-(4-methoxyphenyl)acryloyloxy)benzylidene)amino)benzoic acid
2-((E)-((E)-4-(cinnamoyloxy)-3-methoxybenzylidene)amino)-3-methylbutanoic acid
2-((E)-((E)-3-chloro-4-(cinnamoyloxy)-5-methoxybenzylidene)amino)-3-methylbutanoic acid
2-((E)-((E)-3-bromo-4-(cinnamoyloxy)-5-methoxybenzylidene)amino)-3-methylbutanoic acid
2-((E)-((E)-4-(cinnamoyloxy)benzylidene)amino)-3-methylbutanoic acid
2-((E)-((E)-4-((E)-3-(3-chlorophenyl)acryloyloxy)-3-methoxybenzylidene)amino)-3-methylbutanoic acid
2-((E)-((E)-3-chloro-4-((E)-3-(3-chlorophenyl)acryloyloxy)-5-methoxybenzylidene)amino)-3-methylbutanoic acid
2-((E)-((E)-3-bromo-4-((E)-3-(3-chlorophenyl)acryloyloxy)-5-methoxybenzylidene)amino)-3-methylbutanoic acid
2-((E)-((E)-4-((E)-3-(3-chlorophenyl)acryloyloxy)benzylidene)amino)-3-methylbutanoic acid
2-((E)-((E)-4-((E)-3-(3-bromophenyl)acryloyloxy)-3-methoxybenzylidene)amino)-3-methylbutanoic acid
2-((E)-((E)-4-((E)-3-(3-bromophenyl)acryloyloxy)-3-chloro-5-methoxybenzylidene)amino)-3-methylbutanoic acid
2-((E)-((E)-3-bromo-4-((E)-3-(3-bromophenyl)acryloyloxy)-5-methoxybenzylidene)amino)-3-methylbutanoic acid
2-((E)-((E)-4-((E)-3-(3-bromophenyl)acryloyloxy)benzylidene)amino)-3-methylbutanoic acid
2-((E)-((E)-3-methoxy-4-((E)-3-(3-methoxyphenyl)acryloyloxy)benzylidene)amino)-3-methylbutanoic acid 2-((E)-((E)-3-chloro-5-methoxy-4-((E)-3-(3-methoxyphenyl)acryloyloxy)benzylidene)amino)-3-methylbutanoic acid
2-((E)-((E)-3-bromo-5-methoxy-4-((E)-3-(3-methoxyphenyl)acryloyloxy)benzylidene)amino)-3-methylbutanoic acid
2-((E)-((E)-4-((E)-3-(3-methoxyphenyl)acryloyloxy)benzylidene)amino)-3-methylbutanoic acid
2-((E)-((E)-4-((E)-3-(4-chlorophenyl)acryloyloxy)-3-methoxybenzylidene)amino)-3-methylbutanoic acid
2-((E)-((E)-3-chloro-4-((E)-3-(4-chlorophenyl)acryloyloxy)-5-methoxybenzylidene)amino)-3-methylbutanoic acid
2-((E)-((E)-3-bromo-4-((E)-3-(4-chlorophenyl)acryloyloxy)-5-methoxybenzylidene)amino)-3-methylbutanoic acid
2-((E)-((E)-4-((E)-3-(4-chlorophenyl)acryloyloxy)benzylidene)amino)-3-methylbutanoic acid
2-((E)-((E)-4-((E)-3-(4-bromophenyl)acryloyloxy)-3-methoxybenzylidene)amino)-3-methylbutanoic acid
2-((E)-((E)-4-((E)-3-(4-bromophenyl)acryloyloxy)-3-chloro-5-methoxybenzylidene)amino)-3-methylbutanoic acid
2-((E)-((E)-3-bromo-4-((E)-3-(4-bromophenyl)acryloyloxy)-5-methoxybenzylidene)amino)-3-methylbutanoic acid
2-((E)-((E)-4-((E)-3-(4-bromophenyl)acryloyloxy)benzylidene)amino)-3-methylbutanoic acid
2-((E)-((E)-3-methoxy-4-((E)-3-(4-methoxyphenyl)acryloyloxy)benzylidene)amino)-3-methylbutanoic acid
2-((E)-((E)-3-chloro-5-methoxy-4-((E)-3-(4-methoxyphenyl)acryloyloxy)benzylidene)amino)-3-methylbutanoic acid
2-((E)-((E)-3-bromo-5-methoxy-4-((E)-3-(4-methoxyphenyl)acryloyloxy)benzylidene)amino)-3-methylbutanoic acid
2-((E)-((E)-4-((E)-3-(4-methoxyphenyl)acryloyloxy)benzylidene)amino)-3-methylbutanoic acid
2-((E)-((E)-4-(cinnamoyloxy)-3-methoxybenzylidene)amino)-3-methylpentanoic acid
2-((E)-((E)-3-chloro-4-(cinnamoyloxy)-5-methoxybenzylidene)amino)-3-methylpentanoic acid
2-((E)-((E)-3-bromo-4-(cinnamoyloxy)-5-methoxybenzylidene)amino)-3-methylpentanoic acid
2-((E)-((E)-4-(cinnamoyloxy)benzylidene)amino)-3-methylpentanoic acid
2-((E)-((E)-4-((E)-3-(3-chlorophenyl)acryloyloxy)-3-methoxybenzylidene)amino)-3-methylpentanoic acid
2-((E)-((E)-3-chloro-4-((E)-3-(3-chlorophenyl)acryloyloxy)-5-methoxybenzylidene)amino)-3-methylpentanoic acid
2-((E)-((E)-3-bromo-4-((E)-3-(3-chlorophenyl)acryloyloxy)-5-methoxybenzylidene)amino)-3-methylpentanoic acid
2-((E)-((E)-4-((E)-3-(3-chlorophenyl)acryloyloxy)benzylidene)amino)-3-methylpentanoic acid
2-((E)-((E)-4-((E)-3-(3-bromophenyl)acryloyloxy)-3-methoxybenzylidene)amino)-3-methylpentanoic acid
2-((E)-((E)-4-((E)-3-(3-bromophenyl)acryloyloxy)-3-chloro-5-methoxybenzylidene)amino)-3-methylpentanoic acid
2-((E)-((E)-3-bromo-4-((E)-3-(3-bromophenyl)acryloyloxy)-5-methoxybenzylidene)amino)-3-methylpentanoic acid
2-((E)-((E)-4-((E)-3-(3-bromophenyl)acryloyloxy)benzylidene)amino)-3-methylpentanoic acid
2-((E)-((E)-3-methoxy-4-((E)-3-(3-methoxyphenyl)acryloyloxy)benzylidene)amino)-3-methylpentanoic acid
2-((E)-((E)-3-chloro-5-methoxy-4-((E)-3-(3-methoxyphenyl)acryloyloxy)benzylidene)amino)-3-methylpentanoic acid
2-((E)-((E)-3-bromo-5-methoxy-4-((E)-3-(3-methoxyphenyl)acryloyloxy)benzylidene)amino)-3-methylpentanoic acid
2-((E)-((E)-4-((E)-3-(3-methoxyphenyl)acryloyloxy)benzylidene)amino)-3-methylpentanoic acid
2-((E)-((E)-4-((E)-3-(4-chlorophenyl)acryloyloxy)-3-methoxybenzylidene)amino)-3-methylpentanoic acid
2-((E)-((E)-3-chloro-4-((E)-3-(4-chlorophenyl)acryloyloxy)-5-methoxybenzylidene)amino)-3-methylpentanoic acid
2-((E)-((E)-3-bromo-4-((E)-3-(4-chlorophenyl)acryloyloxy)-5-methoxybenzylidene)amino)-3-methylpentanoic acid
2-((E)-((E)-4-((E)-3-(4-chlorophenyl)acryloyloxy)benzylidene)amino)-3-methylpentanoic acid
2-((E)-((E)-4-((E)-3-(4-bromophenyl)acryloyloxy)-3-methoxybenzylidene)amino)-3-methylpentanoic acid
2-((E)-((E)-4-((E)-3-(4-bromophenyl)acryloyloxy)-3-chloro-5-methoxybenzylidene)amino)-3-methylpentanoic acid
2-((E)-((E)-3-bromo-4-((E)-3-(4-bromophenyl)acryloyloxy)-5-methoxybenzylidene)amino)-3-methylpentanoic acid
2-((E)-((E)-4-((E)-3-(4-bromophenyl)acryloyloxy)benzylidene)amino)-3-methylpentanoic acid
2-((E)-((E)-3-methoxy-4-((E)-3-(4-methoxyphenyl)acryloyloxy)benzylidene)amino)-3-methylpentanoic acid
2-((E)-((E)-3-chloro-5-methoxy-4-((E)-3-(4-methoxyphenyl)acryloyloxy)benzylidene)amino)-3-methylpentanoic acid
2-((E)-((E)-3-bromo-5-methoxy-4-((E)-3-(4-methoxyphenyl)acryloyloxy)benzylidene)amino)-3-methylpentanoic acid
2-((E)-((E)-4-((E)-3-(4-methoxyphenyl)acryloyloxy)benzylidene)amino)-3-methylpentanoic acid
4-((E)-(hydroxyimino)methyl)-2-methoxyphenyl cinnamate
2-chloro-4-((E)-(hydroxyimino)methyl)-6-methoxyphenyl cinnamate
2-bromo-4-((E)-(hydroxyimino)methyl)-6-methoxyphenyl cinnamate
4-((E)-(hydroxyimino)methyl)phenyl cinnamate
(E)-4-((E)-(hydroxyimino)methyl)-2-methoxyphenyl 3-(3-chlorophenyl)acrylate
(E)-2-chloro-4-((E)-(hydroxyimino)methyl)-6-methoxyphenyl 3-(3-chlorophenyl)acrylate
(E)-2-bromo-4-((E)-(hydroxyimino)methyl)-6-methoxyphenyl 3-(3-chlorophenyl)acrylate
(E)-4-((E)-(hydroxyimino)methyl)phenyl 3-(3-chlorophenyl)acrylate
(E)-4-((E)-(hydroxyimino)methyl)-2-methoxyphenyl 3-(3-bromophenyl)acrylate
(E)-2-chloro-4-((E)-(hydroxyimino)methyl)-6-methoxyphenyl 3-(3-bromophenyl)acrylate
(E)-2-bromo-4-((E)-(hydroxyimino)methyl)-6-methoxyphenyl 3-(3-bromophenyl)acrylate
(E)-4-((E)-(hydroxyimino)methyl)phenyl 3-(3-bromophenyl)acrylate
(E)-4-((E)-(hydroxyimino)methyl)-2-methoxyphenyl 3-(3-methoxyphenyl)acrylate
(E)-2-chloro-4-((E)-(hydroxyimino)methyl)-6-methoxyphenyl 3-(3-methoxyphenyl)acrylate (E)-2-bromo-4-((E)-(hydroxyimino)methyl)-6-methoxyphenyl 3-(3-methoxyphenyl)acrylate
(E)-4-((E)-(hydroxyimino)methyl)phenyl 3-(3-methoxyphenyl)acrylate
(E)-4-((E)-(hydroxyimino)methyl)-2-methoxyphenyl 3-(4-chlorophenyl)acrylate
(E)-2-chloro-4-((E)-(hydroxyimino)methyl)-6-methoxyphenyl 3-(4-chlorophenyl)acrylate
(E)-2-bromo-4-((E)-(hydroxyimino)methyl)-6-methoxyphenyl 3-(4-chlorophenyl)acrylate
(E)-4-((E)-(hydroxyimino)methyl)phenyl 3-(4-chlorophenyl)acrylate
(E)-4-((E)-(hydroxyimino)methyl)-2-methoxyphenyl 3-(4-bromophenyl)acrylate
(E)-2-chloro-4-((E)-(hydroxyimino)methyl)-6-methoxyphenyl 3-(4-bromophenyl)acrylate
(E)-2-bromo-4-((E)-(hydroxyimino)methyl)-6-methoxyphenyl 3-(4-bromophenyl)acrylate
(E)-4-((E)-(hydroxyimino)methyl)phenyl 3-(4-bromophenyl)acrylate
(E)-4-((E)-(hydroxyimino)methyl)-2-methoxyphenyl 3-(4-methoxyphenyl)acrylate
(E)-2-chloro-4-((E)-(hydroxyimino)methyl)-6-methoxyphenyl 3-(4-methoxyphenyl)acrylate
(E)-2-bromo-4-((E)-(hydroxyimino)methyl)-6-methoxyphenyl 3-(4-methoxyphenyl)acrylate
(E)-4-((E)-(hydroxyimino)methyl)phenyl 3-(4-methoxyphenyl)acrylate
2-methoxy-4-((E)-ureidomethyl)phenyl cinnamate
2-chloro-6-methoxy-4-((E)-ureidomethyl)phenyl cinnamate
2-bromo-6-methoxy-4-((E)-ureidomethyl)phenyl cinnamate
4-((E)-ureidomethyl)phenyl cinnamate
(E)-2-methoxy-4-((E)-ureidomethyl)phenyl 3-(3-chlorophenyl)acrylate
(E)-2-chloro-6-methoxy-4-((E)-ureidomethyl)phenyl 3-(3-chlorophenyl)acrylate
(E)-2-bromo-6-methoxy-4-((E)-ureidomethyl)phenyl 3-(3-chlorophenyl)acrylate
(E)-4-((E)-ureidomethyl)phenyl 3-(3-chlorophenyl)acrylate
(E)-2-methoxy-4-((E)-ureidomethyl)phenyl 3-(3-bromophenyl)acrylate
(E)-2-chloro-6-methoxy-4-((E)-ureidomethyl)phenyl 3-(3-bromophenyl)acrylate
(E)-2-bromo-6-methoxy-4-((E)-ureidomethyl)phenyl 3-(3-bromophenyl)acrylate
(E)-4-((E)-ureidomethyl)phenyl 3-(3-bromophenyl)acrylate
(E)-2-methoxy-4-((E)-ureidomethyl)phenyl 3-(3-methoxyphenyl)acrylate
(E)-2-chloro-6-methoxy-4-((E)-ureidomethyl)phenyl 3-(3-methoxyphenyl)acrylate
(E)-2-bromo-6-methoxy-4-((E)-ureidomethyl)phenyl 3-(3-methoxyphenyl)acrylate
(E)-4-((E)-ureidomethyl)phenyl 3-(3-methoxyphenyl)acrylate
(E)-2-methoxy-4-((E)-ureidomethyl)phenyl 3-(4-chlorophenyl)acrylate
(E)-2-chloro-6-methoxy-4-((E)-ureidomethyl)phenyl 3-(4-chlorophenyl)acrylate
(E)-2-bromo-6-methoxy-4-((E)-ureidomethyl)phenyl 3-(4-chlorophenyl)acrylate
(E)-4-((E)-ureidomethyl)phenyl 3-(4-chlorophenyl)acrylate
(E)-2-methoxy-4-((E)-ureidomethyl)phenyl 3-(4-bromophenyl)acrylate
(E)-2-chloro-6-methoxy-4-((E)-ureidomethyl)phenyl 3-(4-bromophenyl)acrylate
(E)-2-bromo-6-methoxy-4-((E)-ureidomethyl)phenyl 3-(4-bromophenyl)acrylate
(E)-4-((E)-ureidomethyl)phenyl 3-(4-bromophenyl)acrylate
(E)-2-methoxy-4-((E)-ureidomethyl)phenyl 3-(4-methoxyphenyl)acrylate
(E)-2-chloro-6-methoxy-4-((E)-ureidomethyl)phenyl 3-(4-methoxyphenyl)acrylate
(E)-2-bromo-6-methoxy-4-((E)-ureidomethyl)phenyl 3-(4-methoxyphenyl)acrylate
(E)-4-((E)-ureidomethyl)phenyl 3-(4-methoxyphenyl)acrylate
4-((E)-(4-hydroxyphenylimino)methyl)-2-methoxyphenyl cinnamate
2-chloro-4-((E)-(4-hydroxyphenylimino)methyl)-6-methoxyphenyl cinnamate
2-bromo-4-((E)-(4-hydroxyphenylimino)methyl)-6-methoxyphenyl cinnamate
4-((E)-(4-hydroxyphenylimino)methyl)phenyl cinnamate
(E)-4-((E)-(4-hydroxyphenylimino)methyl)-2-methoxyphenyl 3-(3-chlorophenyl)acrylate
(E)-2-chloro-4-((E)-(4-hydroxyphenylimino)methyl)-6-methoxyphenyl 3-(3-chlorophenyl)acrylate
(E)-2-bromo-4-((E)-(4-hydroxyphenylimino)methyl)-6-methoxyphenyl 3-(3-chlorophenyl)acrylate
(E)-4-((E)-(4-hydroxyphenylimino)methyl)phenyl 3-(3-chlorophenyl)acrylate
(E)-4-((E)-(4-hydroxyphenylimino)methyl)-2-methoxyphenyl 3-(3-bromophenyl)acrylate
(E)-2-chloro-4-((E)-(4-hydroxyphenylimino)methyl)-6-methoxyphenyl 3-(3-bromophenyl)acrylate
(E)-2-bromo-4-((E)-(4-hydroxyphenylimino)methyl)-6-methoxyphenyl 3-(3-bromophenyl)acrylate
(E)-4-((E)-(4-hydroxyphenylimino)methyl)phenyl 3-(3-bromophenyl)acrylate
(E)-4-((E)-(4-hydroxyphenylimino)methyl)-2-methoxyphenyl 3-(3-methoxyphenyl)acrylate
(E)-2-chloro-4-((E)-(4-hydroxyphenylimino)methyl)-6-methoxyphenyl 3-(3-methoxyphenyl)acrylate
(E)-2-bromo-4-((E)-(4-hydroxyphenylimino)methyl)-6-methoxyphenyl 3-(3-methoxyphenyl)acrylate
(E)-4-((E)-(4-hydroxyphenylimino)methyl)phenyl 3-(3-methoxyphenyl)acrylate
(E)-4-((E)-(4-hydroxyphenylimino)methyl)-2-methoxyphenyl 3-(4-chlorophenyl)acrylate
(E)-2-chloro-4-((E)-(4-hydroxyphenylimino)methyl)-6-methoxyphenyl 3-(4-chlorophenyl)acrylate
(E)-2-bromo-4-((E)-(4-hydroxyphenylimino)methyl)-6-methoxyphenyl 3-(4-chlorophenyl)acrylate
(E)-4-((E)-(4-hydroxyphenylimino)methyl)phenyl 3-(4-chlorophenyl)acrylate
(E)-4-((E)-(4-hydroxyphenylimino)methyl)-2-methoxyphenyl 3-(4-bromophenyl)acrylate
(E)-2-chloro-4-((E)-(4-hydroxyphenylimino)methyl)-6-methoxyphenyl 3-(4-bromophenyl)acrylate
(E)-2-bromo-4-((E)-(4-hydroxyphenylimino)methyl)-6-methoxyphenyl 3-(4-bromophenyl)acrylate
(E)-4-((E)-(4-hydroxyphenylimino)methyl)phenyl 3-(4-bromophenyl)acrylate
(E)-4-((E)-(4-hydroxyphenylimino)methyl)-2-methoxyphenyl 3-(4-methoxyphenyl)acrylate
(E)-2-chloro-4-((E)-(4-hydroxyphenylimino)methyl)-6-methoxyphenyl 3-(4-methoxyphenyl)acrylate
(E)-2-bromo-4-((E)-(4-hydroxyphenylimino)methyl)-6-methoxyphenyl 3-(4-methoxyphenyl)acrylate
(E)-4-((E)-(4-hydroxyphenylimino)methyl)phenyl 3-(4-methoxyphenyl)acrylate 4-((E)-(2'-4'-dinitrophenylhydrazo)methyl)-2-methoxyphenyl cinnamate 2-chloro-4-((E)-(2'-4'-dinitrophenylhydrazo)methyl)-6-methoxyphenyl cinnamate 2-bromo-4-((E)-(2'-4'-dinitrophenylhydrazo)methyl)-6-methoxyphenyl cinnamate 4-((E)-(2'-4'-dinitrophenylhydrazo)methyl)phenyl cinnamate (E)-4-((E)-(2'-4'-dinitrophenylhydrazo)methyl)-2-methoxyphenyl 3-(3-chlorophenyl)acrylate (E)-2-chloro-4-((E)-(2'-4'-dinitrophenylhydrazo)methyl)-6-methoxyphenyl 3-(3-chlorophenyl)acrylate (E)-2-bromo-4-((E)-(2'-4'-dinitrophenylhydrazo)methyl)-6-methoxyphenyl 3-(3-chlorophenyl)acrylate (E)-4-((E)-(2'-4'-dinitrophenylhydrazo)methyl)phenyl 3-(3-chlorophenyl)acrylate (E)-4-((E)-(2'-4'-dinitrophenylhydrazo)methyl)-2-methoxyphenyl 3-(3-bromophenyl)acrylate (E)-2-chloro-4-((E)-(2'-4'-dinitrophenylhydrazo)methyl)-6-methoxyphenyl 3-(3-bromophenyl)acrylate (E)-2-bromo-4-((E)-(2'-4'-dinitrophenylhydrazo)methyl)-6-methoxyphenyl 3-(3-bromophenyl)acrylate (E)-4-((E)-(2'-4'-dinitrophenylhydrazo)methyl)phenyl 3-(3-bromophenyl)acrylate (E)-4-((E)-(2'-4'-dinitrophenylhydrazo)methyl)-2-methoxyphenyl 3-(3-methoxyphenyl)acrylate (E)-2-chloro-4-((E)-(2'-4'-dinitrophenylhydrazo)methyl)-6-methoxyphenyl 3-(3-methoxyphenyl)acrylate (E)-2-bromo-4-((E)-(2'-4'-dinitrophenylhydrazo)methyl)-6-methoxyphenyl 3-(3-methoxyphenyl)acrylate (E)-4-((E)-(2'-4'-dinitrophenylhydrazo)methyl)phenyl 3-(3-methoxyphenyl)acrylate (E)-4-((E)-(2'-4'-dinitrophenylhydrazo)methyl)-2-methoxyphenyl 3-(4-chlorophenyl)acrylate (E)-2-chloro-4-((E)-(2'-4'-dinitrophenylhydrazo)methyl)-6-methoxyphenyl 3-(4-chlorophenyl)acrylate (E)-2-bromo-4-((E)-(2'-4'-dinitrophenylhydrazo)methyl)-6-methoxyphenyl 3-(4-chlorophenyl)acrylate (E)-4-((E)-(2'-4'-dinitrophenylhydrazo)methyl)phenyl 3-(4-chlorophenyl)acrylate (E)-4-((E)-(2'-4'-dinitrophenylhydrazo)methyl)-2-methoxyphenyl 3-(4-bromophenyl)acrylate (E)-2-chloro-4-((E)-(2'-4'-dinitrophenylhydrazo)methyl)-6-methoxyphenyl 3-(4-bromophenyl)acrylate (E)-2-bromo-4-((E)-(2'-4'-dinitrophenylhydrazo)methyl)-6-methoxyphenyl 3-(4-bromophenyl)acrylate (E)-4-((E)-(2'-4'-dinitrophenylhydrazo)methyl)phenyl 3-(4-bromophenyl)acrylate (E)-4-((E)-(2'-4'-dinitrophenylhydrazo)methyl)-2-methoxyphenyl 3-(4-methoxyphenyl)acrylate (E)-2-chloro-4-((E)-(2'-4'-dinitrophenylhydrazo)methyl)-6-methoxyphenyl 3-(4-methoxyphenyl)acrylate (E)-2-bromo-4-((E)-(2'-4'-dinitrophenylhydrazo)methyl)-6-methoxyphenyl 3-(4-methoxyphenyl)acrylate (E)-4-((E)-(2'-4'-dinitrophenylhydrazo)methyl)phenyl 3-(4-methoxyphenyl)acrylate The list also consists of the IUPAC names of the compounds given the table below—

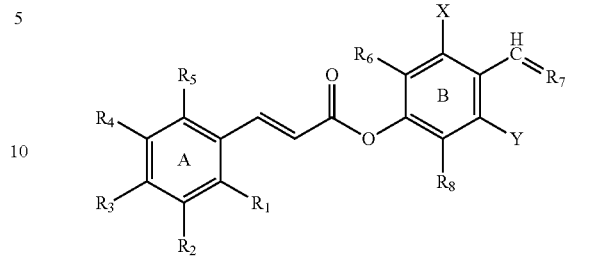

(4a)
X = Y = hydrogen; R1 = R4 = R5 = hydrogen

| S.No | R7 | R8 | R6 | R2 | R3 |
|---|---|---|---|---|---|
| 1. | O | OCH₃ | H | H | H |
| 2. | O | OCH₃ | Cl | H | H |
| 3. | O | OCH₃ | Br | H | H |
| 4. | O | H | H | H | H |
| 5. | O | OCH₃ | H | Cl | H |
| 6. | O | OCH₃ | Cl | Cl | H |
| 7. | O | OCH₃ | Br | Cl | H |
| 8. | O | H | H | Cl | H |
| 9. | O | OCH₃ | H | Br | H |
| 10. | O | OCH₃ | Cl | Br | H |
| 11. | O | OCH₃ | Br | Br | H |
| 12. | O | H | H | Br | H |
| 13. | O | OCH₃ | H | OCH₃ | H |
| 14. | O | OCH₃ | Cl | OCH₃ | H |
| 15. | O | OCH₃ | Br | OCH₃ | H |
| 16. | O | H | H | OCH₃ | H |
| 17. | O | OCH₃ | H | H | Cl |
| 18. | O | OCH₃ | Cl | H | Cl |
| 19. | O | OCH₃ | Br | H | Cl |
| 20. | O | H | H | H | Cl |
| 21. | O | OCH₃ | H | H | Br |
| 22. | O | OCH₃ | Cl | H | Br |
| 23. | O | OCH₃ | Br | H | Br |
| 24. | O | H | H | H | Br |
| 25. | O | OCH₃ | H | H | OCH₃ |
| 26. | O | OCH₃ | Cl | H | OCH₃ |
| 27. | O | OCH₃ | Br | H | OCH₃ |
| 28. | O | H | H | H | OCH₃ |
| 29. | 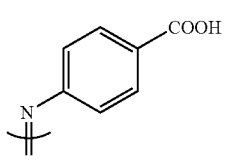 | OCH₃ | H | H | H |
| 30. | 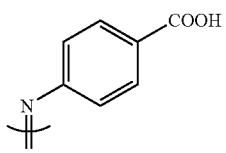 | OCH₃ | Cl | H | H |
| 31. | 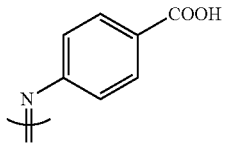 | OCH₃ | Br | H | H |
| 32. | 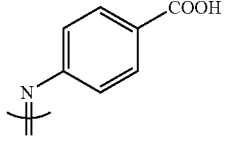 | H | H | H | H |

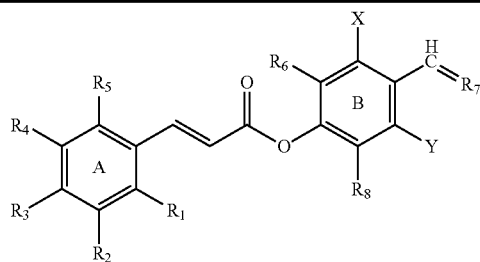

(4a)
X = Y = hydrogen; R1 = R4 = R5 = hydrogen

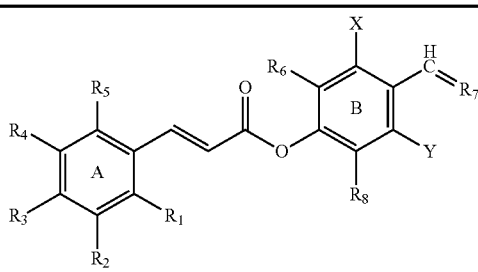

(4a)
X = Y = hydrogen; R1 = R4 = R5 = hydrogen

| S.No | R7 | R8 | R6 | R2 | R3 |
|---|---|---|---|---|---|
| 33. | 4-COOH-C6H4-N= | OCH3 | H | Cl | H |
| 34. | 4-COOH-C6H4-N= | OCH3 | Cl | Cl | H |
| 35. | 4-COOH-C6H4-N= | OCH3 | Br | Cl | H |
| 36. | 4-COOH-C6H4-N= | H | H | Cl | H |
| 37. | 4-COOH-C6H4-N= | OCH3 | H | Br | H |
| 38. | 4-COOH-C6H4-N= | OCH3 | Cl | Br | H |
| 39. | 4-COOH-C6H4-N= | OCH3 | Br | Br | H |
| 40. | 4-COOH-C6H4-N= | H | H | Br | H |

| S.No | R7 | R8 | R6 | R2 | R3 |
|---|---|---|---|---|---|
| 41. | 4-COOH-C6H4-N= | OCH3 | H | OCH3 | H |
| 42. | 4-COOH-C6H4-N= | OCH3 | Cl | OCH3 | H |
| 43. | 4-COOH-C6H4-N= | OCH3 | Br | OCH3 | H |
| 44. | 4-COOH-C6H4-N= | H | H | OCH3 | H |
| 45. | 4-COOH-C6H4-N= | OCH3 | H | H | Cl |
| 46. | 4-COOH-C6H4-N= | OCH3 | Cl | H | Cl |
| 47. | 4-COOH-C6H4-N= | OCH3 | Br | H | Cl |
| 48. | 4-COOH-C6H4-N= | H | H | H | Cl |

17
-continued

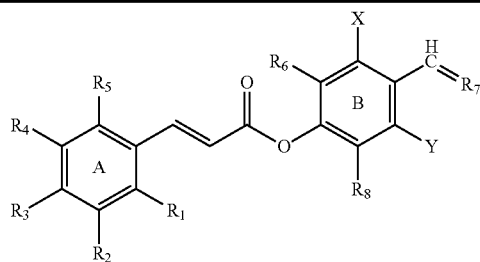

(4a)
X = Y = hydrogen; R1 = R4 = R5 = hydrogen

| S.No | R7 | R8 | R6 | R2 | R3 |
|---|---|---|---|---|---|
| 49. | 4-COOH-C6H4-N= | OCH$_3$ | H | H | Br |
| 50. | 4-COOH-C6H4-N= | OCH$_3$ | Cl | H | Br |
| 51. | 4-COOH-C6H4-N= | OCH$_3$ | Br | H | Br |
| 52. | 4-COOH-C6H4-N= | H | H | H | Br |
| 53. | 4-COOH-C6H4-N= | OCH$_3$ | H | H | OCH$_3$ |
| 54. | 4-COOH-C6H4-N= | OCH$_3$ | Cl | H | OCH$_3$ |
| 55. | 4-COOH-C6H4-N= | OCH$_3$ | Br | H | OCH$_3$ |
| 56. | 4-COOH-C6H4-N= | H | H | H | OCH$_3$ |

18
-continued

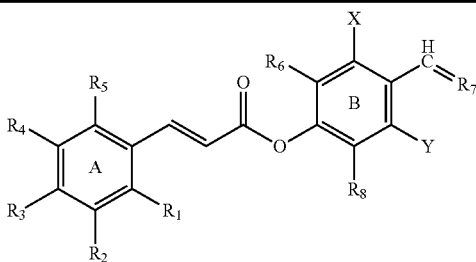

(4a)
X = Y = hydrogen; R1 = R4 = R5 = hydrogen

| S.No | R7 | R8 | R6 | R2 | R3 |
|---|---|---|---|---|---|
| 57. | valine-N= | OCH$_3$ | H | H | H |
| 58. | valine-N= | OCH$_3$ | Cl | H | H |
| 59. | valine-N= | OCH$_3$ | Br | H | H |
| 60. | valine-N= | H | H | H | H |
| 61. | valine-N= | OCH$_3$ | H | Cl | H |
| 62. | valine-N= | OCH$_3$ | Cl | Cl | H |
| 63. | valine-N= | OCH$_3$ | Br | Cl | H |
| 64. | valine-N= | H | H | Cl | H |

19
-continued
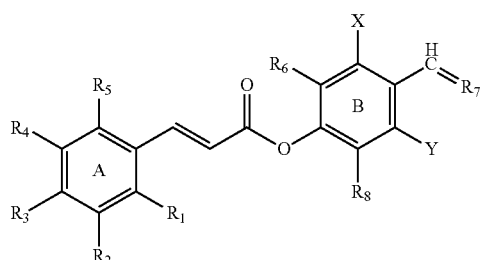
(4a)
X = Y = hydrogen; R1 = R4 = R5 = hydrogen
| S.No | R7 | R8 | R6 | R2 | R3 |
|---|---|---|---|---|---|
| 65. | 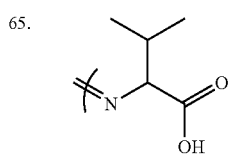 | OCH₃ | H | Br | H |
| 66. | 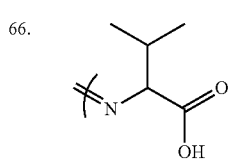 | OCH₃ | Cl | Br | H |
| 67. | 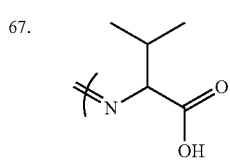 | OCH₃ | Br | Br | H |
| 68. | 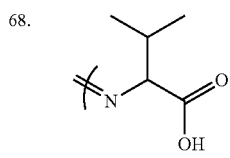 | H | H | Br | H |
| 69. | 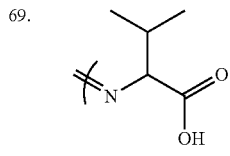 | OCH₃ | H | OCH₃ | H |
| 70. | 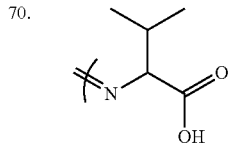 | OCH₃ | Cl | OCH₃ | H |
| 71. | 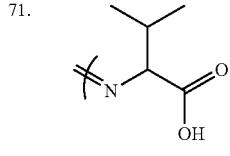 | OCH₃ | Br | OCH₃ | H |
20
-continued
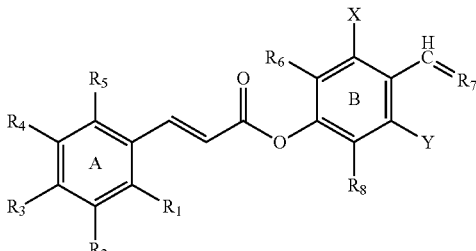
(4a)
X = Y = hydrogen; R1 = R4 = R5 = hydrogen
| S.No | R7 | R8 | R6 | R2 | R3 |
|---|---|---|---|---|---|
| 72. | 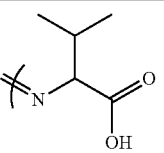 | H | H | OCH₃ | H |
| 73. | 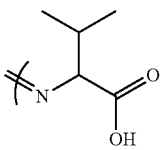 | OCH₃ | H | H | Cl |
| 74. | 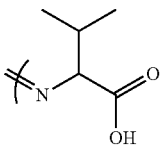 | OCH₃ | Cl | H | Cl |
| 75. | 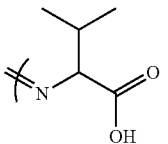 | OCH₃ | Br | H | Cl |
| 76. | 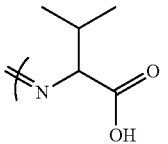 | H | H | H | Cl |
| 77. | 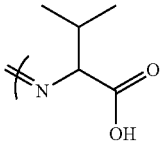 | OCH₃ | H | H | Br |
| 78. | 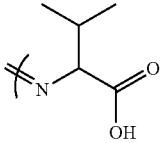 | OCH₃ | Cl | H | Br |
| 79. | 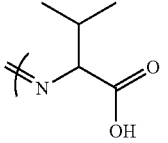 | OCH₃ | Br | H | Br |

-continued
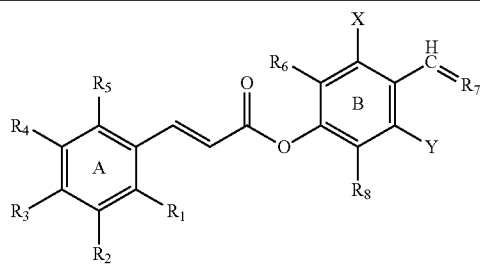
(4a)
X = Y = hydrogen; R1 = R4 = R5 = hydrogen
| S.No | R7 | R8 | R6 | R2 | R3 |
|------|----|----|----|----|----|
| 80. | | H | H | H | Br |
| 81. | | OCH₃ | H | H | OCH₃ |
| 82. | | OCH₃ | Cl | H | OCH₃ |
| 83. | | OCH₃ | Br | H | OCH₃ |
| 84. | | H | H | H | OCH₃ |
| 85. | | OCH₃ | H | H | H |
| 86. | | OCH₃ | Cl | H | H |
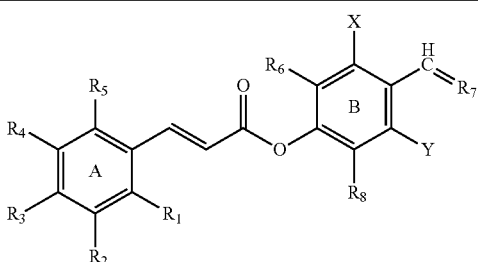
(4a)
X = Y = hydrogen; R1 = R4 = R5 = hydrogen
| S.No | R7 | R8 | R6 | R2 | R3 |
|------|----|----|----|----|----|
| 87. | | OCH₃ | Br | H | H |
| 88. | | H | H | H | H |
| 89. | | OCH₃ | H | Cl | H |
| 90. | | OCH₃ | Cl | Cl | H |
| 91. | | OCH₃ | Br | Cl | H |
| 92. | | H | H | Cl | H |

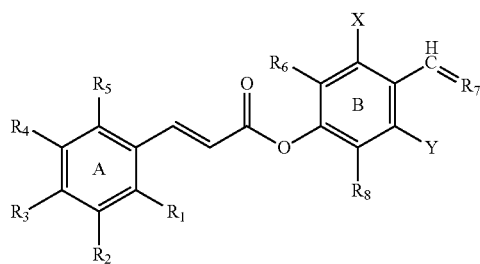
(4a)
X = Y = hydrogen; R1 = R4 = R5 = hydrogen
| S.No | R7 | R8 | R6 | R2 | R3 |
|---|---|---|---|---|---|
| 93. | 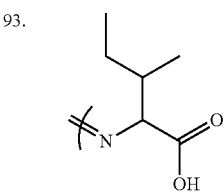 | OCH$_3$ | H | Br | H |
| 94. | 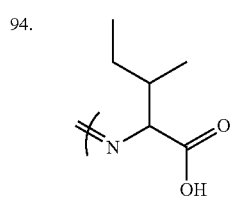 | OCH$_3$ | Cl | Br | H |
| 95. | 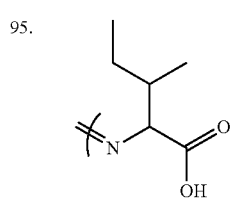 | OCH$_3$ | Br | Br | H |
| 96. | 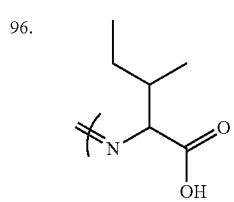 | H | H | Br | H |
| 97. | 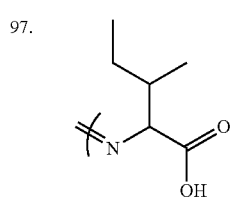 | OCH$_3$ | H | OCH$_3$ | H |
| 98. | 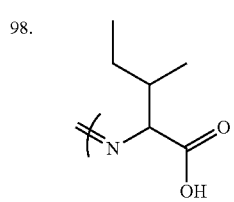 | OCH$_3$ | Cl | OCH$_3$ | H |
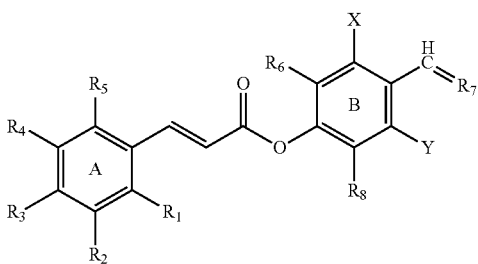
(4a)
X = Y = hydrogen; R1 = R4 = R5 = hydrogen
| S.No | R7 | R8 | R6 | R2 | R3 |
|---|---|---|---|---|---|
| 99. | 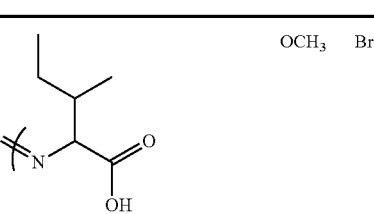 | OCH$_3$ | Br | OCH$_3$ | H |
| 100. | 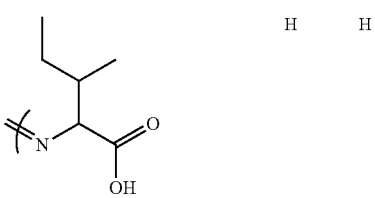 | H | H | OCH$_3$ | H |
| 101. | 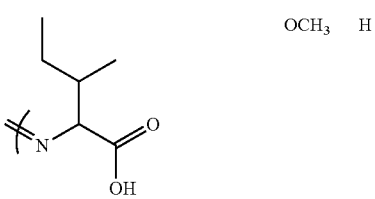 | OCH$_3$ | H | H | Cl |
| 102. | 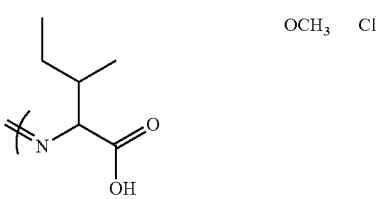 | OCH$_3$ | Cl | H | Cl |
| 103. | 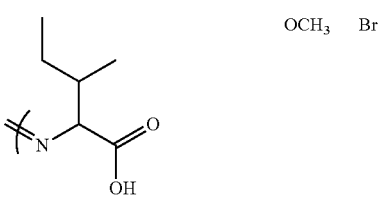 | OCH$_3$ | Br | H | Cl |
| 104. | 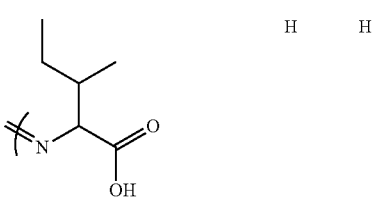 | H | H | H | Cl |

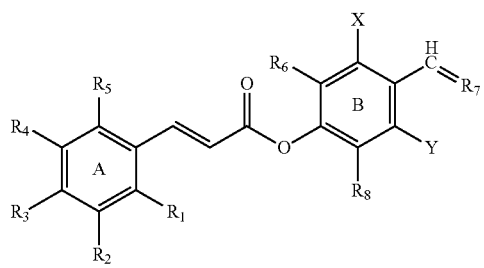

(4a)
X = Y = hydrogen; R1 = R4 = R5 = hydrogen

| S.No | R7 | R8 | R6 | R2 | R3 |
|---|---|---|---|---|---|
| 105. | 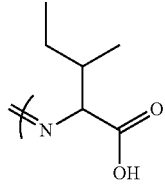 | $OCH_3$ | H | H | Br |
| 106. | 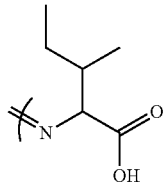 | $OCH_3$ | Cl | H | Br |
| 107. | 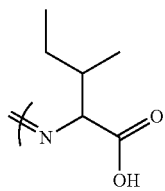 | $OCH_3$ | Br | H | Br |
| 108. | 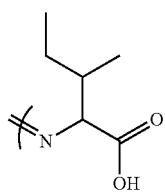 | H | H | H | Br |
| 109. | 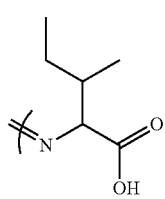 | $OCH_3$ | H | H | $OCH_3$ |
| 110. | 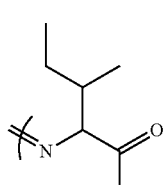 | $OCH_3$ | Cl | H | $OCH_3$ |

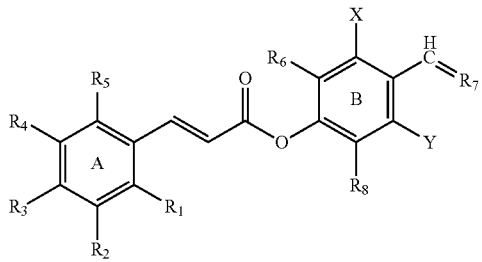

(4a)
X = Y = hydrogen; R1 = R4 = R5 = hydrogen

| S.No | R7 | R8 | R6 | R2 | R3 |
|---|---|---|---|---|---|
| 111. | 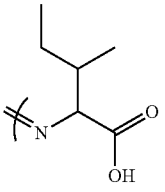 | $OCH_3$ | Br | H | $OCH_3$ |
| 112. | 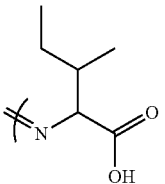 | H | H | H | $OCH_3$ |
| 113. | NOH | $OCH_3$ | H | H | H |
| 114. | NOH | $OCH_3$ | Cl | H | H |
| 115. | NOH | $OCH_3$ | Br | H | H |
| 116. | NOH | H | H | H | H |
| 117. | NOH | $OCH_3$ | H | Cl | H |
| 118. | NOH | $OCH_3$ | Cl | Cl | H |
| 119. | NOH | $OCH_3$ | Br | Cl | H |
| 120. | NOH | H | H | Cl | H |
| 121. | NOH | $OCH_3$ | H | Br | H |
| 122. | NOH | $OCH_3$ | Cl | Br | H |
| 123. | NOH | $OCH_3$ | Br | Br | H |
| 124. | NOH | H | H | Br | H |
| 125. | NOH | $OCH_3$ | H | $OCH_3$ | H |
| 126. | NOH | $OCH_3$ | Cl | $OCH_3$ | H |
| 127. | NOH | $OCH_3$ | Br | $OCH_3$ | H |
| 128. | NOH | H | H | $OCH_3$ | H |
| 129. | NOH | $OCH_3$ | H | H | Cl |
| 130. | NOH | $OCH_3$ | Cl | H | Cl |
| 131. | NOH | $OCH_3$ | Br | H | Cl |
| 132. | NOH | H | H | H | Cl |
| 133. | NOH | $OCH_3$ | H | H | Br |
| 134. | NOH | $OCH_3$ | Cl | H | Br |
| 135. | NOH | $OCH_3$ | Br | H | Br |
| 136. | NOH | H | H | H | Br |
| 137. | NOH | $OCH_3$ | H | H | $OCH_3$ |
| 138. | NOH | $OCH_3$ | Cl | H | $OCH_3$ |
| 139. | NOH | $OCH_3$ | Br | H | $OCH_3$ |
| 140. | NOH | H | H | H | $OCH_3$ |
| 141. | $NCONH_2$ | $OCH_3$ | H | H | H |
| 142. | $NCONH_2$ | $OCH_3$ | Cl | H | H |
| 143. | $NCONH_2$ | $OCH_3$ | Br | H | H |
| 144. | $NCONH_2$ | H | H | H | H |
| 145. | $NCONH_2$ | $OCH_3$ | H | Cl | H |
| 146. | $NCONH_2$ | $OCH_3$ | Cl | Cl | H |
| 147. | $NCONH_2$ | $OCH_3$ | Br | Cl | H |
| 148. | $NCONH_2$ | H | H | Cl | H |
| 149. | $NCONH_2$ | $OCH_3$ | H | Br | H |
| 150. | $NCONH_2$ | $OCH_3$ | Cl | Br | H |
| 151. | $NCONH_2$ | $OCH_3$ | Br | Br | H |
| 152. | $NCONH_2$ | H | H | Br | H |
| 153. | $NCONH_2$ | $OCH_3$ | H | $OCH_3$ | H |
| 154. | $NCONH_2$ | $OCH_3$ | Cl | $OCH_3$ | H |

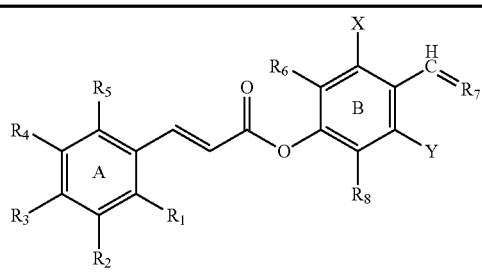

(4a)
X = Y = hydrogen; R1 = R4 = R5 = hydrogen

| S.No | R7 | R8 | R6 | R2 | R3 |
|---|---|---|---|---|---|
| 155. | NCONH₂ | OCH₃ | Br | OCH₃ | H |
| 156. | NCONH₂ | H | H | OCH₃ | H |
| 157. | NCONH₂ | OCH₃ | H | H | Cl |
| 158. | NCONH₂ | OCH₃ | Cl | H | Cl |
| 159. | NCONH₂ | OCH₃ | Br | H | Cl |
| 160. | NCONH₂ | H | H | H | Cl |
| 161. | NCONH₂ | OCH₃ | H | H | Br |
| 162. | NCONH₂ | OCH₃ | Cl | H | Br |
| 163. | NCONH₂ | OCH₃ | Br | H | Br |
| 164. | NCONH₂ | H | H | H | Br |
| 165. | NCONH₂ | OCH₃ | H | H | OCH₃ |
| 166. | NCONH₂ | OCH₃ | Cl | H | OCH₃ |
| 167. | NCONH₂ | OCH₃ | Br | H | OCH₃ |
| 168. | NCONH₂ | H | H | H | OCH₃ |
| 169. | 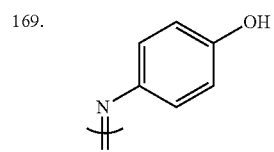 | OCH₃ | H | H | H |
| 170. | 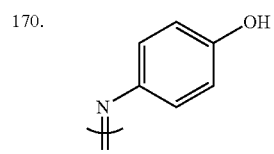 | OCH₃ | Cl | H | H |
| 171. | 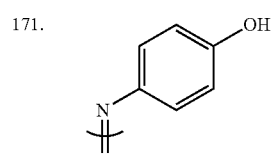 | OCH₃ | Br | H | H |
| 172. | 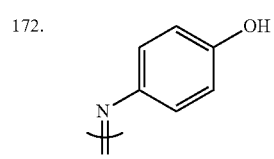 | H | H | H | H |
| 173. | 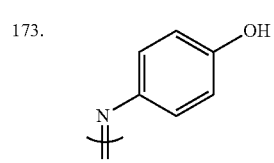 | OCH₃ | H | Cl | H |
| 174. | 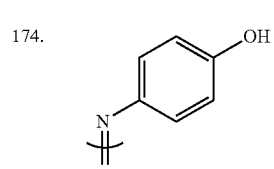 | OCH₃ | Cl | Cl | H |

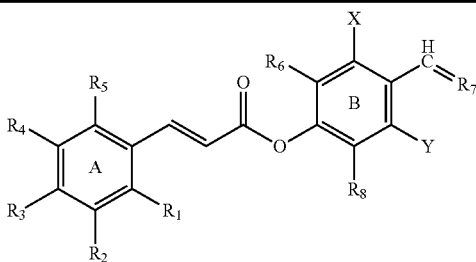

(4a)
X = Y = hydrogen; R1 = R4 = R5 = hydrogen

| S.No | R7 | R8 | R6 | R2 | R3 |
|---|---|---|---|---|---|
| 175. | (see figure) | OCH₃ | Br | Cl | H |
| 176. | (see figure) | H | H | Cl | H |
| 177. | (see figure) | OCH₃ | H | Br | H |
| 178. | (see figure) | OCH₃ | Cl | Br | H |
| 179. | (see figure) | OCH₃ | Br | Br | H |
| 180. | (see figure) | H | H | Br | H |
| 181. | (see figure) | OCH₃ | H | OCH₃ | H |
| 182. | (see figure) | OCH₃ | Cl | OCH₃ | H |

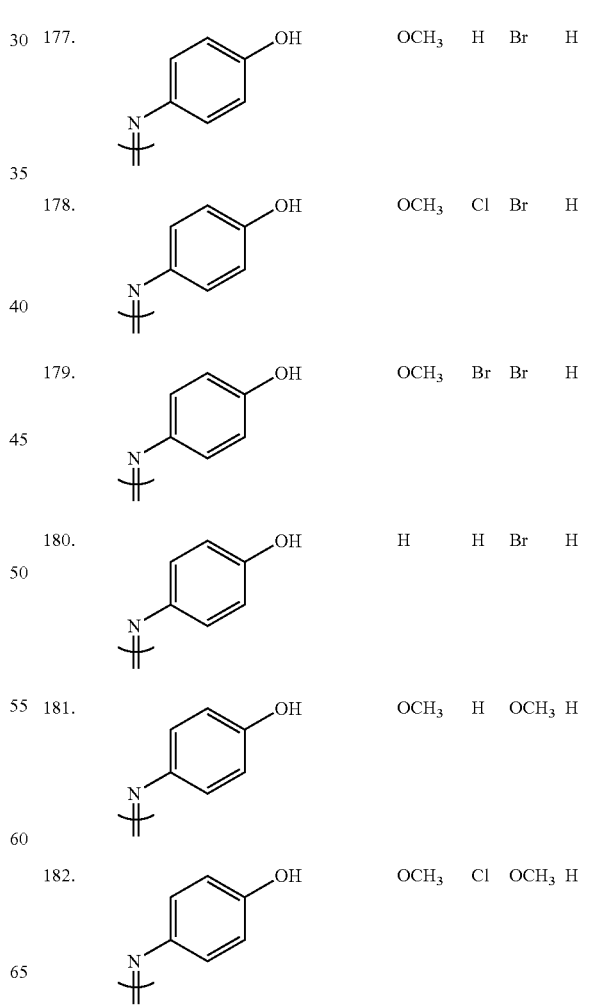

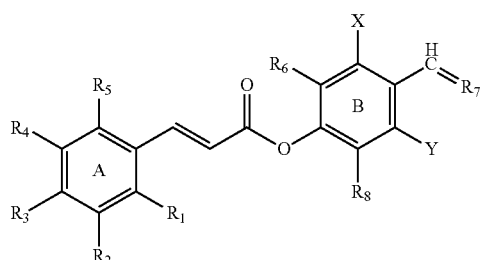
(4a)
X = Y = hydrogen; R1 = R4 = R5 = hydrogen
| S.No | R7 | R8 | R6 | R2 | R3 |
|---|---|---|---|---|---|
| 183. | 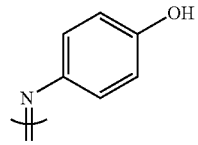 | OCH₃ | Br | OCH₃ | H |
| 184. | 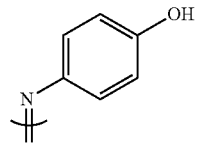 | H | H | OCH₃ | H |
| 185. | 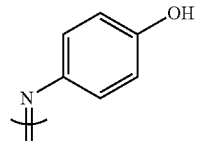 | OCH₃ | H | H | Cl |
| 186. | 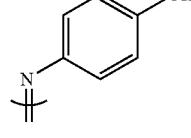 | OCH₃ | Cl | H | Cl |
| 187. | 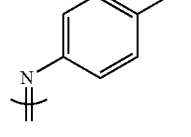 | OCH₃ | Br | H | Cl |
| 188. | 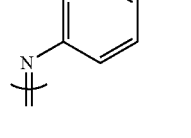 | H | H | H | Cl |
| 189. | 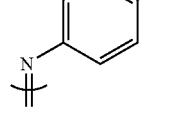 | OCH₃ | H | H | Br |
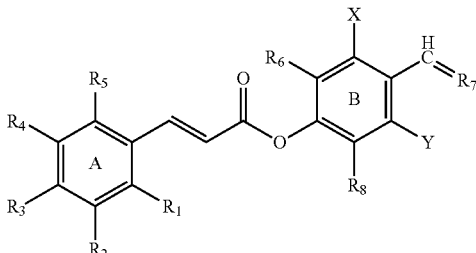
(4a)
X = Y = hydrogen; R1 = R4 = R5 = hydrogen
| S.No | R7 | R8 | R6 | R2 | R3 |
|---|---|---|---|---|---|
| 190. | 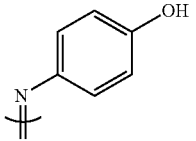 | OCH₃ | Cl | H | Br |
| 191. | 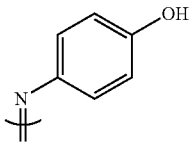 | OCH₃ | Br | H | Br |
| 192. | 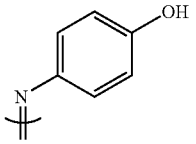 | H | H | H | Br |
| 193. | 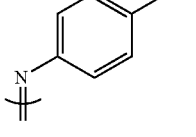 | OCH₃ | H | H | OCH₃ |
| 194. | 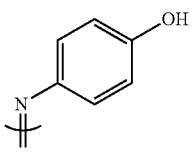 | OCH₃ | Cl | H | OCH₃ |
| 195. | 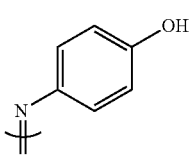 | OCH₃ | Br | H | OCH₃ |
| 196. | 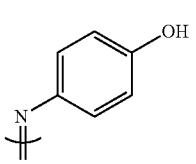 | H | H | H | OCH₃ |
| 197. | 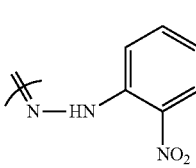 | OCH₃ | H | H | H |

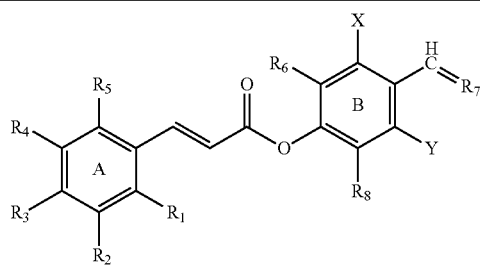
(4a)
X = Y = hydrogen; R1 = R4 = R5 = hydrogen
| S.No | R7 | R8 | R6 | R2 | R3 |
|---|---|---|---|---|---|
| 198. | 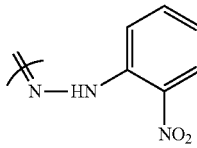 | OCH₃ | Cl | H | H |
| 199. | 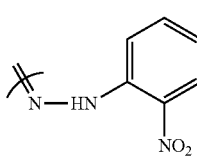 | OCH₃ | Br | H | H |
| 200. | 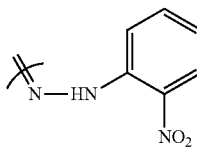 | H | H | H | H |
| 201. | 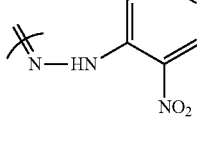 | OCH₃ | H | Cl | H |
| 202. | 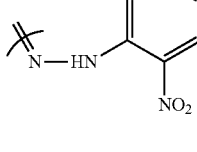 | OCH₃ | Cl | Cl | H |
| 203. | 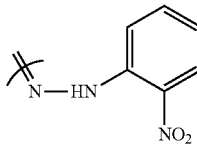 | OCH₃ | Br | Cl | H |
| 204. | 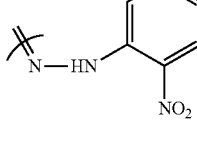 | H | H | Cl | H |
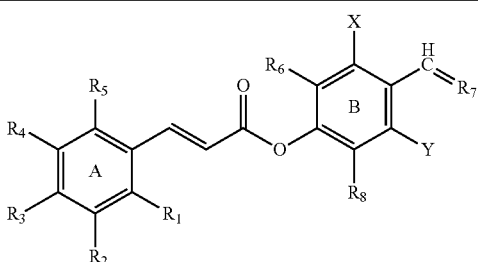
(4a)
X = Y = hydrogen; R1 = R4 = R5 = hydrogen
| S.No | R7 | R8 | R6 | R2 | R3 |
|---|---|---|---|---|---|
| 205. | 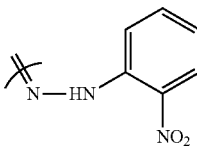 | OCH₃ | H | Br | H |
| 206. | 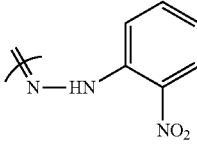 | OCH₃ | Cl | Br | H |
| 207. | 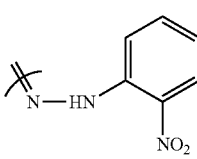 | OCH₃ | Br | Br | H |
| 208. | 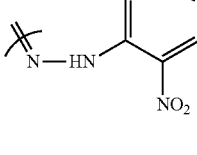 | H | H | Br | H |
| 209. | 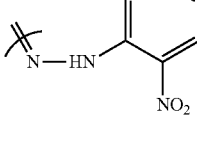 | OCH₃ | H | OCH₃ | H |
| 210. | 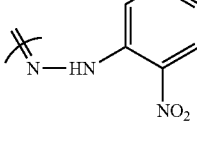 | OCH₃ | Cl | OCH₃ | H |
| 211. | 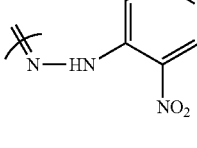 | OCH₃ | Br | OCH₃ | H |

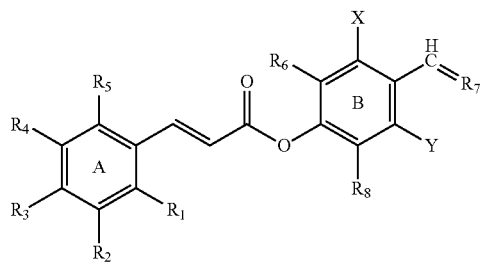

(4a)
X = Y = hydrogen; R1 = R4 = R5 = hydrogen

| S.No | R7 | R8 | R6 | R2 | R3 |
|---|---|---|---|---|---|
| 212. | 2,4-dinitrophenylhydrazone | H | H | OCH$_3$ | H |
| 213. | 2,4-dinitrophenylhydrazone | OCH$_3$ | H | H | Cl |
| 214. | 2,4-dinitrophenylhydrazone | OCH$_3$ | Cl | H | Cl |
| 215. | 2,4-dinitrophenylhydrazone | OCH$_3$ | Br | H | Cl |
| 216. | 2,4-dinitrophenylhydrazone | H | H | H | Cl |
| 217. | 2,4-dinitrophenylhydrazone | OCH$_3$ | H | H | Br |
| 218. | 2,4-dinitrophenylhydrazone | OCH$_3$ | Cl | H | Br |

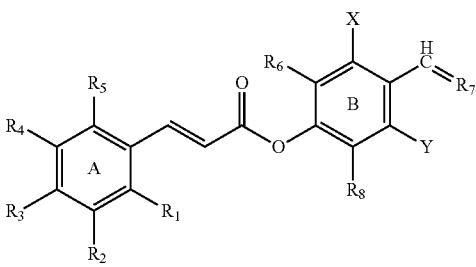

(4a)
X = Y = hydrogen; R1 = R4 = R5 = hydrogen

| S.No | R7 | R8 | R6 | R2 | R3 |
|---|---|---|---|---|---|
| 219. | 2,4-dinitrophenylhydrazone | OCH$_3$ | Br | H | Br |
| 220. | 2,4-dinitrophenylhydrazone | H | H | H | Br |
| 221. | 2,4-dinitrophenylhydrazone | OCH$_3$ | H | H | OCH$_3$ |
| 222. | 2,4-dinitrophenylhydrazone | OCH$_3$ | Cl | H | OCH$_3$ |
| 223. | 2,4-dinitrophenylhydrazone | OCH$_3$ | Br | H | OCH$_3$ |
| 224. | 2,4-dinitrophenylhydrazone | H | H | H | OCH$_3$ |

Preferred salts for the compounds listed above are hydrochloride, hydrobromide, sodium, potassium or magnesium.

According to another feature of this present invention, there is provided a process for the preparation of the compound represented by the formula I, wherein all symbols are as defined as earlier, as shown in scheme(I):

Scheme I

Step (i)

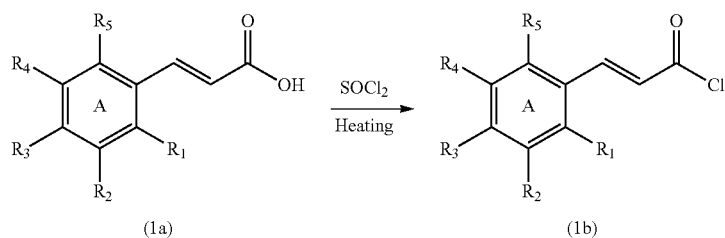

Step (ii)

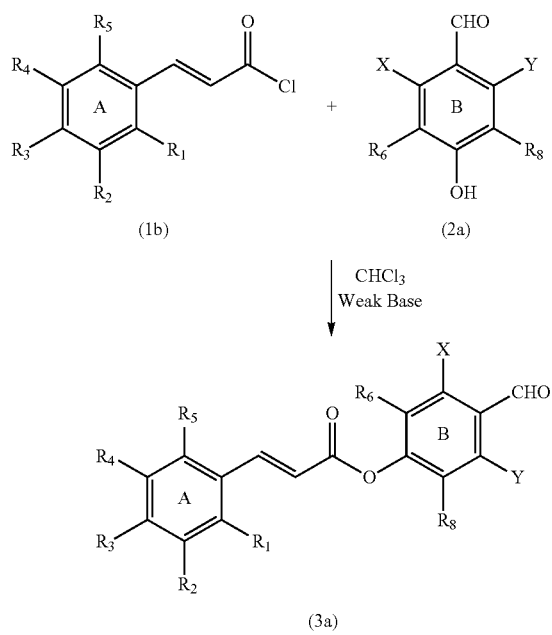

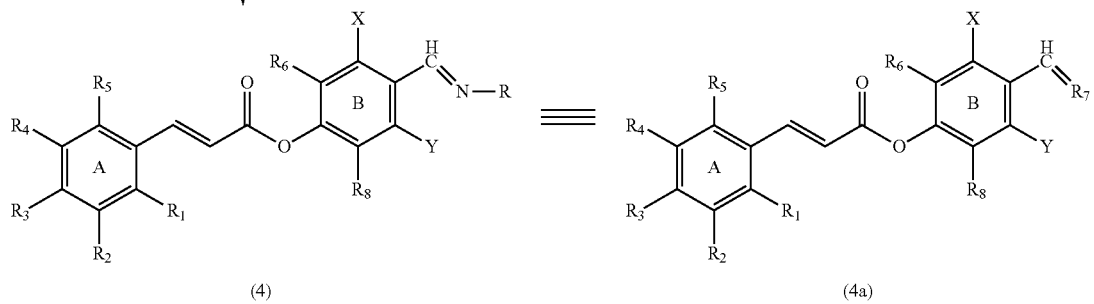

Structure (4a) is the equivalent structure of (4) where $R_7$ is as described earlier. In cases where $R_7$=O, the reaction is only until the second step.

The reaction of compound of general formula (1a) with thionyl chloride, where the groups R1, R2, R3, R4 and R5 of the compound (1a) have been defined earlier, to produce a compound of the general formula (1b) may be carried out in an inert atmosphere which may be maintained by using inert gases such as Nitrogen, Argon or Helium. Thionyl chloride is added drop wise to the compound (1a) which may be taken as such without any solvents. After addition of thionyl chloride, the reaction mixture is subjected to reflux. The reaction temperature may vary between 20° C. to 150° C., but more preferably between 60° C. to 90° C. The duration of the reaction may range from 1 to 24 hours, preferably between 4 to 6 hours. After refluxing the excess thionyl chloride is distilled off to obtain (1b).

The reaction of compound of general formula (1b) with a compound of general formula (2a) where the groups R6, R7, X and Y have been defined earlier may be carried out using a polar protic solvent like chloroform and in the presence of weak bases like DEA, TEA, Isopropylamine, pyridine, pipridine and the like, but more preferably with a base like TEA. The reaction temperature may range between 0 to 20° C., more preferably in the range of 5-10° C. The reaction time may range from 1 to 10 hours and following completion of the reaction, the product may be extracted from the reaction mixture by washing the organic phase with an aqueous solvent followed by precipitation using non polar solvents like butane, pentante, hexane, cyclohexane etc. to obtain compound of formula (3a).

The reaction of compound of general formula (3a) with an aliphatic or aromatic amines or amino acids, wherein the amino group reacts, is possible only when R7 is a keto functional group like (—CHO) or (C=O). This reaction may take place in the presence of any alcohol along with catalytic amounts of mineral acids such as sulphuric acid. The reaction temperature may vary from 0 to 100° C. preferably in the range of 50-70° C. and the reaction time may vary between 1 to 24 hours, preferably in the range of 4-7 hours. The schiff base or the imine thus formed may be precipitated or could be extracted after suitable workup procedures such as water quenching. The resultant molecule is the styryl carboxylate of general formula (4a) where the groups have been defined earlier.

The invention is explained in detail in the examples given below which are provided by way of illustration only and therefore should not be construed to limit the scope of the invention.

Example 1

Synthesis of 3-Phenyl-acrylic acid 4-(hydroxyimino-methyl)-phenyl ester

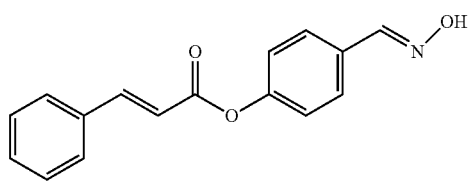 [SMILES: O=C(/C=C/c1ccccc1)Oc1ccc(/C=N/O)cc1]

Step (i)

Synthesis of cinnamoyl chloride

Cinnamic acid (50.0 g) was taken in a clean and dry three neck round bottom flask and thionyl chloride (175 ml) was added drop wise with constant stirring. The reaction mixture was refluxed at 70-80° C. for five hours. After reflux the excess thionyl chloride was distilled off. Hexane was added and distillation was performed again to remove any traces of thionyl chloride. The product was then transferred to an amberlite bottle stored. (Yield 53.0 g)

Step (ii)

Synthesis of 3-Phenyl-acrylic acid 4-formyl-phenyl ester 4 hydroxy benzaldehyde (14.69 g) was taken in a clean and dry two neck round bottom flask and chloroform (200 ml) was added with constant stirring. The reaction mixture was cooled to 10-15 and Nicotonyl chloride (20.0 g) was added drop wise. Stirring was continued for another 15 minutes and TEA (16.44 ml) was added drop wise and the reaction was allowed to stir for 4 hours. It was then transferred to a separating funnel and washed twice with water (2×250 ml). The chloroform layer was separated and further washed with 10% NaOH solution (2×250 ml) and then dried with anhydrous sodium sulphate. The chloroform layer was then filtered and concentrated under vaccum. Hexane was then added to the concentrated chloroform layer and the solid formed was filtered and dried. (Yield 15.7 g)

Step (iii)

Synthesis of 3-Phenyl-acrylic acid 4-(hydroxyimino-methyl)-phenyl ester

Stage (ii) compound (2.5 g) was taken in a clean and dry round bottom flask and Methanol (25 ml) was added. The reaction mixture was cooled to 15 C and sodium acetate (2.5 g) was added. Hydroxylamine hydrochloride (1.25 g) dissolved in 10 ml of water was added drop wise to the reaction mixture with constant stirring. Stirring was continued for 4 hours at room temperature.

The reaction mixture was then transferred to a beaker containing 100 ml of water. The precipitated solid was filtered, washed with water and then followed by hexane and dried. (Yield 1.2 g)

The synthesized compound was confirmed by proton NMR.

7.25 (d, 1H), 7.61 (d, 1H), 6.67 (d, 1H), 6.64 (d, 1H), 8.17 (s, 1H), 1.28 (s, 1H), 6.674 (d, J=16.5, 1H), 7.929 (d, J=16.5, 1H), 7.28 (d, 1H), 7.24 (t, 1H), 7.23 (t, 1H), 7.46 (t, 1H), 7.45 (d, 1H)

Example 2

Synthesis of 3-Phenyl-acrylic acid 4-(hydroxyimino-methyl)-2-methoxy-phenyl ester

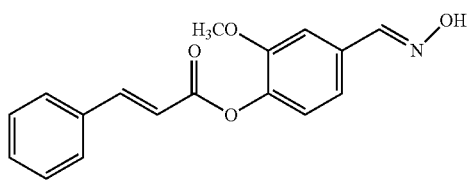 [SMILES: COc1cc(/C=N/O)ccc1OC(=O)/C=C/c1ccccc1]

Step (i)

Synthesis of cinnamoyl chloride

Cinnamic acid (50.0 g) was taken in a clean and dry three neck round bottom flask and thionyl chloride (175 ml) was added drop wise with constant stirring. The reaction mixture was refluxed at 70-80° C. for five hours. After reflux the excess thionyl chloride was distilled off. Hexane was added and distillation was performed again to remove any traces of thionyl chloride. The product was then transferred to an amberlite bottle stored. (Yield 53.0 g)

Step (ii)

Synthesis of 3-Phenyl-acrylic acid 4-formyl-2-methoxy-phenyl ester (Cinnamoyl vanillin)

Vanillin (22.8 g) was taken in a clean and dry round bottom flask and chloroform (200 ml) was added whilst stirring. The reaction mixture was cooled to 5-10° C. Cinnamoyl chloride (25.0 g) was added drop wise. Stirring was continued for another 15 minutes and TEA (20.55 ml) was added drop wise while stirring. The reaction was allowed to continue for 5 hours with constant stirring. The reaction mixture was then transferred to a 1 L beaker and washed twice with water (2×250 ml). The chloroform layer was separated and further washed with 10% NaOH solution (2×250 ml) and then dried with anhydrous sodium sulphate. The chloroform layer was then filtered and concentrated under vacuum. Hexane was then added to the concentrated chloroform layer and the solid formed was filtered and dried. (Yield 16.2 g)

Step (iii)

Synthesis of 3-Phenyl-acrylic acid 4-(hydroxyimino-methyl)-2-methoxy-phenyl ester Cinnamoyl vanniline (5.7 g) was taken in a round bottom flask and methanol (50 ml) was added. The reaction mixture was cooled to 15° C. and sodium acetate (7.89 g) was added. Hydroxyl amine (2.8 g) was dissolved in (25 ml) of water and this was added drop wise to the reaction mixture under constant stirring. The reaction mixture was allowed to stir for 4 hours and then transferred into a beaker containing 100 ml of water. The precipitated solid was filtered, washed with water, followed by hexane and then dried. (Yield 2.8 g)

7.25 (d, 1H), 7.61 (d, 1H), 6.67 (d, 1H), 3.85 (s, 3H), 8.17 (s, 1H), 1.28 (s, 1H), 6.674 (d, J=16.5, 1H), 7.929 (d, J=16.5, 1H), 7.28 (d, 1H), 7.24 (t, 1H), 7.23 (t, 1H), 7.46 (t, 1H), 7.45 (d, 1H)

Example 3

Synthesis of 4-[3-Methoxy-4-(3-phenyl-acryloyloxy)-phenyl]-6-Methyl-2-oxo-1,2,3,4-tetrahydropyrimidine-5-carboxylic acid ethyl ester (C10)

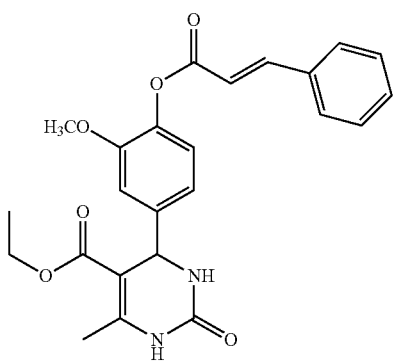 [SMILES: CCOC(=O)C1=C(C)NC(=O)NC1c1ccc(OC(=O)/C=C/c2ccccc2)c(OC)c1]

Step (i)

Synthesis of cinnamoyl chloride

Cinnamic acid (50.0 g) was taken in a clean and dry three neck round bottom flask and thionyl chloride (175 ml) was added drop wise with constant stirring. The reaction mixture was refluxed at 70-80° C. for five hours. After reflux the excess thionyl chloride was distilled off. Hexane was added and distillation was performed again to remove any traces of thionyl chloride. The product was then transferred to an amberlite bottle and stored. (Yield 53.0 g)

Step (ii)

Synthesis of 3-Phenyl-acrylic acid 4-formyl-2-methoxy-phenyl ester (Cinnamoyl vanillin)

Vanillin (22.8 g) was taken in a clean and dry round bottom flask and chloroform (200 ml) was added whilst stirring. The reaction mixture was cooled to 5-10° C. Cinnamoyl chloride (25.0 g) was added drop wise. Stirring was continued for another 15 minutes and TEA (20.55 ml) was added drop wise while stirring. The reaction was allowed to continue for 5 hours with constant stirring. The reaction mixture was then transferred to a 1 L beaker and washed twice with water (2×250 ml). The chloroform layer was separated and further washed with 10% NaOH solution (2×250 ml) and then dried with anhydrous sodium sulphate. The chloroform layer was then filtered and concentrated under vacuum. Hexane was then added to the concentrated chloroform layer and the solid formed was filtered and dried. (Yield 16.2 g)

Step (iii)

Synthesis of 4-[3-Methoxy-4-(3-phenyl-acryloyloxy)-phenyl]-6-Methyl-2-oxo-1,2,3,4-tetrahydropyrimidine-5-carboxylic acid ethyl ester Cinnamoyl vanilline (3.0 g), Urea (0.64 g) and Ethylacetoacetate (2.56 ml) were taken in a clean and dry three neck round bottom flask and Methanol (50 ml) and Sulphuric acid (5 drops) were added. This reaction mixture was subjected to reflux at 60-80° C. for 5 hours. After reflux, the reaction mixture was transferred to a beaker containing 200 ml of water. The precipitated solid was filtered, washed with water and followed with hexane and then dried. (Yield 1.42 g) 5.61 (s, 1H), 5.53 (s, 1H), 6.51 (s, 1H), 6.83 (d, 2H), 4.21 (m, 2H), 1.26 (t, 3H), 2.23 (s, 3H), 3.91 (s, 3H), 6.8 (d, 1H, J=16.5), 7.9 (d, 1H, J=16.5), 7.40 (d, 2H), 7.25 (t, 1H,)

Example 4

Synthesis of 2-methoxy-4-((E)-ureidomethyl)phenyl cinnamate (C9)

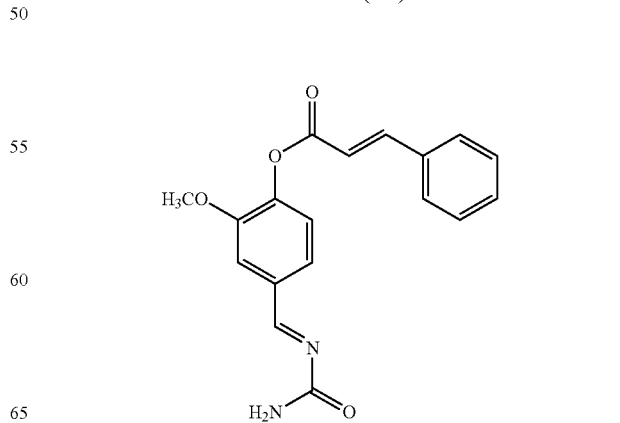

41

Synthesis of Cinnamoyl Chloride

Step (i)

Cinnamic acid (50.0 g) was taken in a clean and dry three neck round bottom flask and thionyl chloride (175 ml) was added drop wise with constant stirring. The reaction mixture was refluxed at 70-80° C. for five hours. After reflux the excess thionyl chloride was distilled off. Hexane was added and distillation was performed again to remove any traces of thionyl chloride. The product was then transferred to an amberlite bottle stored. (Yield 53.0 g)

Step (ii)

Synthesis of 3-Phenyl-acrylic acid 4-formyl-2-methoxy-phenyl ester (Cinnamoyl vanillin)

Vanillin (22.8 g) was taken in a clean and dry round bottom flask and chloroform (200 ml) was added whilst stirring. The reaction mixture was cooled to 5-10° C. Cinnamoyl chloride (25.0 g) was added drop wise. Stirring was continued for another 15 minutes and TEA (20.55 ml) was added drop wise while stirring. The reaction was allowed to continue for 5 hours with constant stirring. The reaction mixture was then transferred to a 1 L beaker and washed twice with water (2×250 ml). The chloroform layer was separated and further washed with 10% NaOH solution (2×250 ml) and then dried with anhydrous sodium sulphate. The chloroform layer was then filtered and concentrated under vacuum. Hexane was then added to the concentrated chloroform layer and the solid formed was filtered and dried. (Yield 16.2 g)

Step (iii)

Synthesis of 2-methoxy-4-((E)-ureidomethyl)phenyl cinnamate

Cinnamoyl vanillin (5.0 g) was taken in a two next round bottom flask along with urea (2.2 g). Toulene (25 ml) was added and stirred and catalytic amounts of Paratoulylsulphonic acid (0.1 g) was added. The reaction mixture was refluxed for 4 hours at 100-110° C. After reflux the solvent was removed by distillation and the product was washed with water and followed by hexane and then dried. (Yield 3.12 g)

NMR Assignment 7.10 (1H, d), 7.20 (1H, d), 7.10 (1H, s), 3.80 (3H, s), 8.15 (1H, s), 6.20 (1H, d, J=16.5 MHz), 7.71 (1H, d, J=16.5 MHz), 7.35 (1H, d, Aromatic)

42

Example 5

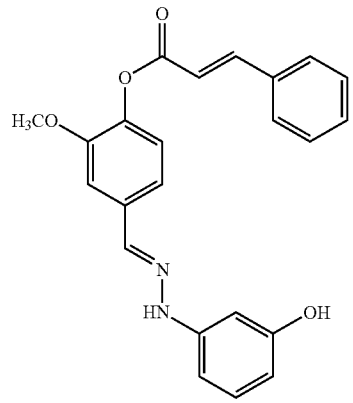 [SMILES: COc1cc(/C=N/Nc2cccc(O)c2)ccc1OC(=O)/C=C/c1ccccc1]

Synthesis of 3-Phenyl-acrylic acid 4-benzylidineamino-3'-hydroxyaniline-2-methoxy-phenyl ester (C4)

Step (i)

Synthesis of Cinnamoyl Chloride

Cinnamic acid (50.0 g) was taken in a clean and dry three neck round bottom flask and thionyl chloride (175 ml) was added drop wise with constant stirring. The reaction mixture was refluxed at 70-80° C. for five hours. After reflux the excess thionyl chloride was distilled off. Hexane was added and distillation was performed again to remove any traces of thionyl chloride. The product was then transferred to an amberlite bottle stored. (Yield 53.0 g)

Step (ii)

Synthesis of 3-Phenyl-acrylic acid 4-formyl-2-methoxy-phenyl ester (Cinnamoyl vanillin)

Vanillin (22.8 g) was taken in a clean and dry round bottom flask and chloroform (200 ml) was added whilst stirring. The reaction mixture was cooled to 5-10° C. Cinnamoyl chloride (25.0 g) was added drop wise. Stirring was continued for another 15 minutes and TEA (20.55 ml) was added drop wise while stirring. The reaction was allowed to continue for 5 hours with constant stirring. The reaction mixture was then transferred to a 1 L beaker and washed twice with water (2×250 ml). The chloroform layer was separated and further washed with 10% NaOH solution (2×250 ml) and then dried with anhydrous sodium sulphate. The chloroform layer was then filtered and concentrated under vacuum. Hexane was then added to the concentrated chloroform layer and the solid formed was filtered and dried. (Yield 16.2 g)

Cinnamoyl vanillin (1.5 g) was taken in a clean two neck round bottom flask and Ethanol (25 ml) was added with stirring. 3-Aminophenol (0.6 g) was added lot by lot with constant stirring. After completion of addition, 2 drops of sulphuric acid was added. The reaction mixture was refluxed for 4 hours at 75-80° C. The solid product formed was filtered and washed with Ethanol and followed by water and finally by hexane and dried. (Yield 0.89 g)

NMR Assignment 6.81 (1H, d), 7.15 (1H, d), 7.10 (1H, s), 3.91 (3H, s), 6.72 to 7.10 (Aromatic), 6.20 (1H, d, J=16.5 MHz), 7.71 (1H, d, J=16.5 MHz), 7.15 to 7.35 (Aromatic)

Example 6

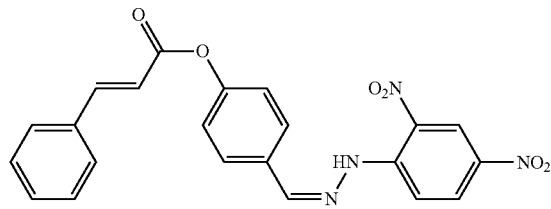 [SMILES: O=C(/C=C/c1ccccc1)Oc1ccc(/C=N\Nc2ccc([N+](=O)[O-])cc2[N+](=O)[O-])cc1]

Synthesis of 3-phenyl-acrylicacid4-[(2, 4-dinitro-phenyl)-hydrazonomethyl]-phenyl ester (C11)

Step (i)

Synthesis of Cinnamoyl Chloride

Cinnamic acid (50.0 g) was taken in a clean and dry three neck round bottom flask and thionyl chloride (175 ml) was added drop wise with constant stirring. The reaction mixture was refluxed at 70-80° C. for five hours. After reflux the excess thionyl chloride was distilled off. Hexane was added and distillation was performed again to remove any traces of thionyl chloride. The product was then transferred to an amberlite bottle stored. (Yield 53.0 g)

Step (ii)

Synthesis of 3-Phenyl-acrylic acid 4-formyl-phenyl ester 4-hydroxy benzaldehyde (14.69 g) was taken is a clean and dry two neck round bottom flask and Chloroform (200 ml) was added whilst stirring. The reaction mixture was cooled to 5-10° C. Nicotinyl chloride (20.0 g) was added drop wise and stirring was continued for 15 minutes. TEA (16.44 ml) was added drop wise and the reaction was allowed to stir for 4 hours. It was then transferred to a separating funnel and washed twice with water (2×250 ml). The chloroform layer was separated and further washed with 10% NaOH solution (2×250 ml) and then dried with anhydrous sodium sulphate. The chloroform layer was then filtered and concentrated under vaccum. Hexane was then added to the concentrated chloroform layer and the solid formed was filtered and dried. (Yield 15.7 g)

Step (iii)

Synthesis of 3-phenyl-acrylicacid4-[(2, 4-dinitro-phenyl)-hydrazonomethyl]-phenyl ester Cinnamoyl 4-hydroxy benzaldehyde (1 g) was taken in a clean and dry round bottom flask and methanol (10 ml) was added. 2,4 Dinitrophenylhydrazine (0.00 g) was added slowly into the reaction mixture and methanol (20 ml) was added. The reaction mixture was allowed to stir for 3 hours at room temperature. The solid formed was then filtered and washed with water and followed by hexane. (Yield 0.85 g)

NMR Assignment 6.81 (1H, d), 7.15 (1H, d), 7.6 (1H, s), 7.12 (1H, d), 8.30 (1H, s), 5.0 (1H, s), 8.5 (1H, s), 8.21 (1H, d), 6.62 (1H, d), 6.20 (1H, d, J=16.5 MHz), 7.71 (1H, d, J=16.5 MHz), 7.15 to 7.35 (Aromatic)

Example 7

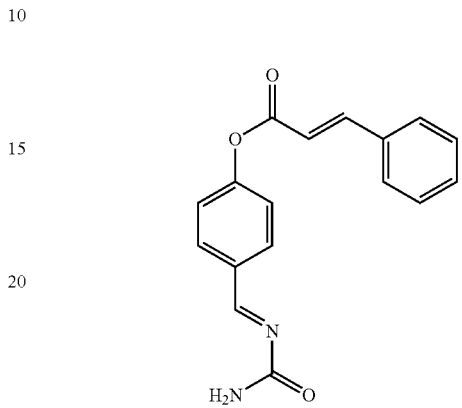

Synthesis of 4-((E)-ureidomethyl)phenyl cinnamate (C2)

Step (i)

Synthesis of Cinnamoyl Chloride

Cinnamic acid (50.0 g) was taken in a clean and dry three neck round bottom flask and thionyl chloride (175 ml) was added drop wise with constant stirring. The reaction mixture was refluxed at 70-80° C. for five hours. After reflux the excess thionyl chloride was distilled off. Hexane was added and distillation was performed again to remove any traces of thionyl chloride. The product was then transferred to an amberlite bottle stored. (Yield 53.0 g)

Step (ii)

Synthesis of 3-Phenyl-acrylic acid 4-formyl-phenyl ester 4 hydroxy benzaldehyde (14.69 g) was taken in a clean and dry two neck round bottom flask and chloroform (200 ml) was added with constant stirring. The reaction mixture was cooled to 10-15 and Nicotonyl chloride (20.0 g) was added drop wise. Stirring was continued for another 15 minutes and TEA (16.44 ml) was added drop wise and the reaction was allowed to stir for 4 hours. It was then transferred to a separating funnel and washed twice with water (2×250 ml). The chloroform layer was separated and further washed with 10% NaOH solution (2×250 ml) and then dried with anhydrous sodium sulphate. The chloroform layer was then filtered and concentrated under vaccum. Hexane was then added to the concentrated chloroform layer and the solid formed was filtered and dried. (Yield 15.7 g)

Step (iii)

Synthesis of 4-((E)-ureidomethyl)phenyl cinnamate compound of step 2 (5 g) was taken in a clean and dry two neck round bottom flask and PTSA (3.8 g) was added. Urea (1.3 g) was then added and Toulene (50 ml) was added with stirring. The reaction mixture was refluxed for 5 hours at 100-110 and allowed to cool over night at room temperature. The precipitated compound was filtered, washed with water and followed by hexane and dried. (Yield 3.34 g)

NMR Assignment 7.10 to 7.60 (Aromatic), 8.20 (1H, s), 5.0 (2H, s), 6.20 (1H, d, J=16.5 MHz), 7.71 (1H, d, J=16.5 MHz), 7.15 to 7.35 (Aromatic)

Example 8

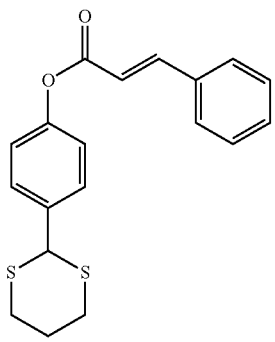 [SMILES: O=C(/C=C/c1ccccc1)Oc1ccc(C2SCCCS2)cc1]

Synthesis of 4-(1,3-dithian-2-yl)phenyl cinnamate (C3)

Step (i)

Synthesis of Cinnamoyl Chloride

Cinnamic acid (50.0 g) was taken in a clean and dry three neck round bottom flask and thionyl chloride (175 ml) was added drop wise with constant stirring. The reaction mixture was refluxed at 70-80° C. for five hours. After reflux the excess thionyl chloride was distilled off. Hexane was added and distillation was performed again to remove any traces of thionyl chloride. The product was then transferred to an amberlite bottle stored. (Yield 53.0 g)

Step (ii)

Synthesis of 3-Phenyl-acrylic acid 4-formyl-phenyl ester 4 hydroxy benzaldehyde (14.69 g) was taken in a clean and dry two neck round bottom flask and chloroform (200 ml) was added with constant stirring. The reaction mixture was cooled to 10-15 and Nicotonyl chloride (20.0 g) was added drop wise. Stirring was continued for another 15 minutes and TEA (16.44 ml) was added drop wise and the reaction was allowed to stir for 4 hours. It was then transferred to a separating funnel and washed twice with water (2×250 ml). The chloroform layer was separated and further washed with 10% NaOH solution (2×250 ml) and then dried with anhydrous sodium sulphate. The chloroform layer was then filtered and concentrated under vaccum. Hexane was then added to the concentrated chloroform layer and the solid formed was filtered and dried. (Yield 15.7 g)

Step (iii)

Synthesis of 4-(1,3-dithian-2-yl)phenyl cinnamate

Compound from step (ii) (6.0 g) was taken in a clean and dry two neck round bottom flask and Chloroform (60 ml) was added with stirring. 1,3 Dithiane (2.7 g) and catalytic amount of iodine (0.1 g) was added and the reaction mixture was allowed to stir at room temperature for 5 hours. It was then quenched with cold water and the organic layer was separated which was further washed with water. The chloroform layer was then concentrated and the solid obtained was filtered, washed with hexane and then dried. (Yield 7.0 g)

NMR Assignment 2.44 (4H, t,), 2.03 (2H, m), 4.5 (2H, s), 6.8-7.1 (Aromatic), 6.20 (1H, d, J=16.5 MHz), 7.71 (1H, d, J=16.5 MHz), 7.15-7.35 (Aromatic).

The invention claimed is:

1. A compound of Formula (I)

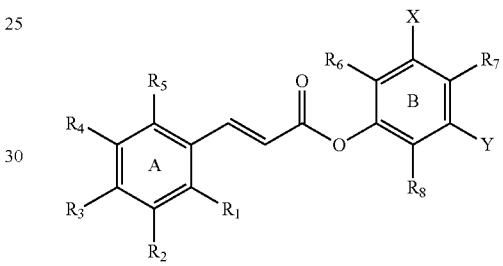

Formula (I)

wherein $R_1$, $R_2$, $R_3$, $R_4$, $R_5$, $R_6$ and $R_8$, X and Y are hydrogens, and $R_7$ is —C=N—OH, wherein the compound is 3-Phenyl-acrylic acid 4-(hydroxyimino-methyl)-phenyl ester, having the chemical formula as follows:

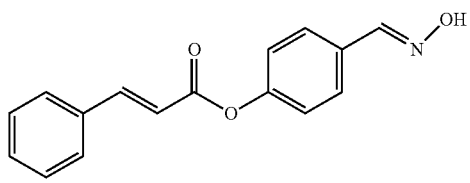 [SMILES: O=C(/C=C/c1ccccc1)Oc1ccc(/C=N/O)cc1]

or a pharmaceutically acceptable salt thereof.

2. The compound of claim 1 made by performing the following steps:

Step (i) Cinnamic acid (50.0 g) is taken in a clean and dry three neck round bottom flask and thionyl chloride (175 ml) is added drop wise with constant stirring; the reaction mixture is refluxed at 70-80° C. for five hours; after reflux the excess thionyl chloride is distilled off. Hexane is added and distillation is performed again to remove any traces of thionyl chloride; the product is then transferred to an amberlite bottle stored (yield 53.0 g);

Step (ii) Synthesis of 3-Phenyl-acrylic acid 4-formyl-phenyl ester: 4 hydroxy benzaldehyde (14.69 g) is taken in a clean and dry two neck round bottom flask and chloroform (200 ml) is added with constant stirring; the reaction mixture is cooled to 10-15 and Nicotonyl chloride (20.0 g) is added drop wise; stirring is continued for another 15 minutes and TEA (16.44 ml) is added drop wise and the reaction is allowed to stir for 4 hours; it is then transferred to a separating funnel and washed twice with water (2×250 ml); the chloroform layer is separated and further washed with 10% NaOH solution (2×250 ml) and then dried with anhydrous sodium sulphate; the chloroform layer is then filtered and concentrated under vacuum; hexane is then added to the concentrated chloroform layer and the solid formed is filtered and dried (yield 15.7 g);

Step (iii) Synthesis of 3-Phenyl-acrylic acid 4-(hydroxy-imino-methyl)-phenyl ester: Stage (ii) compound (2.5 g) is taken in a clean and dry round bottom flask and Methanol (25 ml) is added; the reaction mixture is cooled to 15 C and sodium acetate (2.5 g) is added; hydroxylamine hydrochloride (1.25 g) dissolved in 10 ml of water is added drop wise to the reaction mixture with constant stirring; stirring is continued for 4 hours at room temperature; the reaction mixture is then transferred to a beaker containing 100 ml of water; the precipitated solid is filtered, washed with water and then followed by hexane and dried (yield 1.2 g); and the synthesized compound is confirmed by proton NMR.

3. A method for inducing a physiological effect in a subject, the physiological effect selected from the group consisting of: reducing the body weight of said subject, reducing fasting blood glucose in said subject, reducing cholesterol in the plasma of said subject, is reducing triglyceride levels in plasma of said subject, increasing the level of high density lipoprotein (HDL) in plasma of said subject, decreasing the level of low-density lipoproteins (LDL) in plasma of said subject, decreasing the systolic blood pressure and diastolic blood pressure of said subject, and decreasing the level of TNF-α in the plasma in said subject; wherein the method comprises administering to said subject a composition comprising an effective amount of phenyl-acrylic acid 4-(hydroxyimino-methyl)-phenyl ester, having the chemical formula as follows:

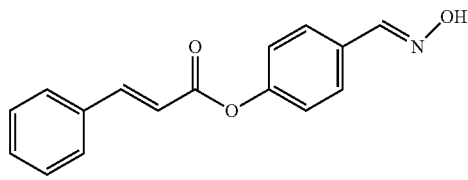 [SMILES: O=C(/C=C/c1ccccc1)Oc1ccc(/C=N/O)cc1]

or a pharmaceutically acceptable salt thereof.

4. The method of claim 3 wherein the physiological effect is reducing the body weight of said subject.

5. The method of claim 3 wherein the physiological effect is reducing fasting blood glucose in said subject.

6. The method of claim 3 wherein the physiological effect is reducing cholesterol in the plasma of said subject.

7. The method of claim 3 wherein the physiological effect is reducing triglyceride levels in plasma of said subject.

8. The method of claim 3 wherein the physiological effect is an increase in high density lipoprotein (HDL) in plasma of said subject.

9. The method of claim 3 wherein the physiological effect is a decrease in low-density lipoproteins (LDL) in plasma of said subject.

10. The method of claim 3 wherein the physiological effect is a decrease in systolic blood pressure and diastolic blood pressure of said subject.

11. The method of claim 3 wherein the physiological effect is a decrease in TNF-α in plasma in said subject.

12. A compound of Formula (I) comprising the following structure

Formula (I)

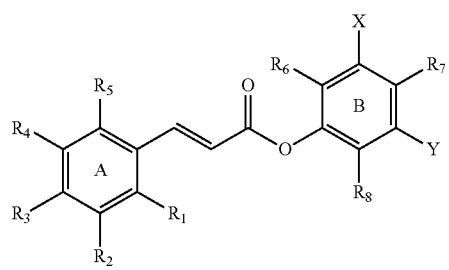

wherein $R_1$, $R_2$, $R_3$, $R_4$, $R_5$ and $R_8$, X and Y are hydrogens, $R_7$ is —C=N—OH
and $R_6$ a methoxy group;

wherein the compound is 3-Phenyl-acrylic acid 4-(hydroxyimino-methyl)-2-methoxy-phenyl ester, having the chemical formula as follows:

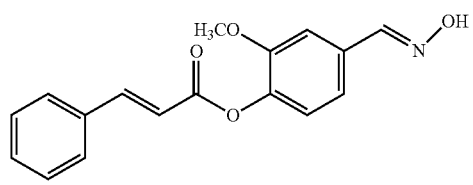 [SMILES: COc1cc(/C=N/O)ccc1OC(=O)/C=C/c1ccccc1]

and pharmaceutically acceptable salts thereof.

13. The compound of claim 12 synthesized by performing the following steps:

Step (i) Cinnamic acid (50.0 g) is taken in a clean and dry three neck round bottom flask and thionyl chloride (175 ml) is added drop wise with constant stirring; the reaction mixture is refluxed at 70-80° C. for five hours; after reflux the excess thionyl chloride is distilled off, hexane is added and distillation is performed again to remove any traces of thionyl chloride. The product is then transferred to an amberlite bottle stored (yield 53.0 g);

Step (ii) Synthesis of 3-Phenyl-acrylic acid 4-formyl-2-methoxy-phenyl ester: (Cinnamoyl vanillin) Vanillin (22.8 g) is taken in a clean and dry round bottom flask and chloroform (200 ml) is added whilst stirring; the reaction mixture is cooled to 5-10° C.; cinnamoyl chloride (25.0 g) is added drop wise; stirring is continued for another 15 minutes and TEA (20.55 ml) is added drop wise while stirring; the reaction is allowed to continue for 5 hours with constant stirring. The reaction mixture is then transferred to a 1 L beaker and washed twice with water (2×250 ml); the chloroform layer is separated and further washed with 10% NaOH solution (2×250 ml) and then dried with anhydrous sodium sulphate; the chloroform layer is then filtered and concentrated under vacuum; hexane is then added to the concentrated chloroform layer and the solid formed is filtered and dried (yield 16.2 g);

Step (iii) Synthesis of 3-Phenyl-acrylic acid 4-(hydroxy-imino-methyl)-2-methoxy-phenyl ester: Cinnamoyl vanillin (5.7 g) is taken in a round bottom flask and methanol (50 ml) is added; the reaction mixture is cooled to 15° C. and sodium acetate (7.89 g) is added; hydroxyl amine (2.8 g) is dissolved in (25 ml) of water and this is added drop wise to the reaction mixture under constant stirring; the reaction mixture is allowed to stir for 4 hours and then transferred into a beaker containing 100 ml of water; the precipitated solid is filtered, washed with water, followed by hexane and then dried (yield 2.8 g); and the synthesized compound is confirmed by proton NMR.

14. A method for inducing a physiological effect in a subject, wherein the physiological effect is selected from the group consisting of: a decrease in body weight of said subject and a decrease in the level of fasting blood glucose in said subject; wherein the method comprises administering to said subject a composition comprising an effective amount of 3-Phenyl-acrylic acid 4-(hydroxyimino-methyl)-2-methoxy-phenyl ester, having the chemical formula as follows:

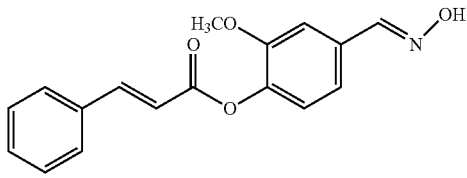 [SMILES: COc1cc(/C=N/O)ccc1OC(=O)/C=C/c1ccccc1]

or a pharmaceutically acceptable salt thereof.

15. The method of claim 14 wherein the physiological effect is a decrease in body weight of said subject.

16. The method of claim 14 wherein the physiological effect is a decrease in the level of fasting blood glucose in said subject.

* * * * *